United States Patent
Jin et al.

(10) Patent No.: US 12,077,792 B2
(45) Date of Patent: Sep. 3, 2024

(54) ENGINEERED MICROORGANISMS FOR PRODUCTION OF 2'FUCOSYLLACTOSE AND L-FUCOSE

(71) Applicants: THE BOARD OF TRUSTEES OF THE UNIVERSITY OF ILLINOIS, Urbana, IL (US); KOREA UNIVERSITY RESEARCH AND BUSINESS FOUNDATION, Seoul (KR)

(72) Inventors: Yong-Su Jin, Champaign, IL (US); Jingjing Liu, Urbana, IL (US); Sora Yu, Namyangju-si (KR); Eun Ju Yun, Geumcheon-gu (KR); Suryang Kwak, Savoy, IL (US); Kyoung Heon Kim, Seoul (KR); Jaewon Lee, Savoy, IL (US)

(73) Assignees: The Board of Trustees of the University of Illinois, Urbana, IL (US); Korea University Research and Business Foundation, Seoul (KR)

(*) Notice: Subject to any disclaimer, the term of this patent is extended or adjusted under 35 U.S.C. 154(b) by 0 days.

(21) Appl. No.: 17/054,969

(22) PCT Filed: May 15, 2019

(86) PCT No.: PCT/US2019/032474
§ 371 (c)(1),
(2) Date: Nov. 12, 2020

(87) PCT Pub. No.: WO2019/222391
PCT Pub. Date: Nov. 21, 2019

(65) Prior Publication Data
US 2021/0214705 A1 Jul. 15, 2021

Related U.S. Application Data

(60) Provisional application No. 62/671,459, filed on May 15, 2018.

(51) Int. Cl.
| | | |
|---|---|---|
| *C12N 9/88* | (2006.01) | |
| *C07K 14/395* | (2006.01) | |
| *C12N 1/21* | (2006.01) | |
| *C12N 9/04* | (2006.01) | |
| *C12N 9/10* | (2006.01) | |
| *C12N 15/81* | (2006.01) | |
| *C12P 19/18* | (2006.01) | |

(52) U.S. Cl.
CPC ............ *C12N 9/88* (2013.01); *C07K 14/395* (2013.01); *C12N 9/0006* (2013.01); *C12N 9/1051* (2013.01); *C12N 15/81* (2013.01); *C12P 19/18* (2013.01); *C12Y 101/01271* (2013.01); *C12Y 402/01047* (2013.01); *C12N 2800/102* (2013.01)

(58) Field of Classification Search
None
See application file for complete search history.

(56) References Cited

U.S. PATENT DOCUMENTS

| | | | |
|---|---|---|---|
| 9,938,549 B2 * | 4/2018 | Jennewein | C12N 9/2402 |
| 2015/0240277 A1 * | 8/2015 | Jennewein | C12P 19/18 435/97 |
| 2016/0017390 A1 * | 1/2016 | Wong | A61P 7/00 435/99 |
| 2016/0208302 A1 * | 7/2016 | Dekany | C12P 19/00 |
| 2019/0323052 A1 * | 10/2019 | Hollands | C12P 19/00 |
| 2021/0363557 A1 * | 11/2021 | Jennewein | C12N 1/20 |

FOREIGN PATENT DOCUMENTS

WO  WO-2018077892 A1 *  5/2018  ..... C12Y 207/07013

OTHER PUBLICATIONS

Pathanibul, Production of a Functional Human Milk Oligosaccharide, 2'-Fucosyllactose, Using Microbial Cell Factories, Dissertation, University of Illinois at Urbana—Champaign, 2015. (Year: 2015).*
Uniprot, Accession No. Q58T34, 2017, www.uniprot.org. (Year: 2017).*
Lim, Metabolic engineering of *Saccharomyces cerevisiae* for efficient production of 2'-fucosyllactose, Thesis, University of Illinois, 2017. (Year: 2017).*
Uniprot, Accession No. A0A0P6VBQ4, Feb. 2018, www.uniprot.org. (Year: 2018).*
Katayama et al., Molecular Cloning and Characterization of Bifidobacterium bifidum 1,2--L-Fucosidase (AfcA), J. Bacteriol. 186, 2004, 4885-93. (Year: 2004).*
Liu et al., Functional expression of L-fucokinase/guanosine 5'-diphosphate-L-fucose pyrophosphorylase from Bacteroides fragilis in *Saccharomyces cerevisiae* for the production of nucleotide sugars from exogenous monosaccharides, Glycobiology 21, 2011, 1228-36. (Year: 2011).*
Heredia et al., Specificity of the Constitutive Hexose Transport in Yeast, Eur. J. Biochem. 5 , 1968, 321-29. (Year: 1968).*
International Preliminary Report on Patentability in corresponding PCT application No. PCT/US2019/032474, dated Nov. 26, 2020, 9 pages.

* cited by examiner

*Primary Examiner* — Todd M Epstein
(74) *Attorney, Agent, or Firm* — Lathrop GPM LLP; Lisa Hillman

(57) ABSTRACT

Compositions and methods are provided for producing 2'fucosyliaciose and L-fucose from recombinant microorganisms.

12 Claims, 22 Drawing Sheets
Specification includes a Sequence Listing.

ENGINEERED MICROORGANISMS FOR PRODUCTION OF 2'FUCOSYLLACTOSE AND L-FUCOSE

PRIORITY

This application is a 371 International of PCT Application Number PCT/US19/32474, filed May 15, 2019, which claims the benefit of U.S. Ser. No. 62/671,459, filed on May 15, 2018, which are incorporated by reference herein in their entirety.

BACKGROUND

Human milk oligosaccharides (HMOs) are important components of human milk that promote infant health. Fucosylated oligosaccharides, one of the common HMOs, have been reported to offer health benefits, such as selective enhancement of bifidobacterial growth, and preventing binding of pathogens and toxins to the human gut. In particular, the most abundant fucosylated oligosaccharide in human milk, 2'-fucosyllactose (2-FL), attracted much interest as a functional food ingredient because of its nutraceutical and pharmaceutical properties.

Due to the scarce contents of 2-FL in human milk, it is prohibitively expensive to obtain 2-FL directly from human milk. Production of 2-FL requires α-1,2-fucosyltransferase which transfers the fucosyl residue from guanosine 5'-diphosphate-L-fucose (GDP-L-fucose) into lactose. GDP-L-fucose can be generated through two distinct metabolic pathways: the de novo or salvage pathway. In the de novo pathway, GDP-L-fucose is synthesized from mannose-6-phosphate by GDP-mannose 4,6-dehydratase and GDP-L-fucose synthase. The alternative salvage pathway requires L-fucose as the substrate for producing GDP-L-fucose. This pathway is catalyzed by a bifunctional enzyme, L-fucokinase/GDP-L-fucose phosphorylase (FKP). The salvage pathway was assumed to exist only in eukaryotes until a bacterial FKP was discovered from *Bacteroides fragilis* 9343. While production of 2-FL has been reported in *E. coli*, 2-FL production in engineered yeast via the de novo or salvage pathway has not yet been reported.

L-fucose, a precursor for biosynthesis of GDP-L-fucose in the salvage pathway, can be produced through chemical modifications of other hexose sugars, direct extraction from brown algae hydrolysates, and enzymatic hydrolysis of L-fucose-rich microbial exopolysaccharide (EPS). However, economic and large-scale production of L-fucose is still limited and challenging. Thus, it is not be cost-ineffective to use L-fucose for the large-scale industrial production of 2-FL via the salvage pathway. However, production of L-fucose by engineered *S. cerevisiae* is desirable as the demand of L-fucose is increasing in cosmetics, food products, pharmaceuticals, and biomedical applications.

Figure 1:
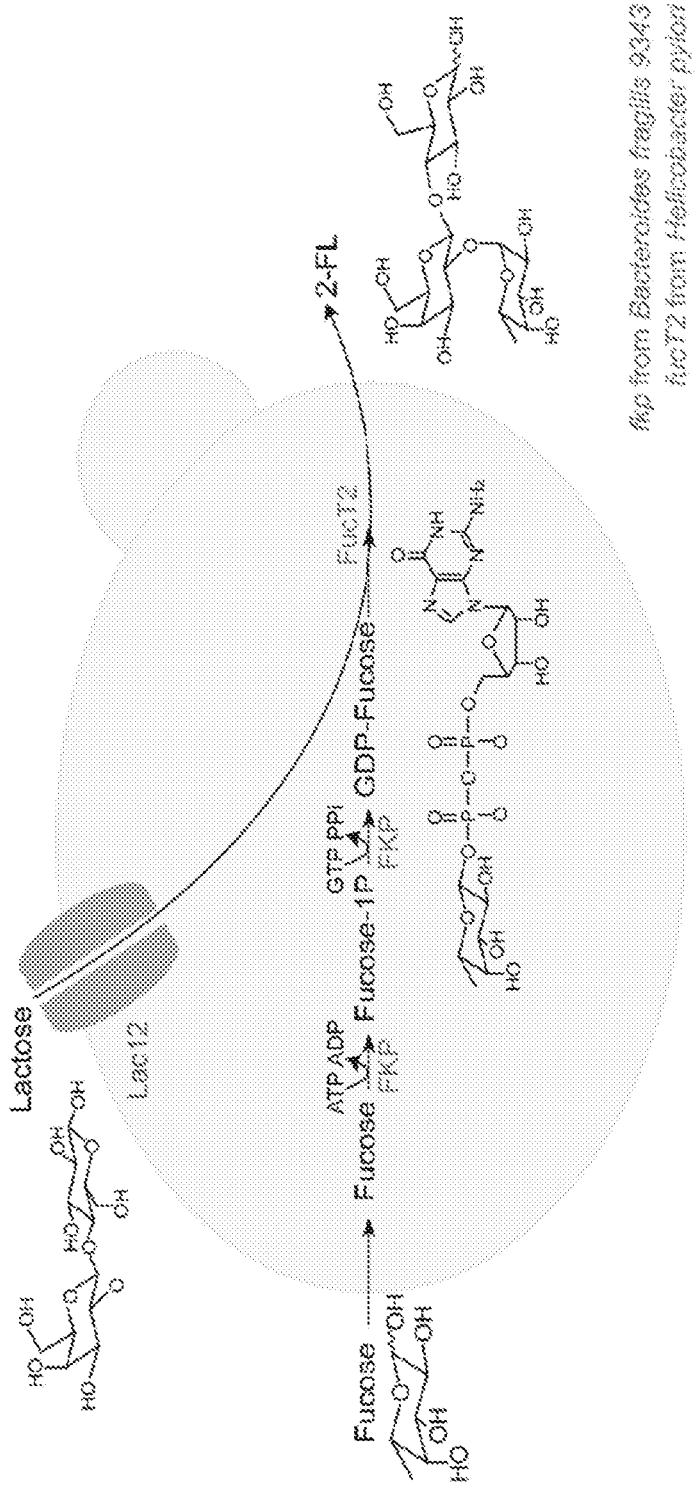
FIG. 1. Schematic representation of 2'-fucosyllactose production in engineered yeast *Saccharomyces cerevisiae*. fkp: the gene coding for L-fucokinase/GDP-L-fucose phosphorylase (FKP); fucT2: the gene coding for α-1,2-fucosyltransferase; and LAC12: the gene coding for lactose permease.

The description of exemplary embodiments in the drawings is not intended to limit the particular forms disclosed, but on the contrary, the intention is to cover all modifications, equivalents and alternatives falling within the spirit and scope of the embodiments.

SUMMARY

An embodiment provides a recombinant yeast cell comprising heterologous nucleic acid molecules encoding the following polypeptides: GDP-mannose 4,6-dehydratase (Gmd), GDP-4-keto-6-deoxymannose 3,5-epimerase 4-reductase (WcaG), an oligosaccharide transporter, and fucosyltransferase, wherein the heterologous nucleic acid molecules are operably linked to at least one expression control nucleic acid molecule. The heterologous nucleic acid molecules can be integrated into a chromosome in the recombinant yeast cell. Two or more copies of heterologous nucleic acid molecules encoding polypeptides GDP-mannose 4,6-dehydratase (Gmd), GDP-4-keto-6-deoxymannose 3,5-epimerase 4-reductase (WcaG), oligosaccharide transporter, and fucosyltransferase can be present in the recombinant yeast cell. The GDP-mannose 4,6-dehydratase (Gmd) polypeptide can have at least 95% identity to SEQ ID NO: 14, the GDP-4-keto-6-deoxymannose 3,5-epimerase 4-reductase (WcaG) polypeptide can have at least 95% identity to SEQ ID NO:15, the oligosaccharide transporter polypeptide can have at least 95% identity to SEQ ID NO:12, and the fucosyltransferase polypeptide can have at least 95% identity to SEQ ID NO: 13. The recombinant yeast cell can be *Saccharomyces cerevisiae, Saccharomyces fermentati, Saccharomyces paradoxus, Saccharomyces uvarum, Saccharomyces bayanus, Schizosaccharomyces pombe, Schizosaccharomyces japonicus, Schizosaccharomyces octosporus, Schizosaccharomyces cryophilus, Torulaspora delbrueckii, Kluyveromyces marxianus, Pichia stipitis, Pichia pastoris, Pichia angusta, Zygosaccharomyces bailii, Brettanomyces intermedius, Brettanomyces bruxellensis, Brettanomyces anomalus, Brettanomyces custersianus, Brettanomyces naardenensis, Brettanomyces nanus, Dek-* kera bruxellensis, Dekkera anomala, Issatchenkia orientalis, Kloeckera apiculate, or Aureobasidium pullulans.

Another embodiment provides a vector or combination of vectors comprising: a nucleic acid molecule encoding GDP-mannose 4,6-dehydratase (Gmd) polypeptide; a nucleic acid molecule encoding GDP-4-keto-6-deoxymannose 3,5-epimerase 4-reductase (WcaG) polypeptide; a nucleic acid molecule encoding oligosaccharide transporter polypeptide; and a nucleic acid molecule encoding fucosyltransferase, wherein the nucleic acid molecules are operably linked to at least one expression control nucleic acid molecule. The vector or combination of vectors can further comprise a polynucleotide encoding a α-L-fucosidase polynucleotide operably linked to at least one expression control nucleic acid molecule.

Yet another embodiment provides a method for production of 2'-fucosyllactose comprising culturing the recombinant yeast cells described herein in a cell culture media in the presence of xylose and lactose, wherein the recombinant yeast cell produces 2'-fucosyllactose. Xylose can be present in the cell culture media at about 10 g/L to about 30 g/L and lactose is present in the cell culture media at about 0.5 g/L to about 2.5 g/L. Cell specific productivity can be from about 0.2 to about 0.5 g 2'-fucosyllactose/g cell. About 50% or more of the 2'-fucosyllactose can be secreted by the recombinant yeast cell into the cell culture media. About 10 g/L or more of 2'-fucosyllactose can be produced. The cell culture medium can be buffered to prevent a decrease in the pH below 3.5.

Still another embodiment provides a recombinant yeast cell as described herein, further comprising a heterologous nucleic acid molecule encoding an α-L-fucosidase polypeptide operably linked to at least one expression control nucleic acid molecule. The α-L-fucosidase polypeptide can have at least 95% identity to SEQ ID NO:16. The recombinant yeast cell can be *Saccharomyces cerevisiae, Saccharomyces fermentati, Saccharomyces paradoxus, Saccharomyces uvarum, Saccharomyces bayanus, Schizosaccharomyces pombe, Schizosaccharomyces japonicus, Schizosaccharomyces octosporus, Schizosaccharomyces cryophilus, Torulaspora delbrueckii, Kluyveromyces marxianus, Pichia stipitis, Pichia pastoris, Pichia angusta, Zygosaccharomyces bailii. Brettanomyces intermedius, Brettanomyces bruxellensis, Brettanomyces anomalus, Brettanomyces custersianus, Brettanomyces naardenensis, Brettanomyces nanus, Dekkera bruxellensis, Dekkera anomala, Issatchenkia orientalis, Kloeckera apiculate*, or *Aureobasidium pullulans*.

Yet another embodiment provides a method for production of L-fucose comprising culturing the recombinant yeast cells described herein in a cell culture media in the presence of glucose and lactose, wherein the recombinant yeast cell produces L-fucose.

An embodiment provides a recombinant yeast cell comprising heterologous nucleic acid molecules encoding a L-fucokinase/GDP-L-fucose phosphorylase (FKP) polypeptide, an oligosaccharide transporter polypeptide, and a fucosyltransferase polypeptide operably linked to at least one expression control nucleic acid molecule. The L-fucokinase/GDP-L-fucose phosphorylase polypeptide can have at least 95% identity to SEQ ID NO: 11, the oligosaccharide transporter polypeptide can have at least 95% identity to SEQ ID NO:12, and the fucosyltransferase polypeptide can have at least 95% identity to SEQ ID NO: 13. The yeast cell can be *Saccharomyces cerevisiae, Saccharomyces fermentati, Saccharomyces paradoxus, Saccharomyces uvarum, Saccharomyces bayanus, Schizosaccharomyces pombe, Schizosaccharomyces japonicus, Schizosaccharomyces octosporus, Schizosaccharomyces cryophilus, Torulaspora delbrueckii, Kluyveromyces marxianus, Pichia stipitis, Pichia pastoris, Pichia angusta, Zygosaccharomyces bailii, Brettanomyces intermedius, Brettanomyces bruxellensis, Brettanomyces anomalus, Brettanomyces custersianus, Brettanomyces naardenensis, Brettanomyces nanus, Dekkera bruxellensis, Dekkera anomala, Issatchenkia orientalis, Kloeckera apiculate*, or *Aureobasidium pullulans*.

Another embodiment provides a vector or combination of vectors comprising: a nucleic acid molecule encoding a L-fucokinase/GDP-L-fucose phosphorylase polypeptide; a nucleic acid molecule encoding an oligosaccharide transporter polypeptide; and a nucleic acid molecule encoding a fucosyltransferase polypeptide, wherein the nucleic acid molecules are operably linked to at least one expression control nucleic acid molecule.

Still another embodiment provides a method for production of 2'-fucosyllactose comprising culturing the recombinant yeast cells described herein in a cell culture media in the presence of L-fucose and lactose, wherein the recombinant yeast cell produces 2'-fucosyllactose.

Advantageously, the compositions and methods avoid possible endotoxin contamination in the produced 2-FL, and bacteriophage infection in the fermentation process, which can occur where 2-FL is produced in bacteria such as *E. coli*. Certain yeast, such as *Saccharomyces cerevisiae*, are generally recognized as safe (GRAS) microorganisms and have been used in food and pharmaceutical industries.

DETAILED DESCRIPTION

Methods and compositions now will be described more fully hereinafter with reference to the accompanying drawings, in which some, but not all embodiments of the methods and compositions are shown. Indeed, the methods and compositions can be embodied in many different forms and should not be construed as limited to the embodiments set forth herein; rather, these embodiments are provided so that this disclosure will satisfy applicable legal requirements.

Likewise, many modifications and other embodiments of the methods and compositions described herein will come to mind to one of skill in the art to which the methods and compositions pertain having the benefit of the teachings presented in the foregoing descriptions and the associated drawings. Therefore, it is to be understood that the methods and compositions are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the systems and methods pertain.

As used herein, the term "and/or" includes any and all combinations of one or more of the associated listed items. As used herein, the singular forms "a," "an," and "the" are intended to include the plural forms as well as the singular forms, unless the context clearly indicates otherwise.

The embodiments illustratively described herein suitably can be practiced in the absence of any element or elements, limitation or limitations that are not specifically disclosed herein. Thus, for example, in each instance herein any of the terms "comprising." "consisting essentially of," and "consisting of" may be replaced with either of the other two terms, while retaining their ordinary meanings.

The term "about" in association with a numerical value means that the numerical value can vary plus or minus by 5% or less of the numerical value. All patents, patent applications, and other scientific or technical writings referred to anywhere herein are incorporated by reference herein in their entirety.

Methods are provided to produce 2-FL in engineered microorganisms, such as yeast via the salvage pathway using L-fucose and lactose as substrates, by making certain genetic modifications (FIG. 1). First, FKP can be introduced to produce intracellular GDP-L-fucose as a substrate of fucosyltransferase. Intracellular GDP-L-fucose level has been considered as a bottleneck in 2-FL production. Second, lactose, a fucose acceptor in 2-FL production, is transported into the cytosol of cells. Lactose permease, such as Lac12 from *Kluyveromyces* lactics or CDT-1 from *Neurospora crassa* can be introduced into cells for transporting lactose into the cytosol. Certain microorganisms such as wild-type *S. cerevisiae* are incapable of transporting lactose into the cytosol. Finally, α-1,2-fucosyltransferase, which catalyzes fucosylation of lactose into 2-FL using GDP-L-fucose can be introduced into cells. Several α-1,2-fucosyltransferases can be used to facilitate the synthesis of 2-FL, including, e.g., FucT2 from *Helicobacter pylori*, WcfB from *B. fragilis* 9343, and WbgL from *E. coli* 0126.

Figure 7:
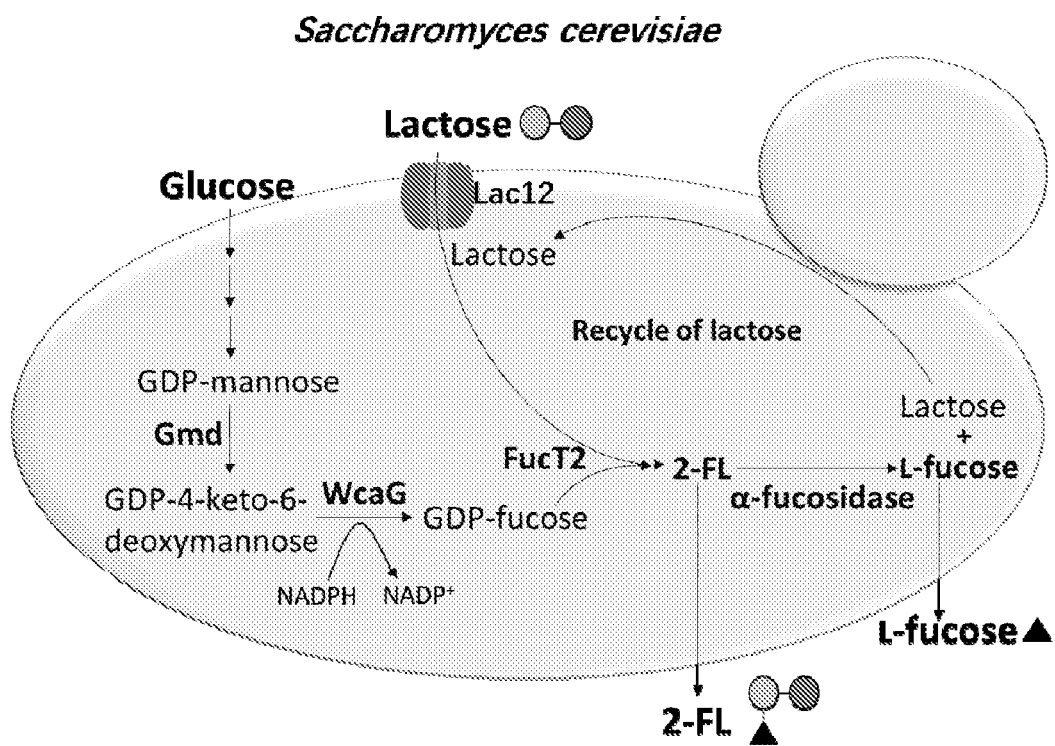
FIG. 7. Schematic diagram of 2-FL and L-fucose production in engineered *S. cerevisiae*. Lac12, lactose permease; Gmd, GDP-mannose 4,6-dehydratase; WcaG, GDP-4-keto-6-deoxymannose 3,5-epimerase 4-reductase; FucT2, alpha-1,2-fucosyltransferase; α-fucosidase, α-L-fucosidase; 2-FL, 2'-fucosyllactose.

Additionally provided are microorganisms, such as yeast, capable of producing 2-FL and L-fucose through the de novo pathway and utilizing glucose and lactose. Three genetic perturbations can be made to enable 2-FL synthesis in microorganisms such as yeast (FIG. 7). First, a lactose transporter (Lac12) from e.g., *K. lactis* is integrated into cells. Second, Gmd and WcaG from, e.g., *E. coli* K-12 are over-expressed in recombinant microorganism to empower in vivo GDP-L-fucose production through de novo pathway. Third, α-1,2-fucosyltransferase (e.g., FucT2 from H. pylon) is expressed in recombinant cells to transfer fucose unit from GDP-L-fucose to lactose. The result is the production of 2-FL in the resulting engineered microorganism. Furthermore, L-fucose production can be accomplished by additional expression of α-L-fucosidase from, e.g., X. manihotis in the 2-FL producing strain. 2-FL and L-fucose can be produced by recombinant microorganisms via de novo pathway.

Overexpression of a polynucleotide, gene, or protein means that the polynucleotide, gene, or protein is expressed using a heterologous promoter that is known to be strong and constitutive. If the target polynucleotide or gene is an endogenous polynucleotide or gene, overexpression means that the amount of protein or mRNA is much higher than those without the overexpression cassette. If the target gene is a heterologous gene, any level of the protein or mRNA can be considered as overexpressed. In an example, a GPD promoter can be used to overexpress a polypeptide in a yeast cell. See Christianson TW, Sikorski RS, Dante M, Shero JH, Hieter P. Multifunctional yeast high-copy-number shuttle vectors. Gene 1992,110:119-22. Other promoters as known to those of skill in the art can also be used.

L-fucokinase/GDP-L-fucose phosphorylase (FKP)

Figure 12:
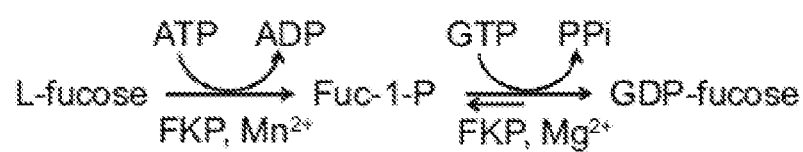
FIG. 12 shows the pathway to produce GDP-fucose.

L-fucokinase/GDP-L-fucose phosphorylase (FKP) (also known as bifunctional fucokinase/L-fucose-1-P-guanylyltransferase) can catalyze the formation of fucose-1-phosphate from fucose, with ATP consumption. FKP can then use fucose-1-phosphate and GTP to synthesize GDP-fucose Therefore, FKP can convert L-fucose into GDP-fucose via a fucose-1-phosphate (Fuc-1-P) intermediate (FIG. 12). A FKP nucleic acid molecule encodes an FKP polypeptide that is effective to convert L-fucose to GDP-fucose through a fucose-1-phosphate (Fuc-1-P) intermediate.

In an embodiment, a FKP polypeptide comprises SEQ ID NO:11, which is GenBank Accession number Q58T34, from *Bacteroides fragilis*. In an embodiment, a FKP polypeptide has about 80, 85, 90, 95, 96, 97, 98, 99, or 99.5 or more homology to SEQ ID NO:11, and has activity to convert L-fucose into GDP-fucose via a fucose-1-phosphate (Fuc-1-P) intermediate.

SEQ ID NO: 11

MQKLLSLPSNLVQSFHELERVNRTDWFCTSDPVGKKLGSGGGTSWLLEEC

YNEYSDGATFGEWLEKEKRILLHAGGQSRRLPGYAPSGKILTPVPVERWE

RGQHLGQNLLSLQLPLYEKIMSLAPDKLHTLIASGDVYIRSEKPLQSIPE

ADVVCYGLWVDPSLATHHGVFASDRKHPEQLDFMLQKPSLAELESLSKTH

LFLMDIGIWLLSDRAVEILMKRSHKESSEELKYYDLYSDFGLALGTHPRI

EDEEVNTLSVAILPLPGGEFYHYGTSKELISSTLSVQNKVYDQRRIMHRK

VKPNPAMFVQNAVVRIPLCAENADLWIENSHIGPKWKIASRHIITGVPEN

DWSLAVPAGVCVDVVPMGDKGFVARPYGLDDVEKGDLRDSKTTLTGIPFG

EWMSKRGLSYTDLKGRTDDLQAVSVFPMVNSVEELGLVLRWMLSEPELEE

GKNIWLRSEHFSADEISAGANLKRLYAQREEFRKGNWKALAVNHEKSVFY

QLDLADAAEDFVRLGLDMPELLPEDALQMSRIHNRMLRARILKLDGKDYR

PEEQAAFDLLRDGLLDGISNRKSTPKLDVYSDQIVWGRSPVRIDMAGGWT

DTPPYSLYSGGNVVNLAIELNGQPPLQVYVKPCKDFHIVLRSIDMGAMEI

VSTFDELQDYKKIGSPFSIPKAALSLAGFAPAFSAVSYASLEEQLKDFGA

GIEVTLLAAIPAGSGIGTSSILASTVLGAINDECGLAWDKNEICQRTLVL

EQLLTTGGGWQDQYGGVLQGVKLLQTEAGFAQSPLVRWLPDHLFTHPEYK

DCHLLYYTGITRTAKGILAEIVSSMELNSSLHLNLLSEMKAHALDMNEAI

QRGSFVEFGRLVGKTWEQNKALDSGTNPPAVEAIIDLIKDYTLGYKLPGA

GGGGYLYMVAKDPQAAVRIRKILTENAPNPRARFVEMTLSDKGFQVSRS

Other FKP polypeptides that can be used include, for example, GenBank numbers WP_005803741.1, WP_032580039, WP_129659572.1, WP_122133642.1, WP_005820511.1, EYA24252.1, WP_122330657.1, WP_032536697.1, WP_044300229.1, WP_071146621.1, CDC89499.1, WP_109115632.1, WP_024988153.1, WP_121767139.1, and WP_065539361.1. Other FKP polypeptides can also be used.

Oligosaccharide Transporters

In an embodiment a microorganism comprises a recombinant nucleic acid molecule that encodes an oligosaccharide transporter, such as a lactose permease. Lactose permease (Lac12) is an inducible lactose permease that mediates the transport of lactose into a cell. Certain yeasts are incapable of transporting lactose into the cytosol. An oligosaccharide transporter nucleic acid molecule encodes an oligosaccharide transporter polypeptide that is effective to transport lactose into a cell.

An oligosaccharide transporter, such as Lac12 from *Kluyveromyces* lactics or CDT-1 from *Neurospora crassa*, can be to be introduced into a microorganism such as yeast for transporting lactose into the cytosol. In an embodiment, a Lac12 polypeptide comprises SEQ ID NO:12, which is GenBank Accession number P07921, from *Kluyveromyces* lactis. In an embodiment, an oligosaccharide transporter polypeptide has about 80, 85, 90, 95, 96, 97, 98, 99, or 99.5 or more homology to SEQ ID NO: 12, and is effective to transport lactose into a cell.

```
                                             SEQ ID NO: 12
MADHSSSSSSLQKKPINTIEHKDTLGNDRDHKEALNSDNDNTSGLKINGV

PIEDAREEVLLPGYLSKQYYKLYGLCFITYLCATMQGYDGALMGSIYTED

AYLKYYHLDINSSSGTGLVFSIFNVGQICGAFFVPLMDWKGRKPAILIGC

LGVVIGAIISSLTTTKSALIGGRWFVAFFATIANAAAPTYCAEVAPAHLR

GKVAGLYNTLWSVGSIVAAFSTYGTNKNEPNSSKAFKIPLYLQMMFPGLV

CIFGWLIPESPRWLVGVGREEEAREFIIKYHLNGDRTHPLLDMEMAEIIE

SFHGTDLSNPLEMLDVRSLFRTRSDRYRAMLVILMAWFGQFSGNNVCSYY

LPTMLRNVGMKSVSLNVLMNGVYSIVTWISSICGAFFIDKIGRREGELGS

ISGAALALTGLSICTARYEKTKKKSASNGALVFIYLFGGIFSFAFTPMQS

MYSTEVSTNLTRSKAQLLNFVVSGVAQFVNQFATPKAMKNIKYWFYVFYV

FFDIFEFIVIYFFFVETKGRSLEELEVVFEAPNPRKASVDQAFLAQVRAT

LVQRNDVRVANAQNLKEQEPLKSDADHVEKLSEAESV
```

Other lactose permease polypeptides include, for example, GenBank accession numbers SIT60471.1, XP_022675158.1, SIT60474.1, SIT60468.1, and SIT60472.1. Other lactose permease polypeptides can be used. Additionally, other oligosaccharide transporter polypeptides can be used. Examples include mutated CDT-1M from *Neurospora crassa*, CDT-2 from *Neurospora crassa*, mutated CDT-2M from *Neurospora crassa*, HXT2.4 (wild type) from Scheffersomyces stipites, HXT2.4D from Scheffersomyces stipites, HXT2.4L from Scheffersomyces stipites, HXT2.1 from Scheffersomyces stipites, HXT2.3 from Scheffersomyces stipites, HXT2.5 from Scheffersomyces stipites, HXT2.6 from Scheffersomyces stipites, LAC1 from Scheffersomyces stipites, LAC2 from Scheffersomyces stipites, and LAC3 from Scheffersomyces stipites. See example 18 for amino acid sequences. In an embodiment an oligosaccharide transporter polypeptide has about 80, 85, 90, 95, 96, 97, 98, 99, or 99.5 or more homology to each of the oligosaccharide transporter polypeptides described herein.

Fucosyltransferase

α-1,2-fucosyltransferase, which catalyzes fucosylation of lactose into 2-FL using GDP-L-fucose, can be introduced into a microorganism such as yeast. Many fucosyltransferases have been verified to facilitate the synthesis of 2-FL, which includes FucT2 from *Helicobacter pylori*, WcfB from *B. fragilis* 9343, and WbgL from *E. coli* 0126. In other embodiments a α-1,2-fucosyltransferase polynucleotide is a *Helicobacter pylori, Caenorhabditis elegans, Rattus norvegicus, Mus musculus*, or Homo sapien polynucleotide A fucosyltransferase nucleic acid molecule encodes a fucosyltransferase polypeptide that is effective to catalyze fucosylation of lactose into 2-FL using GDP-L-fucose.

In an embodiment, a fucosyltransferase polypeptide comprises SEQ ID NO:13, which is GenBank Accession number AAC99764.1, from *Helicobacter pylori*. In an embodiment, a fucosyltransferase polypeptide has about 80, 85, 90, 95, 96, 97, 98, 99, or 99.5 or more homology to SEQ ID NO: 13, and can catalyzes fucosylation of lactose into 2-FL using GDP-L-fucose a cell.

```
                                             SEQ ID NO: 13
MAFKVVQICGGLGNQMFQYAFAKSLQKHLNTPVILDTTSFDWSNRKMQLE

LFPIDLPYANAKEIAIAKMQHLPKLVRDALKYIGFDRVSQEIVFEYEPKL

LKPSRLTYFFGYFQDPRYFDAISSLIKQTFTLPPPPENNKNNNKKEEEYQ

RKLSLILAAKNSVFVHIRRGDYVGIGCQLGIDYQKKALEYMAKRVPNMEL

FVFCEDLKFTQNLDLGYPFTDMTTRDKEEEAYWDMLLMQSCKHGIIANST

YSWWAAYLMENPEKIIIGPKHWLFGHENILCKEWVKIESHFEVKSQKYNA.
```

Other fucosyltransferase polypeptides include, for example, GenBank accession numbers WP_000874818.1, WP_128004774.1, WP_097716330.1, WP_000874787.1, WP_120821635.1, WP_120957849.1, WP_128010550.1, WP_123958006.1, WP_120913327.1, WP_127994228.1, WP_120831210.1, WP_115806174.1, WP_128028147.1, WP_021174400.1, WP_089086505.1. Other fucosyltrasferase polypeptides can also be used.

GDP-mannose 4,6-dehydratase (Gmd)

GDP-mannose 4,6-dehydratase can catalyze the conversion of GDP-mannose into GDP-4-dehydro-6-deoxy-D-mannose and water. A Gmd nucleic acid molecule encodes a Gmd polypeptide that is effective to convert GDP-mannose to GDP-4-dehydro-6-deoxy-D-mannose in a cell.

In an embodiment, a Gmd polypeptide comprises SEQ ID NO:14, which is GenBank Accession number NP_416557.1, from *Escherichia coli*. In an embodiment, a Gmd polypeptide has about 80, 85, 90, 95, 96, 97, 98, 99, or 99.5 or more homology to SEQ ID NO:14, and can convert GDP-mannose to GDP-4-dehydro-6-deoxy-D-mannose.

```
                                             SEQ ID NO: 14
MSKVALITGV TGQDGSYLAE FLLEKGYEVH GIKRRASSFN

TERVDHIYQD PHTCNPKFHL HYGDLSDTSN LTRILREVQP

DEVYNLGAMS HVAVSFESPE YTADVDAMGT LRLLEAIRFL

GLEKKTRFYQ ASTSELYGLV QEIPQKETTP FYPRSPYAVA

KLYAYWITVN YRESYGMYAC NGILFNHESP RRGETFVTRK

ITRAIANIAQ GLESCLYLGN MDSLRDWGHA KDYVKMQWMM

LQQEQPEDFV IATGVQYSVR QFVEMAAAQL GIKLRFEGTG

VEEKGIVVSV TGHDAPGVKP GDVIIAVDPR YFRPAEVETL

LGDPTKAHEK LGWKPEITLR EMVSEMVAND LEAAKKHSLL

KSHGYDVAIA LES.
```

Other Gmd polypeptides include, for example, GenBank accession numbers WP_097447618.1, WP_115723960.1, WP_104722871.1, WP_112362095.1, WP_096248093.1, WP_052983460.1 and UniParc Q56598-1. Other Gmd polypeptides can also be used.

GDP-4-keto-6-deoxymannose 3,5-epimerase 4-reductase (WcaG)

GDP-4-keto-6-deoxymannose 3,5-epimerase 4-reductase (WcaG) (also known as GDP-L-fucose synthase) catalyzes the conversion of GDP-4-dehydro-6-deoxy-D-mannose, NADPH, and $H^+$ to GDP-L-fucose and $NADP^+$. A WcaG nucleic acid molecule encodes a WcaG polypeptide that is effective to convert GDP-4-dehydro-6-deoxy-D-mannose to GDP-L-fucose in a cell.

In an embodiment, a WcaG polypeptide comprises SEQ ID NO:15, which is GenBank Accession number AHG09445.1, from *Escherichia coli*. In an embodiment, a WcaG polypeptide has about 80, 85, 90, 95, 96, 97, 98, 99, or 99.5 or more homology to SEQ ID NO:15, and can convert GDP-4-dehydro-6-deoxy-D-mannose to GDP-L-fucose.

```
                                            SEQ ID NO: 15
MSKQRIFIAG  HRGMVGSAIR  RQLEQRGDVE  LVLRTRDELN

LLDSRAVHDF  FASERIDQVY  LAAAKVGGIV  ANNTYPADFI

YQNMMIESNI  IHAAHQNDVN  KLLFLGSSCI  YPKLAKQPMA

ESELLQGTLE  PTNEPYAIAK  IAGIKLCESY  NRQYGRDYRS

VMPTNLYGPH  DNFHPSNSHV  IPALLRRFHE  ATAQNAPDVV

VWGSGTPMRE  FLHVDDMVAA  SIHVMELAHE  VWLENTQPML

SHINVGTGVD  CTIRELAQTI  AKVVGYKGRV  VFDASKPDGT

PRKLLDVTRL  HQLGWYHEIS  LEAGLASTYQ  WFLENQDRER G
```

Other Gmd polypeptides include, for example, GenBank accession numbers WP_054427662.1, WP_097329811.1, WP_112919485.1, and Uniparc A0A376US02-1. Other Gmd polypeptides can also be used.

α-L-Fucosidase

Alpha-L-fucosidase catalyzes the conversion of alpha-L-fucoside and water to L-fucose and an alcohol. An alpha-L-fucosidase nucleic acid molecule encodes an alpha-L-fucosidase polypeptide that is effective to convert alpha-L-fucoside to L-fucose and an alcohol.

In an embodiment, an α-L-fucosidase polypeptide comprises SEQ ID NO: 16, which is GenBank Accession number KPL47506.1, from *Xanthomonas axonopodis*. In an embodiment, an α-L-fucosidase polypeptide has about 80, 85, 90, 95, 96, 97, 98, 99, or 99.5 or more homology to SEQ ID NO:16, and can convert alpha-L-fucoside to alpha-L-fucosidase.

```
                                            SEQ ID NO: 16
MTTDSRQYAA  PSRRHAGAAP  RSRMLAFALL  LALPALHVTA

AQSPTAPTAT  TLSPEAIDQQ  WLDATAKYAP  ERERLVREAE

AGARKGPFRP  DWAALKAYQS  PAWYDNAKFG  IFIHWGVFSV

PAFGSEWYSR  NMYLQGSKEF  AHHVATYGPQ  ASSGYKDLIP

KFTAPRFDPN  GWAKLFRESG  ARYVVPVAEH  HDGFALYDSK

LSDWTAMKMG  PKRDLLGELS  KAIRAQGLHF  GLSSHRAEHN

WFFDGGRTFD  SDVNDPRYAA  LYGPAQVRLP  GKDDADVAND

WTPVSQAWLD  DWLARTTELI  DTYQPDLIYE  DWWIAHPTFR

RSLPTMLAYY  YNQGAARTEA  DRGVVVNYKL  GAFPEGAGTL

DIERGQLTGI  HSTHWQTDTS  VSNASWGYIE  NDTYKSPTFI

IHMLADVVAK  NGNLMLNIGP  RADGSIPGTE  RGILLAIGKW

LKTNGCAIYD  SKPWRVYGEG  PTEVVGGTFQ  DIKTKPYTAE

DFRFTTRDGA  LYAIELGWPS  NGEAVIRSLK  AADGVRAVTL

LATGKKIPFE  QRADGLHLRL  PVKPVGASAY  VFRIDLSSPT P
```

Other α-L-fucosidase polypeptides include, for example, GenBank accession numbers WP_127167340.1, WP_122272478.1, WP_039441974.1, WP_078590238.1, WP_042823238.1, WP_089504431.1, OQP75960.1 WP_015472472.1, WP_059030003.1, and WP_040267501.1. Other α-L-fucosidase polypeptides can also be used.

Recombinant Microorganisms

A recombinant, transgenic, or genetically engineered microorganism is a microorganism, e.g., bacteria, fungus, or yeast that has been genetically modified from its native state. Thus, a "recombinant yeast" or "recombinant yeast cell" refers to a yeast cell that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast or yeast cell, or on a plasmid in the yeast or yeast cell. Recombinant cells disclosed herein can comprise exogenous polynucleotides on plasmids. Alternatively, recombinant cells can comprise exogenous polynucleotides stably incorporated into their chromosome. In an embodiment a recombinant yeast or recombinant yeast cell comprises one or more (e.g., 1, 2, 3, 4, 5, 6 or more) heterologous nucleic acid molecules, which can express one or more heterologous polypeptides.

A heterologous or exogenous polypeptide or polynucleotide refers to any polynucleotide or polypeptide that does not naturally occur or that is not present in the starting target microorganism. For example, a polynucleotide from a bacteria that is transformed into a yeast cell that does naturally or otherwise comprise the bacterial polynucleotide is a heterologous or exogenous polynucleotide. A heterologous or exogenous polypeptide or polynucleotide can be a wild-type, synthetic, or mutated polypeptide or polynucleotide. In an embodiment, a heterologous or exogenous polypeptide or polynucleotide is not naturally present in a starting target microorganism and is from a different genus or species than the starting target microorganism.

A homologous or endogenous polypeptide or polynucleotide refers to any polynucleotide or polypeptide that naturally occurs or that is otherwise present in a starting target microorganism. For example, a polynucleotide that is naturally present in a yeast cell is a homologous or endogenous polynucleotide. In an embodiment, a homologous or endogenous polypeptide or polynucleotide is naturally present in a starting target microorganism.

A recombinant microorganism can comprise one or more polynucleotides not present in a corresponding wild-type cell, wherein the polynucleotides have been introduced into that microorganism using recombinant DNA techniques, or which polynucleotides are not present in a wild-type microorganism and is the result of one or more mutations.

A genetically modified or recombinant microorganism can be, for example, a yeast such as Saccharomycesceae, e.g., *Saccharomyces cerevisiae, Saccharomyces cerevisiae* strain KAM-2 (Matα ura3), *Saccharomyces pastorianus, Saccharomyces beticus, Saccharomyces fermentati, Saccharomyces paradoxus, Saccharomyces uvarum* and *Saccharomyces bayanus*; *Schizosaccharomyces* such as *Schizosaccharomyces pombe, Schizosaccharomyces japonicus, Schizosaccharomyces octosporus* and *Schizosaccharomyces cryophilus*; *Torulaspora* such as *Torulaspora delbrueckii*; *Kluyveromyces* such as *Kluyveromyces marxianus*; *Pichia* such as *Pichia stipitis, Pichia pastoris, Pichia angusta, Zygosaccharomyces* such as *Zygosaccharomyces bailii*; *Brettanomyces* such as *Brettanomyces intermedius, Brettanomyces bruxellensis, Brettanomyces anomalus, Brettanomyces custersianus, Brettanomyces naardenensis, Brettano-

*myces nanus, Dekkera bruxellensis* and *Dekkera anomala; Metschmkowia, Issatchenkia*, such as *Issatchenkia orientalis, Kloeckera* such as *Kloeckera apiculate*, or *Aureobasidium* such as *Aureobasidium pullulans*.

In one embodiment a genetically engineered, recombinant, or transgenic microorganism comprises one or more heterologous or exogenous polynucleotides, optionally operably linked to one or more heterologous, exogenous, or endogenous regulatory elements such that one or more heterologous or exogenous biologically active polypeptides are expressed by the microorganism. A genetically engineered microorganism can comprise heterologous polynucleotides encoding L-fucokinase/GDP-L-fucose phosphorylase polypeptide, an oligosaccharide transporter, such as a lactose permease polypeptide, and fucosyltransferase. Additionally, a genetically engineered microorganism can comprise heterologous polynucleotides encoding GDP-mannose 4,6-dehydratase (Gmd), GDP-4-keto-6-deoxymannose 3,5-epimerase 4-reductase (WcaG), oligosaccharide transporter, and fucosyltransferase. Furthermore, a genetically engineered microorganism can comprise heterologous polynucleotides encoding GDP-mannose 4,6-dehydratase (Gmd), GDP-4-keto-6-deoxymannose 3,5-epimerase 4-reductase (WcaG), oligosaccharide transporter, fucosyltransferase, and α-L-fucosidase.

A recombinant nucleic acid can be operably linked to one or more expression control sequences that express or overexpress the polypeptide.

In an embodiment, a recombinant microorganism comprises an operative metabolic pathway for producing 2'-fucosyllactose from xylose and lactose. The recombinant microorganism can express: a heterologous GDP-mannose 4,6-dehydratase (Gmd), a heterologous GDP-4-keto-6-deoxymannose 3,5-epimerase 4-reductase (WcaG), a heterologous oligosaccharide transporter, and a heterologous fucosyltransferase for conversion of xylose and lactose to 2'fucosyllactose.

In an embodiment, a recombinant microorganism comprises an operative metabolic pathway for producing 2'-fucosyllactose from L-fucose and lactose. The recombinant microorganism can express: a) a heterologous L-fucokinase/GDP-L-fucose phosphorylase polypeptide; b) a heterologous oligosaccharide transporter polypeptide and c) a heterologous fucosyltransferase polypeptide for conversion of L-fucose and lactose to 2'fucosyllactose.

In another embodiment, a recombinant microorganism comprises an operative metabolic pathway for producing 2'-fucosyllactose from glucose and lactose. The recombinant microorganism can express: a) a heterologous GDP-mannose 4,6-dehydratase (Gmd) polypeptide; b) a heterologous GDP-4-keto-6-deoxymannose 3.5-epimerase 4-reductase polypeptide (WcaG); c) a heterologous oligosaccharide transporter polypeptide; and d) a heterologous fucosyltransferase polypeptide for conversion of L-fucose and lactose to 2'fucosyllactose.

In another embodiment, a recombinant microorganism comprises an operative metabolic pathway for producing L-fucose from glucose and lactose. The recombinant microorganism can express: a) a heterologous GDP-mannose 4,6-dehydratase (Gmd) polypeptide; b) a heterologous GDP-4-keto-6-deoxymannose 3,5-epimerase 4-reductase polypeptide (WcaG); c) a heterologous oligosaccharide transporter polypeptide; d) a heterologous fucosyltransferase polypeptide for conversion of L-fucose and lactose to 2'fucosyllactose; and e) a heterologous α-L-fucosidase polypeptide for conversion of glucose and lactose to L-fucose.

In an embodiment a heterologous L-fucokinase/GDP-L-fucose phosphorylase polypeptide has at least about 80, 85, 90, 95, 98, 99, or 100% sequence identity to SEQ ID NO:11, a heterologous oligosaccharide transporter polypeptide has at least about 80, 85, 90, 95, 98, 99, or 100% sequence identity to SEQ ID NO:12, a fucosyltransferase polypeptide has at least about 80, 85, 90, 95, 98, 99, or 100% sequence identity to SEQ ID NO:13, a heterologous L-GDP-mannose 4,6-dehydratase (Gmd) polypeptide has at least about 80, 85, 90, 95, 98, 99, or 100% sequence identity to SEQ ID NO:14, a heterologous GDP-4-keto-6-deoxymannose 3,5-epimerase 4-reductase (WcaG) polypeptide has at least about 80, 85, 90, 95, 98, 99, or 100% sequence identity to SEQ ID NO: 15 and a heterologous α-L-fucosidase polypeptide has at least about 80, 85, 90, 95, 98, 99, or 100% sequence identity to SEQ ID NO: 16.

Polynucleotides and Genes

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragment thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene comprise regulatory elements and coding sequences that are derived from different sources, or regulatory elements and coding sequences that are derived from the same source, but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., L-fucokinase/GDP-L-fucose phosphorylase, GDP-mannose 4,6-dehydratase (Gmd). GDP-4-keto-6-deoxymannose 3,5-epimerase 4-reductase (WcaG), oligosaccharide transporter, and fucosyltransferase, and a α-L-fucosidase.

Polynucleotides can comprise other nucleic acid molecules, such as molecules coding for linkers, signal sequences, TMR stop transfer sequences, transmembrane domains, or ligands useful in protein purification such as glutathione-S-transferase, histidine tag, and Staphylococcal protein A.

Polynucleotides can be codon optimized for expression in yeast. See, e.g., www.genscript.com/tools/codon-frequency-table.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide nucleic acid molecules encoding polypeptides described herein, as well as homologous nucleic acid molecules that are at least about 80, or about 85, 90, 91, 92, 93, 94, 95, 96, 97, 98, 99% or more identical to polynucleotides described herein and the complements thereof are also polynucleotides. Degenerate nucleotide nucleic acid molecules are polynucleotides that encode a polypeptide described herein or fragments thereof, but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid molecules present in, for example, a microorganism such as a yeast or bacterium. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise coding sequences for naturally occurring polypeptides or can encode altered sequences that do not occur in nature.

Unless otherwise indicated, the term polynucleotide or gene includes reference to the specified sequence as well as the complementary sequence thereof.

The expression products of genes or polynucleotides are often proteins, or polypeptides, but in non-protein coding genes such as rRNA genes or tRNA genes, the product is a functional RNA. The process of gene expression is used by all known life forms, i.e., eukaryotes (including multicellular organisms), prokaryotes (bacteria and archaea), and viruses, to generate the macromolecular machinery for life. Several steps in the gene expression process can be modulated, including the transcription, up-regulation, RNA splicing, translation, and post-translational modification of a protein.

Polypeptides

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

A mutated protein or polypeptide comprises at least one deleted, inserted, and/or substituted amino acid, which can be accomplished via mutagenesis of polynucleotides encoding these amino acids. Mutagenesis includes well-known methods in the art, and includes, for example, site-directed mutagenesis by means of PCR or via oligonucleotide-mediated mutagenesis as described in Sambrook et al., Molecular Cloning-A Laboratory Manual, 4th ed., Vol. 1-4 (2012).

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar variants will be sufficiently similar to the amino acid sequence of the polypeptides described herein. Such variants generally retain the same or similar functional activity (about 85, 90, 95, 100, 105, 110, or 115%) of the polypeptides described herein. Variants include peptides that differ in amino acid sequence from the native and wild-type peptide, respectively, by way of one or more amino acid deletion(s), addition(s), and/or substitution(s). These may be naturally occurring variants as well as artificially designed ones.

As used herein, the term "percent (%) sequence identity" or "percent (%) identity," also including "homology," is defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

Polypeptides and polynucleotides that are sufficiently similar to polypeptides and polynucleotides described herein (e.g., L-fucokinase/GDP-L-fucose phosphorylase (FKP) GDP-mannose 4,6-dehydratase (Gmd), GDP-4-keto-6-deoxymannose 3,5-epimerase 4-reductase (WcaG), oligosaccharide transporter, and fucosyltransferase, α-L-fucosidase and mutants or variants thereof) can be used herein. Polypeptides and polynucleotides that have about 85, 90, 95, 96, 97, 98, 99% or more homology or identity to polypeptides and polynucleotides described herein (e.g., L-fucokinase/GDP-L-fucose phosphorylase (FKP), GDP-mannose 4,6-dehydratase (Gmd), GDP-4-keto-6-deoxymannose 3,5-epimerase 4-reductase (WcaG), oligosaccharide transporter, and fucosyltransferase, α-L-fucosidase can be used herein.

Constructs and Cassettes

An expression control nucleic acid molecule is a nucleic acid molecule that allows for the expression of polynucleotide molecules into polypeptides, as discussed below. A recombinant construct is a polynucleotide having heterologous polynucleotide elements. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence as well.

An "expression cassette" refers to a fragment of DNA comprising a coding sequence of a selected gene (e.g., L-fucokinase/GDP-L-fucose phosphorylase (FKP), GDP-mannose 4,6-dehydratase (Gmd), GDP-4-keto-6-deoxymannose 3,5-epimerase 4-reductase (WcaG), oligosaccharide transporter, fucosyltransferase, and/or α-L-fucosidase) and regulatory elements preceding (5' non-coding sequences) and/or following (3' non-coding sequences) the coding sequence that are required for expression of the selected gene product. Thus, an expression cassette can be composed of, for example: 1) a promoter sequence; 2) one or more coding sequences ("ORFs"); and, 3) a 3' untranslated region (i.e., a terminator) that, in eukaryotes, usually contains a polyadenylation site. The expression cassette is usually included within a vector, to facilitate cloning and transformation. Different expression cassettes can be transformed into different organisms including bacteria, yeast, plants and mammalian cells, as long as the correct regulatory elements are used for each host.

A recombinant construct or expression cassette can be contained within a vector. In addition to the components of the recombinant construct, the vector can include, e.g., one or more selectable markers, a signal that allows the vector to exist as single-stranded DNA (e.g., a M13 origin of replication), at least one multiple cloning site, and a origin of replication (e.g., a SV40 or adenovirus origin of replication).

Generally, a polynucleotide or gene that is introduced into a genetically engineered microorganism is part of a recombinant construct. A polynucleotide can comprise a gene of interest, e.g., a coding sequence for a protein, or can be a nucleic acid molecule that is capable of regulating expression of a gene, such as a regulatory element, an antisense sequence, a sense suppression sequence, or a miRNA sequence. A recombinant construct can include, for example, regulatory elements operably linked 5' or 3' to a polynucleotide encoding one or more polypeptides of interest. For example, a promoter can be operably linked with a polynucleotide encoding one or more polypeptides of interest when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, and translational termination regions) and/or the polynucleotide encoding a signal anchor can be native/analogous to the host cell or to each other. Alternatively, the regulatory elements can be heterologous to the host cell or to each other. See, U.S. Pat. No. 7,205,453 and U.S. Patent Application Publication Nos. 2006/0218670 and 2006/0248616. The expression cassette or recombinant construct can additionally contain one or more selectable marker genes.

Methods for preparing polynucleotides operably linked to expression control sequences and/or regulatory elements and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

A promoter is a nucleic acid molecule that is capable of controlling the expression of a coding sequence or gene. Promoters are generally located 5' of the sequence that they regulate. Promoters can be derived in their entirety from a native gene, or be composed of different elements derived from promoters found in nature, and/or comprise synthetic nucleotide segments. Those skilled in the art will readily ascertain that different promoters can regulate expression of a coding sequence or gene in response to a particular stimulus, e.g., in a cell- or tissue-specific manner, in response to different environmental or physiological conditions, or in response to specific compounds. Promoters are typically classified into two classes: inducible and constitutive.

A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of said regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region can be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host microorganism. A promoter can be naturally-occurring, can be composed of portions of various naturally-occurring promoters, or can be partially or totally synthetic. Guidance for the design of promoters is derived from studies of promoter structure, such as that of Harley and Reynolds, *Nucleic Acids Res.*, 15, 2343-61 (1987). In addition, the location of the promoter relative to the transcription start can be optimized. Many suitable promoters for use in microorganisms and yeast are well known in the art, as are polynucleotides that enhance expression of an associated expressible polynucleotide.

A selectable marker can provide a means to identify microorganisms that express a desired product. Selectable markers include, but are not limited to, ampicillin resistance for prokaryotes such as *E. coli*, neomycin phosphotransferase, which confers resistance to the aminoglycosides neomycin, kanamycin and paromycin (Herrera-Estrella, *EMBO J.* 2:987-995, (1983)); dihydrofolate reductase, which confers resistance to methotrexate (Reiss, *Plant Physiol. (Life Sci. Adv.)* 13:143-149, (1994)); trpB, which allows cells to utilize indole in place of tryptophan; hisD, which allows cells to utilize histinol in place of histidine (Hartman, *Proc. Natl. Acad. Sci., USA* 85:8047, (1988)); mannose-6-phosphate isomerase that allows cells to utilize mannose (WO 94/20627); hygro, which confers resistance to hygromycin (Marsh, *Gene* 32:481-485, (1984)); ornithine decarboxylase, which confers resistance to the ornithine decarboxylase inhibitor, 2-(difluoromethyl)-DL-ornithine (DFMO; McConlogue, In: *Current Communications in Molecular Biology*, Cold Spring Harbor Laboratory ed., (1987)); deaminase from *Aspergillus terreus*, which confers resistance to Blasticidin S (Tamura, *Biosci. Biotechnol. Biochem.* 59:2336-2338, (1995)); phosphinothricin acetyltransferase gene, which confers resistance to phosphinothricin (White et al., *Nucl. Acids Res.* 18:1062, (1990); Spencer et al., *Theor. Appl. Genet.* 79:625-633, (1990)); a mutant acetolactate synthase, which confers imidazolione or sulfonylurea resistance (Lee et al., *EMBO J.* 7:1241-1248, (1988)), a mutant EPSPV-synthase, which confers glyphosate resistance (Hinchee et al., *BioTechnology* 91:915-922, (1998)); a mutant psbA, which confers resistance to atrazine (Smeda et al., *Plant Physiol.* 103:911-917, (1993)), a mutant protoporphyrinogen oxidase (see U.S. Pat. No. 5,767,373), or other markers conferring resistance to an herbicide such as glufosinate.

A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions can be provided in a recombinant construct or expression construct and can be from the 3' region of the gene from which the initiation region was obtained or from a different gene. A large number of termination regions are known and function satisfactorily in a variety of hosts when utilized in both the same and different genera and species from which they were derived. Termination regions can also be derived from various genes native to the preferred hosts. The termination region is usually selected more for convenience rather than for any particular property.

The procedures described herein employ, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, N Y (1992); Guthrie and Fink, *Guide to Yeast Genetics and Molecular Biology*, Academic Press, N Y (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); Culture Of Animal Cells, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, *Essential Immunology*, 6th Edition, Blackwell Scientific Publications, Oxford (1988): Fire, et al., *RNA Interference Technology From Basic Science to Drug Development*, Cambridge University Press, Cambridge (2005); Schepers, *RNA Interference in Practice*, Wiley-VCH (2005); Engelke, RNA Interference (RNAI): *The Nuts & Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004)).

Vectors

An embodiment provides a vector or combination of vectors comprising a nucleic acid molecule encoding L-fucokinase/GDP-L-fucose phosphorylase; a nucleic acid molecule encoding oligosaccharide transporter; and a nucleic acid molecule encoding fucosyltransferase, wherein the nucleic acid molecules are operably linked to at least one expression control nucleic acid molecule. Another embodiment provides a vector or combination of vectors comprising a nucleic acid molecule encoding GDP-mannose 4,6-dehydratase (Gmd), a nucleic acid molecule encoding GDP-4-keto-6-deoxymannose 3,5-epimerase 4-reductase (WcaG), a nucleic acid molecule encoding oligosaccharide transporter; and a nucleic acid molecule encoding fucosyltransferase, wherein the nucleic acid molecules are operably linked to at least one expression control nucleic acid molecule. The vector can optionally include a nucleic acid molecule encoding α-L-fucosidase, which is operably linked to at least one expression control nucleic acid molecule.

In an embodiment a vector comprises 1, 2, 3, 4, 5, or 6 of nucleic acid molecules encoding FKP, Lac12, fucosyltransferase, Gmd, WcaG, and/or α-L-fucosidase. In an embodiment, two or more copies of each polynucleotide can be present.

In an embodiment each of the nucleic acid molecules (e.g., nucleic acid molecules that encode FKP, Lac12, fucosyltransferase, Gmd, WcaG, α-L-fucosidase) are each operably linked to an expression control nucleic acid molecule. In another embodiment two or more (e.g., 2, 3, 4, or 5) of the nucleic acid molecules are operably linked to one expression control nucleic acid molecule. A vector can comprise one or more expression control nucleic acid molecules. The polynucleotides can be expressed from a single vector or multiple vectors. The at least one expression control nucleic acid molecule can allow for expression of the polynucleotides in yeast.

Vectors for stable transformation of microorganisms and yeast are well known in the art and can be obtained from commercial vendors or constructed from publicly available sequence information. Expression vectors can be engineered to produce heterologous and/or homologous protein(s) of interest. Such vectors are useful for recombinantly producing a protein of interest and for modifying the natural phenotype of host cells.

If desired, polynucleotides can be cloned into an expression vector comprising expression control nucleic acid molecules or elements, including for example, origins of replication, promoters, enhancers, or other regulatory elements that drive expression of the polynucleotides in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

To confirm the presence of recombinant polynucleotides or recombinant genes in transgenic cells, a polymerase chain reaction (PCR) amplification or Southern blot analysis can be performed using methods known to those skilled in the art. Expression products of the recombinant polynucleotides or recombinant genes can be detected in any of a variety of ways, and include for example, western blot and enzyme assay. Once recombinant organisms have been obtained, they can be grown in cell culture.

The basic techniques used for transformation and expression in yeast are known in the art. Exemplary methods have been described in a number of texts for standard molecular biological manipulation (see Sambrook et al. (1989)). These methods include, for example, biolistic devices (see, for example, Sanford, *Trends In Biotech.* 6: 299-302, (1988)); U.S. Pat. No. 4,945,050; use of a laser beam, electroporation, microinjection or any other method capable of introducing DNA into a host cell (e.g., an NVPO).

Methods of Use

In an embodiment, an engineered xylose-utilizing yeast strain carrying 2-FL biosynthetic pathway, which uses xylose as a main carbon source instead of glucose for 2-FL production. Xylose utilization by engineered yeast strain results in lower metabolic activities of the glycolytic pathway and higher expression of genes involved in non-fermentative metabolism so that it causes redirection of metabolic fluxes toward 2-FL production from ethanol production. Moreover, heterologous polynucleotides for 2-FL production (i.e., GDP-mannose 4,6-dehydratase (Gmd), GDP-4-keto-6-deoxymannose 3,5-epimerase 4-reductase (WcaG), oligosaccharide transporter, and fucosyltransferase) can be integrated into the chromosome of recombinantly engineered yeast to express polynucleotides stably without structural and segregational instability. Copy numbers of integrated heterologous polynucleotides in the engineered yeast can lead to enhanced 2-FL secretion and increased 2-FL productivity Additional embodiments provide methods of fermenting compositions comprising L-fucose and lactose with genetically modified microorganisms described herein. Cell culture media can comprise about 2, 5, 10, 20, 30, 40, 50, 60, 70, 80% or more L-fucose. Cell culture media can comprise about 2, 5, 10, 20, 30, 40, 50, 60, 70, 80% or more lactose. Further embodiments provide methods of fermenting compositions comprising glucose or xylose and lactose with genetically modified microorganisms described herein. Cell culture media can comprise about 2, 5, 10, 20, 30, 40, 50, 60, 70, 80% or more glucose. Cell culture media can comprise about 2, 5, 10, 20, 30, 40, 50, 60, 70, 80% or more lactose. Cell culture media can comprise about 2, 5, 10, 20, 30, 40, 50, 60, 70, 80% or more xylose. A genetically modified microorganism is contacted with the substrates containing L-fucose and lactose, or glucose and lactose, or xylose and lactose under fermentation conditions such that they are metabolized into 2'-fucosyllactose and L-fucose.

An embodiment provides methods for production of 2'-fucosyllactose comprising culturing recombinant yeast cells in a cell culture media in the presence of xylose and lactose, wherein the recombinant yeast cell produces 2'-fucosyllactose. The recombinant yeast cells can comprise heterologous nucleic acid molecules encoding polypeptides GDP-mannose 4,6-dehydratase (Gmd), GDP-4-keto-6-deoxymannose 3,5-epimerase 4-reductase (WcaG), oligosaccharide transporter, and fucosyltransferase operably linked to at least one expression control nucleic acid molecule. In an embodiment, the recombinant yeast cells can have the heterologous nucleic acid molecules integrated into a chromosome of the recombinant yeast cell. Alternatively, the heterologous nucleic acid molecules are present on episomal plasmids in the yeast cells. In an embodiment, 2, 3, 4, 5, or more copies of heterologous nucleic acid molecules can be present on episomal plasmids or can be integrated into one or more chromosomes of the recombinant yeast cells.

Xylose can be present in the cell culture media at about 5, 10, 20, 30, 40 g/L or more. Lactose can be present in the cell culture media at about 0.2, 0.5, 1.0, 2.0, 3.0, 3.5, 4.0, 5.0 g/L or more.

Cell specific productivity can be from about 0.2, 0.3, 0.4, 0.5, 0.6 g 2'-fucosyllactose/g cell or more.

In an embodiment about 40, 50, 60, 70, 80, 90% or more of the 2'-fucosyllactose is secreted by the recombinant yeast cell into the cell culture media. About 5, 10, 11, 12, 13, 14, 15 g/L or more of 2'-fucosyllactose can be produced. The cell culture medium can be buffered to prevent a decrease in the pH below about 6, 5, 4, 3,5, 3, 2.5 or less.

In an embodiment, the fermentation is a fed-batch fermentation or a shaking flask fed-batch fermentation where the lactose level is maintained at about 0.5, 0.8, 1.0, 1.2, 1.4, 1.6, 1.8, 2.0, 2.2., 2.4, 2.6 or more g/L and the xylose level is maintained at about 12, 14, 15, 17, 19, 20, 22, 25 or more g/L. In an embodiment the fermentation is taken to an OD600 of about 50, 55, 57, 60, 65 or more. In an embodiment, the dry cell weight at the end of the fermentation is about 25, 28, 29, 30, 35 g or more. In an embodiment 2-FL can be produced with a productivity of 0.09, 0.1, 0.13, 0.15, 0.2, 0.25 g/L/H or more, and the final yield of total 2-FL can be about 0.50, 0.55, 0.60, 0.65, 0.7 mol/mol or more.

An embodiment provides a method for production of 2'-fucosyllactose comprising culturing a recombinant microorganism comprising heterologous nucleic acid molecules encoding polypeptides L-fucokinase/GDP-L-fucose phosphorylase (FKP), oligosaccharide transporter, and fucosyltransferase operably linked to at least one expression control nucleic acid molecule in a cell culture media in the presence of L-fucose, lactose, or a combination of L-fucose and lactose. In an embodiment, the recombinant yeast cells can have the heterologous nucleic acid molecules integrated into a chromosome in the recombinant yeast cell. Alternatively, the heterologous nucleic acid molecules are present on episomal plasmids in the yeast cells.

The yield of 2-FL can be about 0.2, 0.4, 0.6, 0.8, 1.0, 1.5, 2.0, 2.5, 3.0, 3.5, 4.0 or more mole/mole from L-fucose, lactose, or a combination of L-fucose and lactose.

An embodiment provides a method for production of 2'-fucosyllactose comprising culturing a recombinant yeast comprising heterologous nucleic acid molecules encoding polypeptides GDP-mannose 4,6-dehydratase (Gmd), GDP-4-keto-6-deoxymannose 3,5-epimerase e 4-reductase (WcaG), oligosaccharide transporter, and fucosyltransferase operably linked to at least one expression control nucleic acid molecule in a cell culture media in the presence of glucose, lactose, or a combination of glucose and lactose, wherein the transgenic microorganism produces 2'-fucosyllactose. In an embodiment, the recombinant yeast cells can have the heterologous nucleic acid molecules integrated into a chromosome in the recombinant yeast cell. Alternatively, the heterologous nucleic acid molecules are present on episomal plasmids in the yeast cells. The yield of 2-FL can be about 0.2, 0.4, 0.6, 0.8, 1.0, 1.5. 2.0, 2.5, 3.0, 3.5, 4.0 or more mole/mole from L-fucose, glucose, lactose, xylose, or a combination of two or more of these.

A method is provided for production of L-fucose comprising culturing a transgenic microorganism comprising heterologous nucleic acid molecules encoding polypeptides GDP-mannose 4,6-dehydratase (Gmd), GDP-4-keto-6-deoxymannose 3,5-epimerase 4-reductase (WcaG), oligosaccharide transporter, and fucosyltransferase, and α-L-fucosidase operably linked to at least one expression control nucleic acid molecule in a cell culture media in the presence of glucose and lactose, wherein the transgenic microorganism produce L-fucose. About 0.2, 0.3, 0.4, 0.5, 0.6, 0.8, 1.0, 1.5, 2.0, 3.0 or more L-fucose can be produced. In an embodiment, the recombinant yeast cells can have the heterologous nucleic acid molecules integrated into a chromosome in the recombinant yeast cell. Alternatively, the heterologous nucleic acid molecules are present on episomal plasmids in the yeast cells.

Substrates containing L-fucose, lactose, glucose, and/or xylose can be, for example, feedstocks such as terrestrial biomass feedstock (e.g., lignocellulosic biomass feedstock) or marine biomass feedstock. Feedstocks such as acid whey can also be used in the methods described herein. Feedstocks are substance used as a raw material for the growth of an organism, including an industrial growth process. A feedstock can be the raw material used to supply a carbon or other energy source for a recombinant microorganism.

In fermentation processes a genetically modified microorganism is cultivated in a fermentation medium or substrate that includes, for example L-fucose and lactose, glucose and lactose, or xylose and lactose. A batch, fed-batch, or continuous fermentation process can be used. The fermentation medium or substrate can contain nutrients as required by the particular microorganism, including a source of nitrogen (such as amino acids proteins, inorganic nitrogen sources such as ammonia or ammonium salts, and the like), and various vitamins, minerals and the like.

Fermentation conditions, such as temperature, cell density, selection of substrate(s), selection of nutrients, and can be determined by those of skill in the art. Temperatures of the medium during each of the growth phase and the production phase can range from above about 1° C. to about 50° C. The optimal temperature can depend on the particular microorganism used. In an embodiment, the temperature is about 30° C., 35° C., 40° C., 45° C., or 50° C.

A fermentation can be conducted aerobically, microaerobically or anaerobically. Fermentation medium can be buffered during the fermentation so that the pH is maintained in a range of about 5.0 to about 9.0, or about 5.5 to about 7.0. Suitable buffering agents include, for example, calcium hydroxide, calcium carbonate, sodium hydroxide, potassium hydroxide, potassium carbonate, sodium carbonate, ammonium carbonate, ammonia, ammonium hydroxide and the like. The fermentation methods can be conducted continuously, batch-wise, or some combination thereof.

A fermentation reaction can be conducted over about 1, 2, 5, 10, 15, 20, 24, 25, 30, 36, 48, 50, 60, 70, 80, 90, or more or hours. Determinations of sugar consumption can be conducted after about 1, 2, 5, 10, 15, 20, 24, 25, 30, 36, 48, 50, 60, 70, 80, 90, or more or hours of fermentation by recombinant microorganisms. Determinations of product formation (e.g., amount of 2'-fucosyllactose or L-fucose) can be conducted after about 1, 2, 5, 10, 15, 20, 24, 25, 30, 36, 48, 50, 60, 70, 80, 90, or more or hours of fermentation by the engineered microorganisms.

An embodiment is provided for a method for producing 2'-fucosyllactose comprising culturing a recombinant microorganism described herein with a substrate under conditions to produce the 2'-fucosyllactose. In an embodiment the recombinant microorganism comprises one or more heterologous polynucleotides encoding L-fucokinase/GDP-L-fucose phosphorylase polypeptides, oligosaccharide transporter polypeptides, and fucosyltransferase polypeptides. In an embodiment, the substrate contains about 1, 2, 5, 10, 20, 30, 40, 50% or more L-fucose and lactose. The L-fucose and lactose can be transported in the cell and then converted to 2'-fucosyllactose.

A method is provided for producing 2'-fucosyllactose comprising culturing a recombinant microorganism described herein with a substrate under conditions to produce 2'-fucosyllactose. In an embodiment the recombinant microorganism comprises one or more heterologous polynucleotides encoding GDP-mannose 4,6-dehydratase (Gmd), GDP-4-keto-6-deoxymannose 3,5-epimerase 4-reductase (WcaG), and oligosaccharide transporter. In an embodiment, the substrate contains about 1, 2, 5, 10, 20, 30, 40, 50% or more glucose and lactose. The glucose and lactose can be transported in the cell and then converted to 2'-fucosyllactose.

An embodiment is provided for a method for producing L-fucose comprising culturing a recombinant microorganism described herein with a substrate under conditions to produce the 2'-fucosyllactose. In an embodiment the recombinant microorganism comprises one or more heterologous polynucleotides encoding GDP-mannose 4,6-dehydratase (Gmd), GDP-4-keto-6-deoxymannose 3,5-epimerase 4-reductase (WcaG), oligosaccharide transporter, and α-L-fucosidase. In an embodiment, the substrate contains about 2, 5, 10, 20, 30, 40, 50% or more glucose and lactose. The glucose and lactose can be transported in the cell and then converted to L-glucose.

Recovery and purification of L-fucose or 2-FL can be accomplished using any methodology known in the art. In an example active carbon (charcoal) can be used for purification. Specifically, active carbon can be filled into a column and fermentation broth and cell lysates can be eluted into the column. After washing the column can be washed with, for example, 5% ethanol. About 30% ethanol can be used to elute 2-FL from the column. The eluted 30% ethanol with 2-FL can be evaporated and freeze-dried to obtain a powder of 2-FL.

While 2-fucosyllactose can be separated and purified from the fermentation broth as described above, 2-fucosyllactose can be obtained as a form of yeast extract from the harvested cells. For instance, the harvested yeast cells after the fermentation can be disrupted to obtain 2-fucosyllactose enriched yeast extract via yeast autolysis. Either traditional yeast autolysis methods, or autoclaving the harvested cells can be conducted to release 2-fucosyllactose from the yeast cells. Once the yeast cells are fully disintegrated, centrifugal or membrane separation can be performed to obtain a liquid faction containing 2-fucosyllactose and soluble yeast extract components only. The liquid fraction can be concentrated and dried to produce 2-fucosyllactose enriched yeast extract. By doing so, 2-fucosyllactose enriched yeast extract with about 5. 10, 15, 20, 25, 30, 35% or more 2-fucosyllactose (w/w) can be obtained. As yeast extract is widely used as food ingredient, cosmetic ingredient, and animal feed, the 2-fucosyllactose enriched yeast extract can be applied for numerous applications in food, cosmetic, and animal feed industries. Production and use of 2-fucosyllactoe enriched yeast extract instead of purified 2-fucosylalctose can enable more economic applications of 2-fucosyllactose for food, cosmetic, animal feed products.

The following are provided for exemplification purposes only and are not intended to limit the scope of the invention described in broad terms above.

EXAMPLES

Some examples provide, inter alia, genetically engineered microorganisms, i.e., yeast, and methods to produce 2-FL via the salvage pathway using L-fucose and lactose as the substrates for producing 2-FL. First, overproduction of GDP-L-fucose was examined by expressing three different FKPs from *Bacteroides* species, including *B. fragilis* 9343. Secondly, an α-1,2-fucosyltransferase from *H. pylori*, and a lactose permease (Lac12) from K. lactics were introduced into a GDP-L-fucose accumulating strain to produce 2-FL. Finally, 2-FL produced in the engineered yeast was verified by mass spectrometry and fermentation conditions were modified to increase titers of 2-FL. This is the first report of 2-FL production using engineered yeast as a host.

Genes coding for FKP from *B. fragilis* and other bacteria were tested for their efficacy for the production GDP-L-fucose. FKP genes from B. thetaiotaomicron and B. ovatus were introduced into *S. cerevisiae*, and subsequent production of GDP-L-fucose was confirmed in this study. The overexpression of *B. fragilis* 9343 fkp led to the highest production of GDP-L-fucose in engineered yeast.

After introducing three genes (fkp, fucT2, and LAC12) which are necessary for the production of 2-FL production into *S. cerevisiae,* 2-FL production by the engineered yeast (D452-2_LFF) was verified. This is the first report of 2-FL production by engineered yeast. By batch fermentation, via the salvage pathway, 92 mg/L of 2-FL was produced in the engineered yeast.

The present disclosure has demonstrated, for the first time, that 2-FL can be produced by engineered *S. cerevisiae* via the salvage pathway. Considering numerous benefits of using a GRAS host for mass production, these results have paved a road for the economic and safe production of 2-FL.

Example 1. GDP-L-Fucose Accumulation in Engineered Yeast

Figure 2:
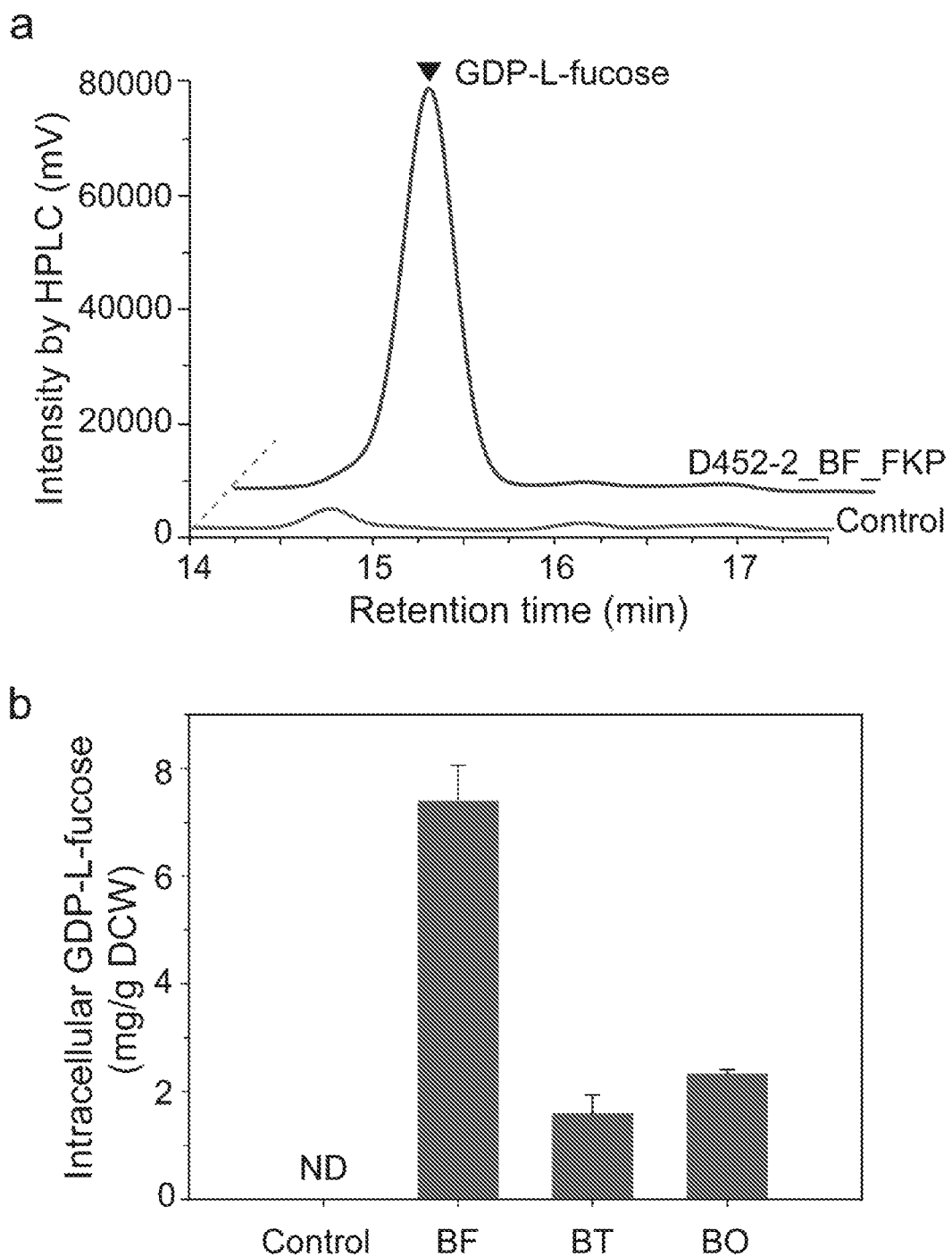
FIG. 2. Production of 5'-diphosphate-L-fucose (GDP-L-fucose) in engineered *Saccharomyces cerevisiae*. Engineered strains cultured in yeast synthetic complete (YSC) medium composed of 6.7 g/L yeast nitrogen base with 20 g/L glucose, 0.69 g/L CSM-Leu, 5 g/L L-fucose, and 2 mM $MgCl_2$ in 50 mM potassium hydrogen phthalate buffer (pH 5.5) at 30° C. and 250 rpm for 36 h. (a) The overlaid HPLC chromatograms of D452-2_BF_FKP and control strains. (b) Comparison of intracellular GDP-L-fucose concentrations depending on the origin of the gene, fkp, coding for L-fucokinase/GDP-L-fucose phosphorylase (FKP). Control (D452-2_FKP_Control), *S. cerevisiae* D452-2 harboring pRS425GPD: BF (D452-2_BF_FKP), *S. cerevisiae* D452-2 harboring pRS425GPD_BF_fkp; BT (D452-2_BT_FKP), *S. cerevisiae* D452-2 harboring pRS425GPD_BT_fkp; and BO (D452-2_BO_FKP), *S. cerevisiae* D452-2 harboring pRS425GPD_BO_fkp; ND, not detectable; DCW, dry cell weight.

In order to produce 2-FL in engineered yeast, ample supply of GDP-L-fucose is necessary for fucosylation of lactose by α-1,2-fucosyltransferase. To enable accumulation of GDP-L-fucose in the cytosol, genes coding for FKP originating from 3 different *Bacteroides* species were individually introduced into *S. cerevisiae* D452-2. When the engineered yeast D452-2_BF_FKP overexpressing FKP from *B. fragilis* 9343 was cultured in the presence of fucose, a significant peak at an approximate retention time of 15.1 min was detected in the sample (FIG. 2a). In contrast, no peak was detected in the sample from the control strain (D452-2_FKP_Control harboring the empty plasmid).

Regardless of the origin of fkp, the production of GDP-L-fucose by the engineered yeasts was confirmed. However, the amount of GDP-L-fucose produced in the strain D452-2_BF_FKP overexpressing FKP from *B. fragilis* 9343 was higher than that in the strains D452-2_BT_FKP and D452-2_BO_FKP overexpressing FKPs from B. thetaiotaomicron or B. ovatus by 4.6 and 3.2 times, respectively (FIG. 2b). These results indicate that all three genes coding for FKP originating from *B. fragilis* 9343, B. thetaiotaomicron, and B. ovatus were functionally expressed, which enabled the yeast to produce GDP-L-fucose intracellularly. However, different concentrations of intracellular GDP-L-fucose were measured depending on the origin of genes coding for FKP. Thus, fkp from *B. fragilis* 9343, which showed the highest concentration of intracellular GDP-L-fucose was selected to be introduced into *S. cerevisiae* D452-2 for 2-FL production.

Example 2. Production and Identification of 2-FL in the Engineered Yeast

Figure 3:
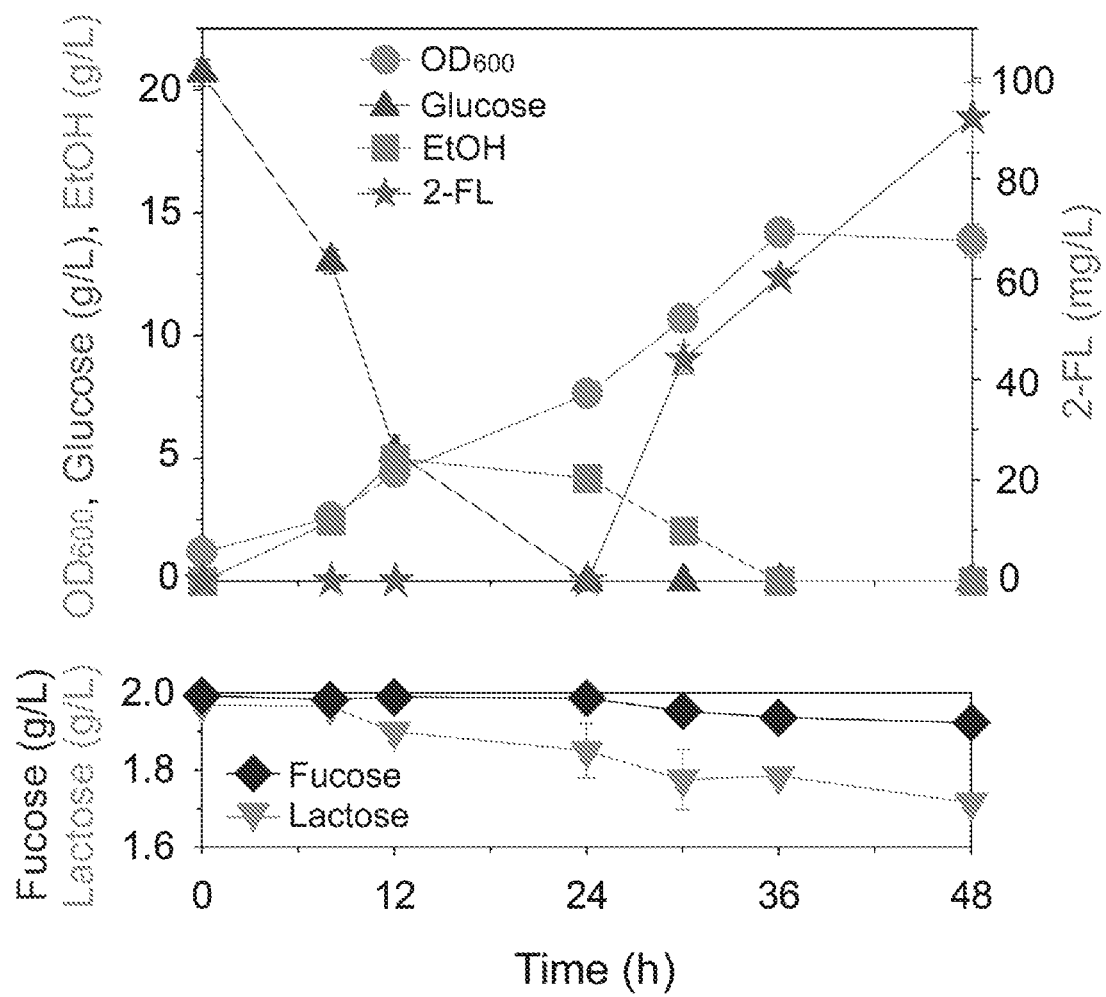
FIG. 3. Batch fermentation profiles of engineered *Saccharomyces cerevisiae* D452-2_LFF in the Verduyn medium with 20 g/L glucose, 2 g/L fucose, and 2 g/L lactose in 50 mM potassium hydrogen phthalate buffer (pH 5.5) at 30° C. and 250 rpm for 48 h. During fermentation, the cell density ($OD_{600}$) and concentrations of glucose, ethanol (EtOH), and 2'-fucosyllactose (2-FL) were monitored by HPLC. *S. cerevisiae* D452-2_LFF, *S. cerevisiae* D452-2 harboring fkp encoding L-fucokinase/guanosine 5'-diphosphate-L-fucose phosphorylase, fucT2 encoding α-1,2-fucosyltransferase, and LAC12 encoding lactose permease.

To produce 2-FL via the salvage pathway in engineered yeast, three heterologous genes (fkp, fucT2, LAC12) coding for *B. fragilis* 9343 FKP, *H. pylori* α-1,2-fucosyltransferase, K. lactics lactose permease were overexpressed in *S. cerevisiae* D452-2. To confirm 2-FL production in the resulting yeast strain (D452-2_LFF), flask cultures were performed. Initially added glucose and ethanol produced during glucose fermentation were completely consumed within 36 h, 92 mg/L of 2-FL was produced at 48 h (FIG. 3). Until 48 h, 70 mg/L of L-fucose and 285 mg/L of lactose were consumed. Thus, the yields of 2-FL were 0.44 mole/mole from L-fucose and 0.25 mole/mole from lactose.

Example 3. Production of 2-FL in Engineered Yeast

Figure 4:
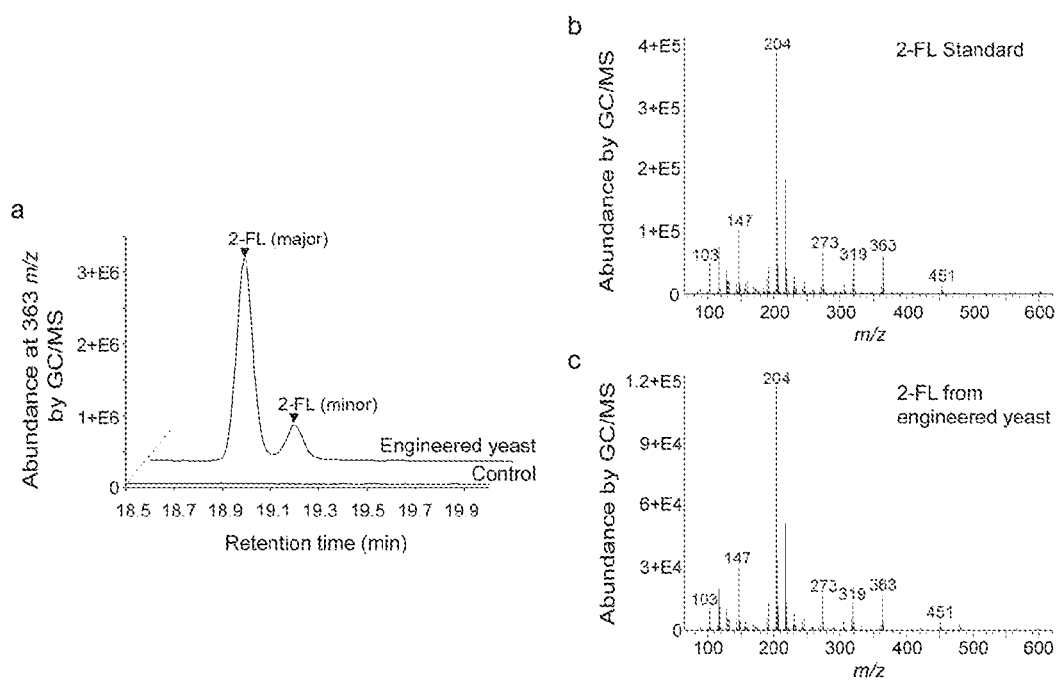
FIG. 4. Identification of 2'-fucosyllactose (2-FL) produced by batch fermentation of the engineered yeast *Saccharomyces cerevisiae* D452-2_LFF strain by GC/MS. (a) The overlaid GC/MS chromatogram at 363 m/z that shows the unique daughter ions of 2-FL. Mass spectra of (b) 2-FL standard and (c) 2-FL produced by D452-2_LFF. *S. cerevisiae* D452-2_LFF, *S. cerevisiae* D452-2 harboring fkp encoding L-fucokinase/guanosine 5'-diphosphate-L-fucose phosphorylase, fucT2 encoding α-1,2-fucosyltransferase, and LAC12 encoding lactose permease; Control, the D452-2_LFF_Control strain harboring three empty plasmids.

To verify the production of 2-FL by the engineered yeast (D452-2_LFF), 2-FL produced in the culture broth was analyzed by GC/MS. The selected ion chromatogram (at 363 m/z) of the culture broth of the D452-2_LFF and D452-2_LFF_Control strains indicated that 2-FL was produced only by the engineered *S. cerevisiae* D452-2_LFF (FIG. 4a). By comparing the mass fragmentation patterns of 2-FL standard with its unique fragment ions at 103, 147, 204, 217, 273, 319, and 363 m/z (FIGS. 4b) and 2-FL synthesized by the D452-2_LFF strain (FIG. 4c), the production of 2-FL by the D452-2_LFF strain was confirmed.

Figure 5:
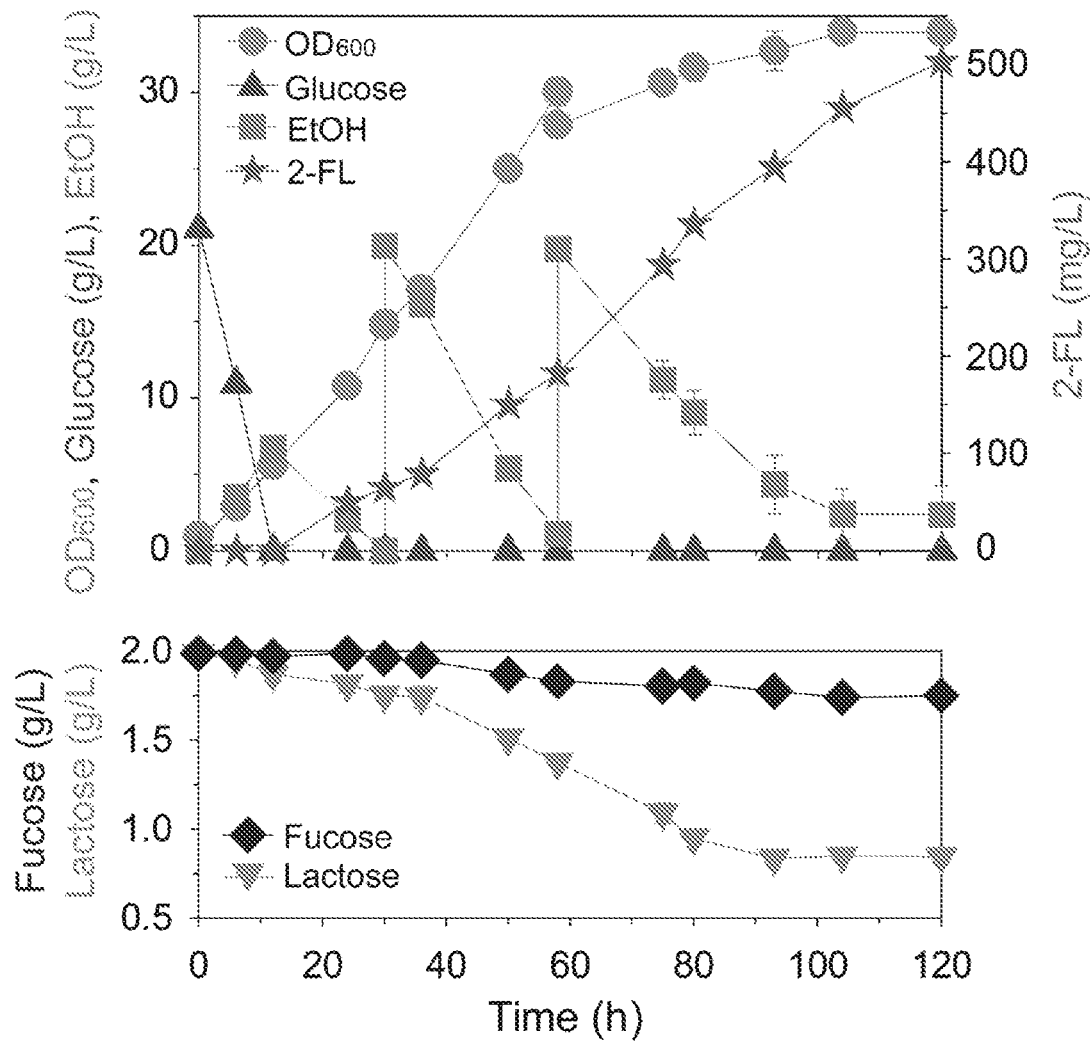
FIG. 5. Production of 2'-fucosyllactose (2-FL) by fed-batch fermentation of the engineered *Saccharomyces cerevisiae* D452-2_LFF strain. Ethanol was fed intermittently when depleted. During the fermentation, the cell density ($OD_{600}$) and the concentrations of glucose, ethanol (EtOH), and 2-FL were monitored using HPLC. *S. cerevisiae* D452-2_LFF, *S. cerevisiae* D452-2 harboring fkp encoding L.-fucokinase/guanosine 5'-diphosphate-L-fucose phosphorylase, fucT2 encoding α-1,2-fucosyltransferase, and LAC 12 encoding lactose permease.

Example 4. Fed-Batch Fermentation for the Production of 2-FL by Engineered Yeast Fed-batch fermentation of the D452-2_LFF strain was performed to investigate the feasibility of mass production of 2-FL by the engineered yeast. In order to increase the titer of 2-FL, the fermentation conditions, such as medium components, temperature, and agitation speed were maintained as those of batch fermentation, but ethanol was intermittently fed as a carbon source (FIG. 5). Ethanol produced from the initially added glucose was completely consumed at 36 h, and 20 g/L ethanol was added to the flask two times. However, ethanol was not consumed anymore after 120 h. Therefore, the fermentation was stopped, and $OD_{600}$ reached 34.0 and 2-FL concentration reached 503 mg/L at 120 h (FIG. 5). Until 120 h, 270 mg/L of L-fucose and 1.19 g/L of lactose were consumed (FIG. 5). Thus, the final yields of 2-FL were 0.63 mole/mole from L-fucose and 0.3 mole/mole from lactose.

Figure 6:
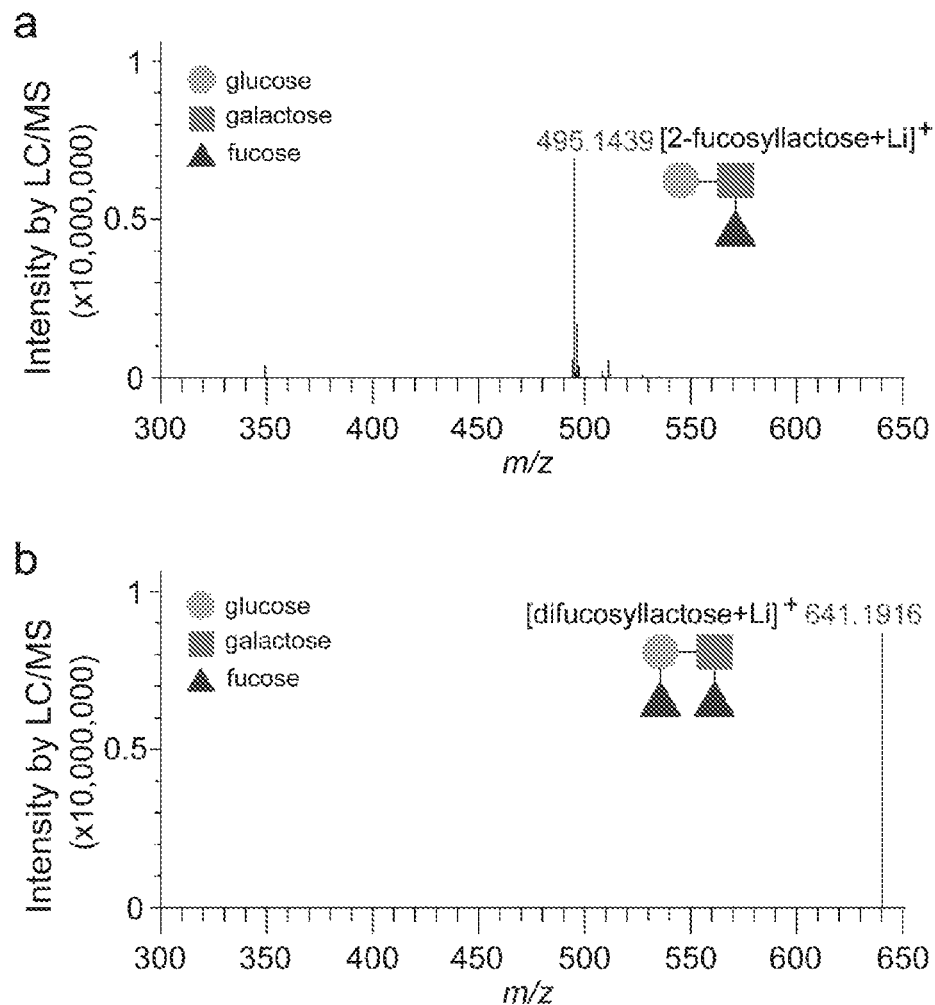
FIG. 6. Identification of 2'-fucosyllactose (2-FL) produced by fed-batch fermentation of the engineered yeast. *Saccharomyces cerevisiae* D452-2_LFF. The mass spectra of (a) 2-FL and (b) difucosyllactose produced during fed-batch fermentation were obtained by LC/MS. *S. cerevisiae* D452-2_LFF, *S. cerevisiae* D452-2 harboring fkp encoding L-fucokinase/guanosine 5'-diphosphate-L-fucose phosphorylase, fucT2 encoding α-1,2-fucosyltransferase, and LAC12 encoding lactose permease.

For the verification of 2-FL produced by fed-batch fermentation, a subsequent analysis of 2-FL was performed by LC/MS. The ion at 495.1439 m/z corresponding to 2-FL [(2-FL+Li)$^+$] was detected in the culture broth from fed-batch fermentation (FIG. 6a). The production of difucosyllactose was also confirmed by detecting the ion at 641.1916 m/z corresponding to difucosyllactose [(difucosyllactose+Li)$^+$] (FIG. 6b).

Example 5. Production of 2-FL in Engineered S. cerevisiae

Figure 9:
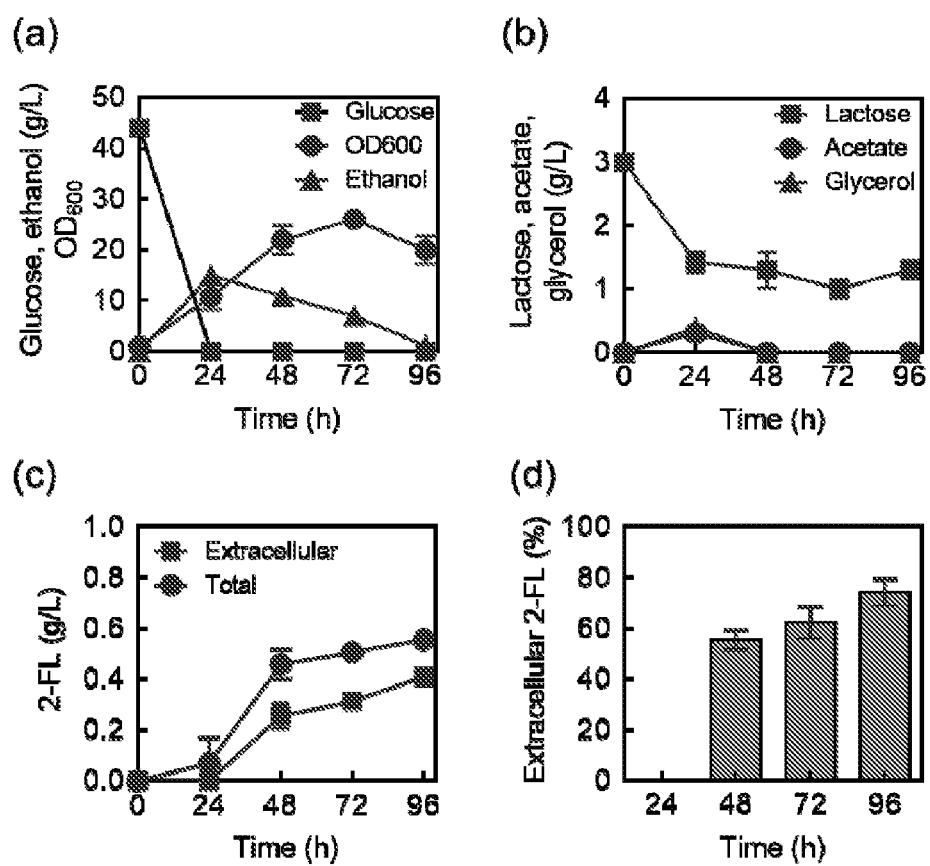
FIG. 9. 2-FL production by engineered yeast D452L-gwf. The concentrations of glucose, ethanol, lactose, acetate, glycerol, and 2-FL were monitored by HPLC. (a), glucose consumption, ethanol production and consumption, and yeast cell growth. (b), lactose consumption, acetate and glycerol production. (c), the concentrations of total 2-FL and extracellular 2-FL. (d), the ratio of extracellular 2-FL over the course of fermentation. Results are the mean of duplicated experiments; error bars indicate standard deviations and are not visible when smaller than the symbol size.

As the D452L-gw strain harboring lactose permease, and GDP-L-fucose producing enzymes can assimilate lactose and produce GDP-L-fucose intracellularly, the last enzymatic reaction to be introduced for the production of 2-FL is α-1,2-fucosyltransferase which can transfer fucosyl group from GDP-L-fucose into lactose. FucT2 from H. pylori was introduced into the D452L-gw to construct the D452L-gwf strain expressing all necessary enzymes to produce 2-FL. When the D452L-gwf was cultured in YP medium with 40 g/L of glucose and 3 g/L of lactose (FIG. 9), 2-FL production was observed (FIG. 9c). Glucose was all consumed within 20 hours (FIG. 9a) and yeast cells continued to grow utilizing ethanol as a carbon source after glucose depletion (FIG. 9a). The extracellular 2-FL concentration measured from the culture broth reached 0.42 g/L, and the total 2-FL concentration measured after cell lysis of cells was 0.56 g/L, indicating that 25% of synthesized 2-FL was trapped inside yeast cells (FIG. 9c and FIG. 9d). Nonetheless, we demonstrated that 2-FL could be produced by engineered yeast expressing Lac12, Gmd, WcaG, and fucosyltransferase.

Example 6. L-Fucose Production in Engineered S. cerevisiae

Figure 10:
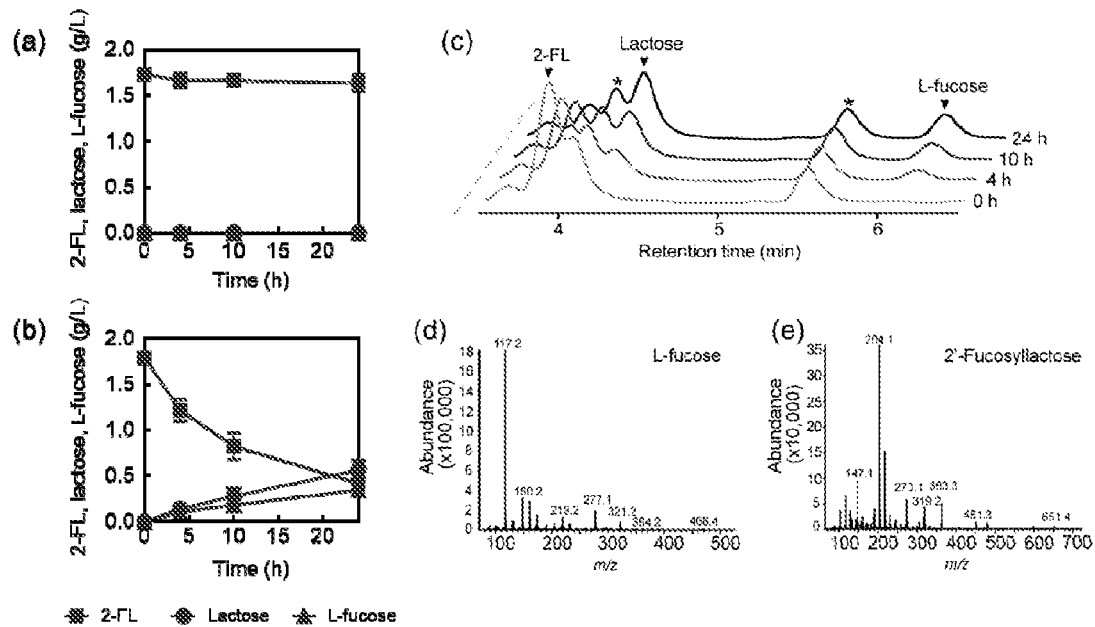
FIG. 10. Confirmation of α-L-fucosidase activity in *S. cerevisiae* in vitro. (a), incubation of 2-FL with cell lysate of strain D452L-gwf with empty plasmid as a control; (b), incubation of 2-FL with cell lysate of strain D452L-gwf-fuco with α-L-fucosidase expression; (c), the HPLC chromatograph of cell lysate of D452L-gwf-fuco incubated with 2-FL. 2-FL, lactose, and L-fucose were indicated. *, unknown peak from medium; (d) and (e) are GC/MS confirmation of L-fucose and 2-FL, respectively. Results are the mean of duplicated experiments; error bars indicate standard deviations and are not visible when smaller than the symbol size.
Figure 11:
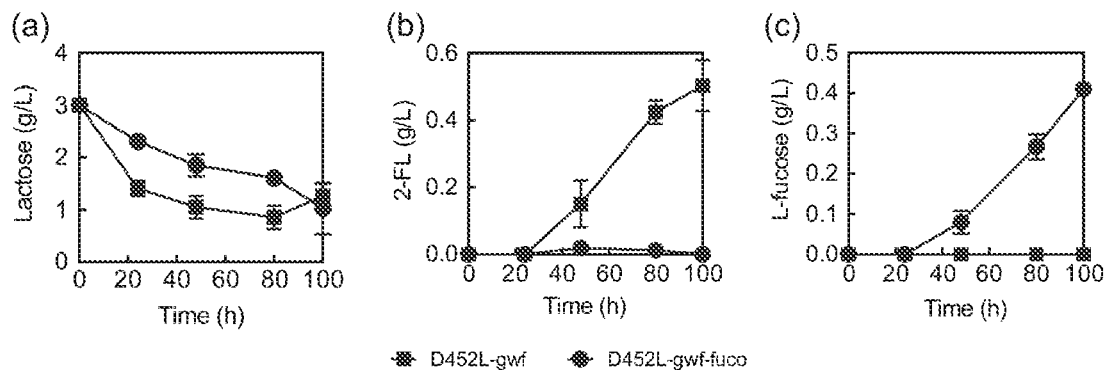
FIG. 11. L-fucose production by introducing α-L-fucosidase into a 2-FL producing yeast strain. (a), lactose consumption. (b), 2-FL production. (c), L-fucose production. D452L-gwf, 2-FL producing strain; D452L-gwf-fuco, D452L-gwf strain with expression of α-L-fucosidase. Results are the mean of duplicated experiments; error bars indicate standard deviations and are not visible when smaller than the symbol size.

To further investigate whether or not 2-FL production by engineered yeast was hindered from feedback inhibition caused by intracellularly accumulated 2-FL, α-L-fucosidase from X. manihotis was introduced into the D452L-gwf strain. We reasoned that elimination of intracellular 2-FL by hydrolysis of fucose residue from 2-FL by α-L-fucosidase into L-fucose and lactose might alleviate possible feedback inhibition by 2-FL on GDP-fucose producing enzymes (FIG. 7). In vitro activity of α-L-fucosidase was confirmed by incubating 2-FL with the cell lysates of the D452L-gwf-fuco strain expressing α-L-fucosidase and the D452L-gwf strain carrying an empty plasmid (FIG. 10). The cell lysate from the D452L-gwf-fuco strain hydrolyzed 2-FL into L-fucose and lactose while that from the control strain did not (FIGS. 10a and 10b). L-fucose and 2-FL were detected and confirmed by HPLC and GC/MS (FIG. 10c-e). This result confirmed that α-L-fucosidase was functionally expressed in S. cerevisiae After confirming the activity of α-L-fucosidase in S. cerevisiae in vitro, yeast fermentation was performed and the production of 2-FL and L-fucose was monitored (FIG. 11). The D452L-gwf-fuco strain expressing α-L-fucosidase consumed lactose slower than the control strain D452L-gwf with an empty plasmid during fermentation (FIG. 11a). This reduced lactose consumption might be attributed to the recycle of lactose in the cell through hydrolysis of 2-FL by α-fucosidase (FIG. 7). The D452L-gwf with an empty plasmid produced 0.51 g/L of 2-FL without L-fucose production. However, the α-L-fucosidase expressing D452L-gwf-fuco strain produced 0.41 g/L of L-fucose extracellularly without 2-FL production (FIGS. 11b and 11c). L-fucose was not detected even in the lysate of the D452L-gwf-fuco cells indicating that L-fucose could be secreted into culture broth efficiently. As L-fucose can be generated only through hydrolysis of 2-FL, 0.41 g/L of L-fucose production can be interpreted that the D452L-gwf-fuco might have a capacity to produce up to 1.22 g/L of 2-FL if the produced L-fucose remained in the 2FL as molecular weights of 2-FL and L-fucose are 488 and 164, respectively. These results suggest that 2-FL production could be further improved with efficient export of intracellular 2-FL (see Example 18).

Example 7. Materials and Methods

Strains, Plasmids, and Yeast Transformation

Genes coding for FKP were from three Bacteroides species, namely, B. fragilis 9343, Bacteroides thetaiotaomicron, and Bacteroides ovatus (Table 1 and 2). The fucT2 gene from H. pylori was codon-optimized for the expression in S. cerevisiae and synthesized by Integrated DNA Technologies (Coraville, IA, USA). LAC12 coding for lactose permease was amplified from the genomic DNA of K. lactis (Table 1 and 2). E. coli TOP10 (Invitrogen, Carlsbad, CA, USA) was used for construction and manipulation of plasmids (Table 1 and 2). S. cerevisiae D452-2 (MATalpha, leu2, his3, ura3, and can1) (Hosaka et al., (1992). A dominant mutation that alters the regulation of INO1 expression in Saccharomyces cerevisiae. The Journal of Biochemistry, 111(3), 352-358) was used as the host for producing 2-FL in this study (Table 3). Plasmids were transformed into S. cerevisiae by the lithium acetate/single-stranded carrier DNA/polyethylene glycol method as described previously (Gietz, R. D., & Schiestl, R. H. (2007). High-efficiency yeast transformation using the LiAc/SS carrier DNA/PEG method. Nature Protocols, 2(1), 31-34).

TABLE 1

Primers used in the salvage pathway study

| Name Primer | Description Sequence (5' to 3'; restriction sites are underlined) | SEQ ID NO | Ref |
|---|---|---|---|
| F_BF_fkp (BamHI) | ATA<u>GGATCC</u>ATGCAAAAACTACTATCTTTG CCTCCTAATC | 1 | This study |
| R_BF_fkp (SalI) | ATA<u>GTCGAC</u>TTATGATCGTGATACTTGGAA TCCCTTATCCG | 2 | This study |

TABLE 1-continued

Primers used in the salvage pathway study

| Name Primer | Description Sequence (5' to 3'; restriction sites are underlined) | SEQ ID NO | Ref |
|---|---|---|---|
| F_BT_fkp (BamHI) | ATA<u>GGATCC</u>ATGCCGGAGCCGATCTGCTGTTTCCTTC | 3 | This study |
| R_BT_fkp (SaII) | ATA<u>GTCGAC</u>TTAGCTTCTCGATACCTGTAATCC | 4 | This study |
| F_BO_fkp (BamHI) | ATA<u>GGATCC</u>ATGCAAAAGTTATTATCCTTACCAC | 5 | This study |
| R_BO_fkp (SaII) | ATA<u>GTCGAC</u>TTAGCTTCTTGAAACCTGAAGTCCCTTGTCAG | 6 | This study |
| F_LAC12 (SpeI) | TCTAGAGCGGCCGC<u>ACTAGT</u>GCCACCATGGCAGATCATTCGAGCAG | 7 | This study |
| R_LAC12 (SaII) | TCTAGAGCGGCCGC<u>GTCGAC</u>TTAAACAGATTCTGCCTCTG | 8 | This study |
| F_fucT2 (SpeI) | GG <u>ACTAGT</u>ATGGCCTTTAAGGTCGT | 9 | This study |
| R_fucT2 (XhoI) | CCG<u>CTCGAG</u>TTAGGCATTATACTTTTGAGACTTAACT | 10 | This study |

TABLE 2

Plasmids used or constructed in the salvage pathway study.

| Name | Description | Reference |
|---|---|---|
| pRS423GPD | HIS3, GPD promoter, CYC1 terminator, 2 µ origin, and Amp<sup>r</sup> | (Christianson, Sikorski, Dante, Shero, & Hieter, 1992) |
| pRS425GPD | LEU2, GPD promoter, CYC1 terminator, 2 µ origin, and Amp<sup>r</sup> | (Christianson, Sikorski, Dante, Shero, & Hieter, 1992) |
| pRS426GPD | URA3, GPD promoter, CYC1 terminator, 2 µ origin, and Amp<sup>r</sup> | (Christianson, Sikorski, Dante, Shero, & Hieter, 1992) |
| pRS425GPD_BF_fkp | pRS425GPD harboring fkp from *B. fragilis* 9343 | This study |
| pRS425GPD_BT_fkp | pRS425GPD harboring fkp from *B. thetaiotaomircon* | This study |
| pRS425GPD_BO_fkp | pRS425GPD harboring fkp from *B. ovatus* | This study |
| pRS423GPD_LAC12 | pRS425GPD harboring LAC12 from *K. lactics* | This study |
| pRS426GPD_fucT2 | pRS425GPD harboring fucT2 from *H. pylori* | This study |

TABLE 3

Strains used or constructed in the salvage pathway study

| Name | Description | Reference |
|---|---|---|
| D452-2 | *S. cerevisiae*, MATα, leu2, his3, ura3, and can1 | (Hosaka, Nikawa, Kodaki, & Yamashita, 1992) |
| D452-2_FKP_Control | D452-2 harboring pRS425GPD | This study |
| D452-2_BF_FKP | D452-2 harboring pRS425GPD_BF_fkp | This study |
| D452-2_BT_FKP | D452-2 harboring pRS425GPD_BT_fkp | This study |
| D452-2 BO_FKP | D452-2 harboring pRS425GPD_BO_fkp | This study |
| D452-2_LFF | D452-2 harboring pRS423GPD_LAC12, pRS425GPD_BF_fkp, and pRS426GPD_fucT2 | This study |
| D452-2_LFF_Control | D452-2 harboring pRS423GPD, pRS425GPD, and pRS426GPD | This study |

Plasmids and strains construction for de novo pathway.

To enable *S. cerevisiae* to assimilate lactose, LAC12 encoding for lactose permease was cloned into pRS423-pGPD plasmid. LAC12 gene fragment was amplified by polymerase chain reactions (PCR) from the genomic DNA of *K. lactis* (NRRL: Y-8279) using primer pairs (LAC12-F and LAC12-R). The PCR product and pRS423-pGPD were digested by SpeI and SalI, and ligated to construct plasmid pRS423-pGPD-LAC12. The constitutive expression cassette of LAC12 was then amplified from pRS423-pGPD-LAC12 using primer pairs of CS8-IU and CS8-ID, and integrated into the CS8 site of yeast strain D452-2 for stable expression. The resulting strain was designated as D452L.

For de novo synthesis of GDP-L-fucose, gmd and wcaG genes were obtained by PCR using the genomic DNA of *E. coli* K-12 as a template. Two PCR primers, gmd-F and gmd-R, were used for amplification of gmd gene. After digestion of the amplified gmd gene fragment and pRS423-pGPD plasmid with SpeI and ClaI, they were ligated to construct plasmid pRS423-pGPD-gmd. Similarly, wcaG gene was amplified by two PCR primers (wcaG-F and wcaG-R). The wcaG gene fragment and pRS425-pGPD plasmid were digested with BamHI and HindIII, and ligated to construct plasmid pRS425-pGPD-wcaG. Plasmids pRS423-pGPD-gmd and pRS425-pGPD-wcaG were transformed into strain D452L to make strain D452L-gw.

For expression of alpha-1,2-fucosyltransferase, fucT2 gene from *H. pylori* UA802 was codon-optimized for *S.*

*cerevisiae* and synthesized using the gBlocks® service from Integrated DNA Technologies (IDT), Inc. (Skokie, IL). The fucT2 gene was then amplified by primers fucT2_F and fucT2_R using the synthesized DNA as a template. The fucT2 gene fragment and pRS426-pGPD plasmid were digested with BamHI and ClaI, and ligated to construct plasmid pRS426-pGPD-fucT2. The plasmid pRS426-pGPD-fucT2 was then transformed into strain D452L-gw and the resulting strain was named as D452-gwf.

The gBlocks® fragment of the gene encoding α-L-fucosidase from X. manihotis was synthesized from IDT, Inc. (Skokie, IL). The synthesized fragment was blunt ligated with plasmid pRS42H-pGPD digested by SmaI. The resulting plasmid was designated as pRS42H-pGPD-fuco. Strain D452-gwf-fuco was constructed by introducing plasmid pRS42H-pGPD-fuco into D452-gwf strain. Primers, plasmids, and strains used in this work are listed in Table 1, Table 2, and Table 3, respectively. All constructed plasmids were confirmed by DNA sequencing.

Strains and Media for de novo pathway work.

*E. coli* Top10 [F-mcrA Δ(mrr-hsdRMS-mcrBC) φ80lacZΔM15 ΔlacX74 recA1 araD139 Δ(ara-leu) 7697 galU galK rpsL (StrR) endA1 nupG] was used for construction and propagation of plasmids. *E. coli* was grown in lysogeny broth (LB, 5 g/L yeast extract, 10 g/L tryptone, 10 g/L NaCl, pH 7.0) at 37° C. with ampicillin (100 μg/mL) added for selection when required. *S. cerevisiae* D452-2 (MATalpha, leu2, his3, ura3, and can1) was used as a host strain for 2-FL and L-fucose production. Yeast strains were grown on YP medium (10 g/L yeast extract, 20 g/L peptone) containing 20 g/L glucose at 30° C. Yeast strains transformed with plasmids containing antibiotic markers were propagated on YPD (YP with 20 g/L of glucose) plates supplemented with the corresponding antibiotics such as Hygromycin (300 μg/mL). Synthetic complete medium (SC, 1.7 g/L of yeast nitrogen base with 5 g/L of ammonium sulfate and appropriate amino acids, pH 6.5) containing 20 g/L of glucose (SCD) was used for maintaining plasmids in auxotrophic strains.

TABLE 4

Primers used for de novo pathway study

| Primer name | Primer sequence | SEQ ID NO | Source |
|---|---|---|---|
| LAC12-F | 5'-tctagagcggccgcactagtgccaccatggcagacattcgagcag-3' | 17 | *K. lactis* Y-8279 |
| LAC12-R | 5'-tctagagcggccgcgtcgacttaaacagattctg cctctg-3' | 18 | |
| gmd-F | 5'-tctagagcggccgcactagtgccaccatgtcaaaagtcgctctcatcac-3' | 19 | *E. coli* K-12 |
| gmd-R | 5'-tctagagcggccgcatcgatttatgactccagcg cgatcg-3' | 20 | |
| wcaG-F | 5'-tctagagcggccgcggatccgccaccatgagtaaacaacgagttttattgc-3' | 21 | *E. coli* K-12 |
| wcaG-R | 5'-tctagagcggccgcaagctttaccccgaaagc ggtctt-3' | 22 | |
| fucT2-F | 5'-tctacagcggccgcggatccgccaccatggcctttaaggtcgtcc-3' | 23 | *H. pylori* UA802 |
| fucT2-R | 5'-tatagagcggccgcatcgatggcattatactttt gagac-3' | 24 | |
| CS8-IU | 5'-Caaaattacctacggtaattagtgaaaggc-caaaatctaatgtt acaataaattaaccctcactaaaggga-3' | 25 | *S. cerevisiae* |
| CS8-ID | 5'-Gaccgttcccttgtgttgtaccagtggtagggttcttctcggta gcttctgtaatacgactcactatagggc-3' | 26 | |

TABLE 5

Plasmids used in the de novo pathway study

| Name | Description of plasmids | Source |
|---|---|---|
| pRS423-pGPD | HIS3, GPD promoter, CYC1 terminator, 2μ origin, and Amp$^R$ | Christianson et al. *Gene* 1992, 110, 119-22. |
| pRS425-pGPD | LEU2, GPD promoter, CYC1 terminator, 2μ origin, and Amp$^R$ | Christianson et al. 1992 |
| pRS426-pGPD | URA3, GPD promoter, CYC1 terminator, 2μ origin, and Amp$^R$ | Christianson et al. 1992 |
| pRS423-pGPD-LAC12 | pRS423-pGPD harboring LAC12 gene from *K. lactis* Y-8279 | This study |

TABLE 5-continued

Plasmids used in the de novo pathway study

| Name | Description of plasmids | Source |
|---|---|---|
| pRS423-pGPD-gmd | pRS423-pGPD harboring gmd gene from E. coli K-12 | This study |
| pRS425-pGPD-wcaG | pRS425-pGPD harboring wcaG gene from E. coli K-12 | This study |
| pRS426-pGPD-fucT2 | pRS426-pGPD harboring fucT2 gene from H. pylori UA802 | This study |
| pRS42H-pGPD-fuco | pRS42H-pGPD harboring a-L-fucosidase gene from X. manihotis | This study |

TABLE 6

Strains used in the de novo pathway study

| Strain name | Description of strains | Source |
|---|---|---|
| D452-2 | MATα leu2 ura3 his3 can1 | Hosaka et al., J. Biochemistry 1992, 111, 352-358 |
| D452L | D452-2 with CS8-LAC12 integration | This study |
| D452L-gw | D452L with pRS423-pGPD-gmd and pRS425-pGPD-wcaG | This study |
| D452L-gwf | D452L-gw with pRS426-pGPD-fucT2 | This study |
| D452L-gwf-fuco | D452L-gwf with pRS42H-pGPD-fuco | This study |

Medium and Culture Conditions

E. coli strains were grown in Luria-Bertani (LB) medium containing 100 μg/mL ampicilin at 37° C. and 200 rpm for plasmid amplification. After yeast transformation, Yeast Synthetic Complete (YSC) medium was used, which contained 6.7 g/L yeast nitrogen base with 20 g/L glucose, 20 g/L agar, and 0.69 g/L CSM-Leu (MP Biomedicals, Solon, OH, USA) or 0.65 g/L CSM-His-Leu-Ura (MP Biomedicals), which supplied appropriate nucleotides and amino acids to select transformants using an auxotrophic marker.

To verify the accumulation of GDP-L-fucose by expressing FKP in engineered yeast, three engineered S. cerevisiae strains, D452-2_BF_FKP harboring fkp from B. fragilis 9343, D452-2_BT_FKP harboring fkp from B. thetaiotaomicron, D452-2_BO_FKP harboring fkp from B. ovatus, and D452-2_FKP_Control harboring an empty vector, were grown in the YSC medium containing 6.7 g/L yeast nitrogen base with 20 g/L glucose, 0.69 g/L CSM-Leu, 5 g/L fucose, and 2 mM MgCl$_2$ in 50 mM potassium hydrogen phthalate (KHP) buffer (pH 5.5) at 30° C. and 250 rpm for 36 h. Initial cell densities were adjusted to optical density at 600 nm (OD$_{600}$)=0.1.

To examine 2-FL production in the engineered yeast (D452-2_LFF) expressing three heterologous genes (fkp, fucT2, and LAC12), batch fermentation was performed in a 50-mL flask containing 10 mL of synthetic Verduyn medium (Verduyn et al. (1992). Effect of benzoic acid on metabolic fluxes in yeasts: a continuous-culture study on the regulation of respiration and alcoholic fermentation. Yeast, 8(7), 501-517) with 20 g/L glucose as a carbon source for growth, and 2 g/L fucose and 2 g/L lactose as substrates for 2-FL production in 50 mM KHP buffer (pH 5.5) at 30° C. and 250 rpm. For this fermentation, initial cell densities were adjusted to OD$_{600}$=1. As a control, batch fermentation of strain D452-2_LFF_Control harboring three empty vectors was also performed under the same conditions. To produce high-titer 2-FL, fed-batch fermentation was performed in a 125-mL baffled flask containing 25 mL of synthetic Verduyn medium with 20 g/L glucose, 2 g/L fucose, and 2 g/L lactose in 50 mM KPH buffer (pH 5.5) at 30° C. and 250 rpm. For this fermentation, initial cell densities were adjusted to OD$_{600}$=1. After the initially added glucose and ethanol produced from glucose during cultivation were completely consumed, 20 g/L ethanol was added. When ethanol was depleted, additional 20 g/L ethanol was fed into the flask until 120 h.

Yeast culture, fermentation, and metabolite analysis for de novo pathway. To measure intracellular lactose, 1 mL of yeast cells grown on YPD overnight were collected and incubated with 3 g/L of lactose in liquid YP medium. The mixture was cultured at 30° C. for 6 hours at 250 rpm. The yeast cells were collected and washed twice to remove the entire medium component. The cells were suspended in 500 μL of distilled water and boiled for 10 minutes to release intracellular lactose. Intracellular lactose was measured by HPLC (Agilent Technologies 1200 Series, Santa Clara, CA). HPLC was equipped with a Rezex ROA-Organic Acid H+(8%) column (Phenomenex Inc., Torrance, CA) and a refractive index detector (RID). The column was eluted with 0.005 N H2SO4 at a flow rate of 0.6 mL/min at 50° C.

To measure intracellular GDP-L-fucose, 500 μL of yeast cell culture on YPD for 50 hours was collected and washed twice. Then, the cell pellets were resuspended in 500 UL of distilled water. The cells were disrupted by continuous beating with glass beads for 40 min to release intracellular metabolites. The yeast cell lysis was achieved by boiling for 2 min and centrifuging for 10 min at 15,000 rpm to remove all debris. The supernatant was injected into a high-performance liquid chromatography (HPLC) system with a diode array detector (Beckman Coulter System Gold, Pasadena, CA) using a CAPCELL PAK C18 MG column (250×4.6 mm, Shiseido, Tokyo, Japan). The column was eluted at a flow rate of 0.6 mL/min with 98% (v/v) of 20 mM triethylamineacetate at pH 6.0 and 2% of acetonitrile. GDP-L-fucose was detected by absorbance at 254 nm.

To produce 2-FL and L-fucose, fermentation was performed by inoculating overnight pre-culture (5 mL of SCD medium without appropriate amino acid for maintaining plasmids) into 20 mL of YPD40L3 (YP medium with 40 g/L of glucose and 3 g/L of lactose) in a 125-mL Erlenmeyer flask with an initial optical density at 600 nm (OD$_{600}$)=1.0 and incubated at 30° ° C. and 250 rpm. OD$_{600}$ was monitored by a spectrophotometer (Biomate™ 5, Thermo, NY). Extracellular metabolites such as glucose, glycerol, acetate, ethanol, lactose, and 2-FL were measured by HPLC (Agilent Technologies 1200 Series, Santa Clara, CA) with a Rezex ROA-Organic Acid H+(8%) column (Phenomenex Inc., Torrance, CA) and a refractive index detector (RID). The column was eluted with 0.005 N H2SO4 at a flow rate of 0.6 mL/min at 50° C. To measure total (intracellular and extracellular) 2-FL, the fermentation broth with yeast cells was boiled for 10 min to release all the intracellular 2-FL and centrifuged at 15,000 rpm for 10 min. The supernatant was then analyzed by HPLC.

Analytical Methods

Cell growth was monitored by $OD_{600}$ using a UV-visible spectrophotometer (Biomate™ 5; Thermo Fisher Scientific, Waltham, MA, USA). To confirm the production of GDP-L-fucose and to measure intracellular GDP-L-fucose concentrations in engineered yeast, 5 mL of cell culture was harvested by centrifugation at 1,789×g for 5 min at 4° C., washed with distilled water, and resuspended in 500 µL of distilled water. The cells were disrupted using glass beads for 1 h. After centrifugation at 9,447×g for 10 min, 10 µL supernatant was injected into an HPLC system (Shimadzu, Kyoto, Japan) equipped with a CAPCELL PAK C18 MG column (250 ×4.6 mm, Shiseido, Tokyo, Japan) at 30° C. The flow rate of a mobile phase composed of 20 mM triethylamine at pH 6 and 2% (v/v) acetonitrile was set at 0.6 mL/min. GDP-L-fucose was detected at 254 nm by HPLC, and the concentration of GDP-L-fucose was calculated from its peak area using the GDP-L-fucose standard (Carbosynth, Compton, UK). The concentrations of glucose, fucose, 2-FL, and ethanol were measured by an HPLC system (Agilent Technologies 1200; Agilent Technologies, Wilmington, DE, USA) equipped with a refractive index (RI) detector using a Rezex ROA-Organic Acid H+(8%) column (Phenomenex, Torrance, CA, USA). The column and RI detector temperatures were set at 50° C., and the column was eluted with 0.005 N of H2SO4 at a flow rate of 0.6 mL/min. The concentration of lactose was measured by the HPLC system (Agilent Technologies 1200) equipped with a RI detector using a Rezex RCM-Monosaccharide $Ca^{+2}$ (8%) column (Phenomenex). The column and RI detector temperatures were set at 80° C., and the column was eluted with water at a flow rate of 0.6 mL/min Identification of 2-FL produced in the engineered yeast To identify 2-FL produced in the engineered yeast, the culture broth was analyzed using gas chromatography/mass spectrometry (GC/MS) and liquid chromatography/mass spectrometry (LC/MS). For GC/MS analysis, the culture broth obtained from batch fermentation of D452-2_LFF and D452-2_Control was centrifuged at 9,447×g for 10 min, and 20 µL of supernatant was dried in a centrifugal vacuum evaporator. For chemical derivatization, 10 µL of 40 mg/mL methoxyamine hydrochloride in pyridine (Sigma-Aldrich, St. Louis, MO, USA) was added to the dried sample, and incubated at 30° C. After 90 min, 45 UL of N-methyl-N-(trimethylsilyl)-trifluoroacetamide (Sigma-Aldrich) was added and incubated for 30 min at 37° C. The 2-FL standard (Carbosynth) was derivatized using the same method described above. The chemically derivatized samples were analyzed using an Agilent 7890A GC/5975C MSD system (Agilent Technologies) equipped with an HP-5 ms column (30 m in length, 0.25 mm in diameter, and film thickness of 0.25 m; Agilent Technologies) and a 10-m guard column. The derivatized sample (1 µL) was injected into the GC column in a splitless mode. The oven temperature was programmed to be initially at 80° C. for 1 min and then be ramped to 300° ° C. at 10° C./min for 1 min. Electron ionization was performed at 70 eV, and the temperatures of the ion source and transfer line were 250° C. and 280° C., respectively. The mass range used was 85-700 m/z.

To analyze the culture broth of fed-batch fermentation, LC/MS ion-trap and time-of-flight system (Shimadzu, Kyoto, Japan) equipped with a Thermo Hypercarb porous graphitic carbon LC column (100 mm in length, 2.1 mm in diameter, and a 3-µm particle size; Thermo Fisher Scientific) was used. The mobile phase was composed of solution A (25 UM lithium chloride) and B (acetonitrile). The mass spectrometer was operated in a positive ion mode. The injection volume of each sample was 20 µL. The gradient elution was from 0 (v/v) to 80% in 41 min and the flow rate of the mobile phase was set at 0.2 mL/min. The temperatures of the LC column and the autosampler were set at 70 and 10° C., respectively. Source-dependent parameters were set at: nebulizing gas flow rate, 1.5 L/min; interface voltage, 4.5 kV; detector voltage, 1.65 kV; curved desolvation line temperature, 200° C.; and heat block temperature, 200° C. The mass range used was 100-700 m/z.

Confirmation of α-L-fucosidase enzymatic activity in vitro.

Strain D452L-gwf-fuco containing α-L-fucosidase and D452L-gwf with empty plasmid pRS42H as control were cultured in YPD medium with 300 µg/mL of hygromycin to maintain plasmid. 5 mL of yeast cell cultures were taken when yeast $OD_{600}$ reached 10. Yeast cells were collected by centrifugation at 15,000 rpm at 4° C. for 2 min and suspended in 500 µL of 50 mM Tris-HCl (pH 7.5) buffer. The yeast cells were subjected to cell lysis by glass bead beating at 4° C. using FastPrep-24™ homogenizer (MP Biomedicals, Solon, OH). After centrifugation at 15,000 rpm at 4 GC for 10 min, the supernatant was incubated with 2 g/L of 2-FL at 30° C. for 24 h. The samples from different time points were analyzed using HPLC. 2-FL and L-fucose were identified through gas chromatography/mass spectrometry (GC/MS).

Identification of 2-FL and L-fucose using GC/MS. For identification of L-fucose and 2-FL, the samples were analyzed using GC/MS. 20 µL of supernatant was dried in a centrifugal vacuum evaporator. For chemical derivatization, 10 µL of 40 mg/mL methoxyamine hydrochloride in pyridine (Sigma-Aldrich, St. Louis, MO) was added to the dried sample incubated at 30° C. After 90 min, 45 µL of N-methyl-N-(trimethylsilyl)-trifluoroacetamide (Sigma-Aldrich) was added to the sample incubated for 30 min at 37° C. The chemically derivatized samples were analyzed using an Agilent 7890A GC/5975C MSD system (Agilent Technologies) equipped with an HP-5 ms column (30 m in length, 0.25 mm in diameter, and film thickness of 0.25 m; Agilent Technologies) and a 10-m guard column. The derivatized sample (1 µL) was injected into the GC column in a splitless mode. The oven temperature was programmed to be initially at 80° ° C. for 1 min and then ramped to 300° C. at 10° C./min for 1 min. Electron ionization was performed at 70 eV. The temperatures of ion source and transfer line were 250° C. and 280° C., respectively. The mass range used was 85-700 m/z.

Lactose Transport and GDP-L-fucose Accumulation in Engineered S. cerevisiae.

As S. cerevisiae does not naturally assimilate lactose, which is a precursor for 2-FL synthesis, the introduction of a heterologous lactose transporter is desirable to produce 2-FL in the cytosol of S. cerevisiae. Therefore, LAC12 coding for lactose permease from Kluyveromyces lactis, was integrated into the genome of the D452-2 strain under the control of a constitutive promoter (pGPD). To evaluate the functional expression of LAC12 in S. cerevisiae, the intracellular lactose concentrations of the D452L strain and a parental strain (D452-2) were measured after incubating cells with 3 g/L of lactose for 6 h. The D452L strain expressing LAC12 accumulated 0.11 g lactose/g cell intracellularly while the parental strain D452-2 showed no accumulation of intracellular lactose (FIG. 8a and FIG. 8b). Thus, lactose assimilation in the engineered *S. cerevisiae* (D452L) via heterologous expression of LAC12 was confirmed.

The other precursor for 2-FL biosynthesis is GDP-L-fucose that serves as a fucosyl donor for the fucosylation of transported lactose. GDP-L-fucose can be synthesized from GDP-D-mannose which is already synthesized in yeast by introducing two enzymes: GDP-D-mannose-4,6-dehydratase (Gmd) and GDP-4-keto-6-deoxymannose 3,5-epimerase 4-reductase (WcaG) from *E. coli* (FIG. 7). Overexpression of Gmd and WcaG in the D452L strain resulted in the D52L-gw strain which can accumulate GDP-L-fucose intracellularly. The D452L-gw strain accumulated 1.56 mg GDP-L-fucose/g cell after incubating for 50 h in YPD (FIG. 8c and FIG. 8d). By overexpressing *E. coli* Gmd and WcaG, efficient production of GDP-L-fucose in *S. cerevisiae* was achieved.

Secretion of 2-FL might increase the intracellular concentration of 2-FL and the elevated 2-FL levels might cause feedback inhibition on the 2-FL synthesis pathway. In order to examine if the export of 2-FL from the cytosol to a culture medium is indeed a limiting factor of 2-FL production by engineered yeast, α-L-fucosidase, which hydrolyzes 2-FL into lactose and L-fucose, was introduced into a 2-FL producing yeast. The intracellular hydrolysis of 2-FL into lactose and L-fucose will eliminate 2-FL buildup so that the maximum potential of the 2-FL synthesis pathway can be realized. The results showed that the strain D452L-gwf-fuco expressing α-L-fucosidase produced 0.41 g/L of L-fucose, while control strain D452L-gwf with an empty plasmid produced 0.51 g/L of 2-FL without L-fucose production (FIGS. 11b and 11c). 0.41 g/L of L-fucose production indicated that the engineered yeast D452L-gwf-fuco has a potential to generate 1.22 g/L of 2-FL, as L-fucose can be generated only through hydrolysis of 2-FL. These results suggest that intracellularly accumulated 2-FL might have inhibited the enzymes in the 2-FL biosynthesis pathway of *S. cerevisiae*, and 2-FL production could be further improved if efficient export of intracellular 2-FL is facilitated. (See Example 18).

Figure 8:
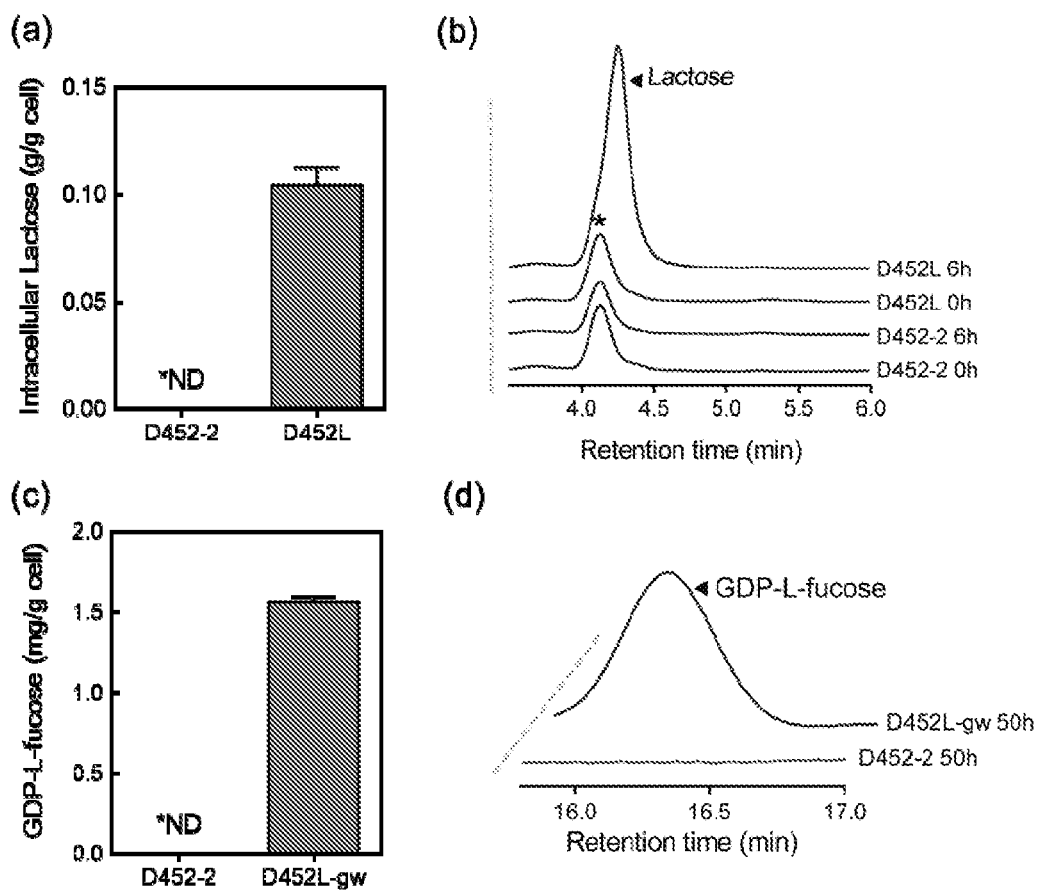
FIG. 8. Lactose transport and GDP-L-fucose production by engineered yeast. (a), D452L carrying lactose permease (Lac12) transported lactose into the cell; (b), GDP-L-fucose was produced by introducing gmd and wcaG into D452L strain. D452-2, parental strain as a control; D452L, D452-2 with Lac12 expression; D452L-gw. D452L with Gmd and WcaG expression. *ND, not detected; (b) *; unknown peak from medium. Results are the mean of duplicated experiments; error bars indicate standard deviations.

Another possible reason for low 2-FL production by engineered yeast might be a mismatch of intracellular lactose and GDP-L-fucose concentrations. As shown in FIG. 8, lactose was transported into yeast cells efficiently by Lac12. The intracellular lactose concentration reached 0.11 g lactose/g cell within 6 hours, i.e. ca 10% of yeast weight is lactose. However, the intracellular GDP-L-fucose concentration was 1.56 mg GDP-L-fucose/g cell which was 70-fold lower than the intracellular lactose concentration. Levels of intracellular GDP-L-fucose might not be high enough for the fucosylation reaction of lactose to produce 2-FL.

Additionally, excessive intracellular lactose can be toxic to engineered yeast. Lactose may be toxic to organisms lacking a ß-galactosidase gene because of excessive accumulation of lactose in the cytosol. A similar toxic effect caused by lactose was noted in our engineered yeast strains carrying Lac12 transporter without ß-galactosidase. As such, we tested different lactose concentrations and were able to choose 3 g/L of lactose. Even with only 3 g/L of lactose in the medium, almost 10% (w/w) of the yeast cell was filled with lactose, indicating that Lac12 is a very efficient lactose transporter. A careful adjustment of Lac12 activity to balance between efficient supply of lactose and possible toxic effects can be used for the enhanced production of 2FL.

2-FL production by engineered *S. cerevisiae* was accomplished through a de novo pathway. Also, the production of L-fucose was achieved after introducing α-L-fucosidase into the 2-FL producing engineered yeast.

Example 8 Materials and Methods for Xylose Studies

Construction of pRS425_Gmd-wcaG: For de novo synthesis of GDP-L-fucose, gmd and wcaG genes were obtained by PCR by using the genomic DNA of *E. coli* K-12 as a template.

Construction of pRS403_Gmd-wcaG or PRS406_Gmd-wcaG: For construction of integrative Gmd-wcaG expression plasmids (pRS403_gmd-wcaG and pRS406_gmd-wcaG), a DNA fragment (vector fraction) was amplified from pRS403 or pRS406 using pRS40X-F and pRS40X-R primers, respectively. Another DNA fragment (insert fraction) was amplified from pRS426_Gmd-wcaG using Gmd-wcaG-F and Gmd-wcaG-R primers. The two PCR products were ligated together by in vitro homologous recombination using a CloneEZ® PCR cloning kit (GenScript, Piscataway, NJ, USA).

Construction of pRS423_WbgL: To express α-1,2-fucosyltransferase, wbgL gene from *E. coli* 0126 (Engels et al., WbgL: a novel bacterial α-1,2-fucosyltransferase for the synthesis of 2'-fucosyllactose. Glycobiology, 24 (2), 170-178 (2014)) was codon-optimized for *S. cerevisiae* and synthesized using the gBlocks® service from Integrated DNA Technologies (IDT) (Coraville, IA, USA). The wbgL gene was then amplified by primers wbgL_F and wbgL_R using the synthesized DNA as a template. The wbgL gene fragment and pRS423GPD plasmid were digested with NcoI and SacI, and then ligated to construct plasmid pRS423_WbgL. The synthetic oligomer for the wbgL gene and pRS423GPD plasmid were digested with SmaI, and the ligated to construct plasmid pRS423_WbgL.

Construction of Cas9-NAT and gRNA plasmids: Cas9-NAT plasmid (Addgene plasmid #64329) (Zhang et al., (2014) Construction of a Quadruple Auxotrophic Mutant of an Industrial Polyploid *Saccharomyces cerevisiae* Strain by Using RNA-Guided Cas9 Nuclease. Appl. Environ. Microbiol., 80(24), 7694-7701) was adopted for the expression of Cas9 nuclease in yeast. gRNA expression cassettes targeting intergenic site on chromosome XV (CS5), VII (CS6), XVI (CS8), and VIII (CS9) were designed by replacing the target sequence of previous gRNA cassettes (Zhang et al., 2014). The gRNA cassettes were PCR amplified using gRNA-U and gRNA-D primers and inserted into 2-u plasmids pRS42K and pRS42H (EUROSCARF).

Strain CTLdf: For construction of 2-FL producing yeast strain via episomal expression, three plasmids (pRS423_wbgL. pRS425GPD, and pRS426_Gmd-wcaG) containing wbgL, Gmd, and wcaG, respectively under the control of a constitutive promoter were transformed into the CTL strain, followed by selection on SCD-His-Leu-Ura plate.

Strain CTLD: For construction of GDP-L-fucose producing yeast strain via chromosomal expression, integrative Gmd-wcaG expression plasmid (pRS403_Gmd-wcaG) was digested with NdeI before use and integrated into the HIS3 locus of the CTL strain, followed by selection on SCD-His plate. Colonies were randomly picked from the plate, and verified by PCR amplification using primers (Conf-H/S3-F and Conf-HIS3-R).

Strain CTLD1F1: For construction of 2-FL producing yeast strain via chromosomal integration of one copy of gmd-wcaG gene and one copy of wbgL gene, 1 copy of wbgL gene was integrated into the intergenic site on chromosome VII (CS6) of the CTLD strain using CRISPR-Cas9 based genetic modification followed by selection on YPDNH plates. Colonies were randomly picked from the plate, and verified by PCR amplification using primers (Conf-CS6-F and Conf-CS6-R).

Strain CTLD2F1: For construction of 2-FL producing yeast strain via chromosomal integration of two copies of gmd-wcaG gene and one copy of wbgL gene, another integrative Gmd-wcaG expression plasmid (pRS406_Gmd-wcaG) was digested with StuI before use and integrated into the URA3 locus of the CTLD1F1 strain, followed by selection on SCD-Ura plate. Colonies were randomly picked from the plate, and verified by PCR amplification using primers (Conf-URA3-F and Conf-URA3-R).

Strain CTLD1F2: For construction of 2-FL producing yeast strain via chromosomal integration of one copy of gmd-wcaG gene and two copies of wbgL gene, another copy of wbgL gene was integrated into the intergenic site on chromosome VIII (CS9) of the CTLD1F1 strain using CRISPR-Cas9 based genetic modification, followed by selection on YPDNK plate. Colonies were randomly picked from the plate, and verified by PCR amplification using primers (Conf-CS9-F and Conf-CS9-R).

Strain CTLD2F2: For construction of 2-FL producing yeast strain via chromosomal integration of two copies of gmd-wcaG gene and two copies of wbgL gene, another copy of wbgL gene was integrated into the intergenic site on chromosome VIII (CS9) of the CTLD2F1 strain using CRISPR-Cas9 based genetic modification, followed by selection on YPDNK plate. Colonies were randomly picked from the plate, and verified by PCR amplification using primers (Conf-CS9-F and Conf-CS9-R).

TABLE 7

| Name | Description of plasmids | Reference |
| --- | --- | --- |
| pRS423GPD | HIS3, GPD promoter, CYC1 terminator, 2 μ origin, and Amp$^R$ | Christianson et al. (1992) Gene, 110(1), 119-122. |
| pRS425GPD | LEU2, GPD promoter, CYC1 terminator, 2 μ origin, and Amp$^R$ | Christianson et al. (1992) |
| pRS426GPD | URA3, GPD promoter, CYC1 terminator, 2 μ origin, and Amp$^R$ | Christianson et al. (1992) |
| pRS423_LAC12 | pRS423GPD harboring LAC12 gene from *K. lactis* Y-8279 | Liu et al. (2018) ACS Synth. Biol., 7(11), 2529-2536. |
| pRS423_WbgL | pRS423GPD harboring wbgL gene from *E. coli* | This study |
| pRS426_Gmd-wcaG | pRS426GPD harboring gmd and wcaG gene from *E. coli* K-12 | This study |
| pRS403 | HIS3 | Mumberg et al. (1995) Gene, 156(1), 119-122 |
| pRS406 | URA3 | Mumberg et al. (1995) |
| pRS403_Gmd-wcaG | pRS403 harboring | This study |
| pRS406_Gmd-wcaG | pRS405 harboring | This study |
| pCas9-NAT | Cas9 expression plasmid, NAT1 marker | Zhang et al. (2014) |
| pRS42K | 2 μ origin, KanMX | EUROSCARF |
| pRS42H | 2 μ origin, hph | EUROSCARF |
| pRS42K-CS5 | pRS42H, gRNA cassette targeting the intergenic site on Chr XV | This study |
| pRS42H-CS6 | pRS42H, gRNA cassette targeting the intergenic site on Chr VII | Kwak et al. (2017) Biotechnology and Bioengineering, 114(11), 2581-2591. |
| pRS42H-CS8 | pRS42H, gRNA cassette targeting the intergenic site on Chr XVI | Kwak et al. (2017) |
| pRS42K-CS9 | pRS42K, gRNA cassette targeting the intergenic site on Chr VIII | This study |

TABLE 8

Primers

| Name | Direction | Sequence |
| --- | --- | --- |
| pRS40X-F | Sense | 5'ctcgagtcatgtaattagttatgtcacgcttacattcacgccctcccccacatccgctctaaccgaaaaggaaggagtt-3' SEQ ID NO: 27 |
| pRS40X-R | Antisense | 5'gaattcctgcagcccgggggatccactagttctagaatccgtcgaaactaagttctggtgttttaaaactaaaaaaaaga-3' SEQ ID NO: 28 |
| Gmd-wcaG-F | Sense | 5'caccagaacttagtttcgacggattctagaactagtggatcccccgggctgcaggaattcatgaaagctgacggaccta-3' SEQ ID NO: 29 |
| Gmd-wcaG-R | Antisense | 5'gagcggatgtgggggagggcgtgaatgtaagcgtgacataactaattacatgactcgagttagattttagataccacaa-3' SEQ ID NO: 30 |
| Conf-His3-F | Sense | 5'-ttcttttctattactcttggcctcctcta-3' SEQ ID NO: 31 |
| Conf-His3-R | Antisense | 5'-ctacataagaacacctttggtg-3' SEQ ID NO: 32 |
| Conf-Ura3-F | Sense | 5'-aattgatgacaatacagacgatgataacaa-3' SEQ ID NO: 33 |
| Conf-Ura3-R | Antisense | 5'-ttagttttgctggccgcatc-3' SEQ ID NO: 34 |
| gRNA-CS9-F | Sense | 5'-taactattacttgtttctatgttttagagctagaaatagcaag-3' SEQ ID NO: 35 |
| gRNA-CS9-R | Antisense | 5'-atagaaacaagtaatagttagatcatttatctttcactgcgga-3' SEQ ID NO: 36 |

TABLE 8-continued

Primers

| Name | Direction | Sequence |
|---|---|---|
| dDNA-CS6-F | Sense | 5'aacctcgaggagaagttttttttaccccctctccacagatcCAGGAAACAGCTATG ACCATG-3' SEQ ID NO: 37 |
| dDNA-CS6-R | Antisense | 5'-taattaggtagaccgggtagattttttccgtaaccttggtgtcTGTAAAACGACGGCC AGT-3' SEQ ID NO: 38 |
| dDNA-CS8-F | Sense | 5'caaaattacctacggtaattagtgaaaggccaaaatctaatgttacaataAATTAAC CCTCACTAAAGGGA-3' SEQ ID NO: 39 |
| dDNA-CS8-R | Antisense | 5'gaccgttcccttgtgttgtaccagtggtagggttcttctcggtagcttctGTAATACGAC TCACTATAGGGC-3' SEQ ID NO: 40 |
| dDNA-CS9-F | Sense | 5'aggattcattagtggaaaagttcagtgacaaaatctagaaaataatatgaAATTAAC CCTCACTAAAGGGA-3' SEQ ID NO: 41 |
| dDNA-CS9-R | Antisense | 5'gaatatagcgtattttttatttaatcacggtacaatggagatatttgcatgGTAATACGA CTCACTATAGGGC-3' SEQ ID NO: 42 |
| Conf-CS6-F | Sense | 5'-gtctgccgaaattctgtg-3' SEQ ID NO: 43 |
| Conf-CS6-R | Antisense | 5'-cggtcagaaagggaaatg-3' SEQ ID NO: 44 |
| Conf-CS8-F | Sense | 5'-agtggaacatagaaggggg-3' SEQ ID NO: 45 |
| Conf-CS8-R | Antisense | 5'-taagcagcccagtgaac-3' SEQ ID NO: 46 |
| Conf-CS9-F | Sense | 5'-tggtaatgaggaatgcgt-3' SEQ ID NO: 47 |
| Conf-CS9-R | Antisense | 5'-cgggcattatgcgtagat-3' SEQ ID NO: 48 |

TABLE 9

Strains

| Strains | Description | Sources |
|---|---|---|
| D452-2 | MATα leu2 ura3 his3 can1 | Hosaka, Nikawa, Kodaki, and Yamashita (1992) |
| CT2 | Xylose-utilizing strain engineered from strain D452-2 | Tsai et al. (2015) Biotechnol. Bioeng., 112(11), 2406-2411. |
| CTL | CT2 in which the $P_{GPD}$-Lac12-$T_{CYC}$ cassette has been integrated on chr XVI | This study |
| CTLdf | CTL (pRS423_wbgL, pRS425_, and pRS426_gmd-wcaG) | This study |
| CTLD | CTL in which the $P_{GPD}$-gmd-$T_{CYC}$, $P_{PGK}$-wcaG-$T_{CYC}$ cassettes has been integrated on His3 locus | This study |
| CTLD1F1 | CTLD in which the $P_{GPD}$-wbgL-$T_{CYC}$ cassette has been integrated on chr VII | This study |
| CTLD2F1 | CTLD1F1 in which the $P_{GPD}$-gmd-$T_{CYC}$, $P_{PGK}$-wcaG-$T_{CYC}$ cassettes has been integrated on Ura3 locus | This study |
| CTLD1F2 | CTLD1F1 in which the $P_{GPD}$-wbgL-$T_{CYC}$ cassette has been integrated on chr VIII | This study |
| CTLD2F2 | CTLD1F2 in which the $P_{GPD}$-gmd-$T_{CYC}$, $P_{PGK}$-wcaG-$T_{CYC}$ cassettes has been integrated on Ura3 locus | This study |

Example 9. Stains and Media for Xylose Studies

E. coli Top10 [F-mcrA Δ(mrr-hsdRMS-mcrBC) φ80/ acZΔM15 ΔlacX74 recA1 araD139 Δ(ara-leu) 7697 galU galK rpsL (Str$^R$) endA1 nupG] was used for construction of plasmids. The E. coli strains expressing plasmids were grown in Luria Bertani (LB) medium (1% tryptone, 0.5% yeast extract, 1% NaCl) with ampicilin (100 μg/mL) at 37° C. Xylose-fermenting S. cerevisiae CT2, which contains overexpression cassettes for xylose metabolizing pathways (Tsai et al., 2015), was used as the host strain for 2-FL production. Yeast strains were cultivated at 30° C. in YP medium (10 g/L yeast extract, 20 g/L peptone) with 20 g/L glucose. For CRISPR-Cas9 based genome editing experiments, 120 μg/mL of nourseothricin, 300 μg/mL of geneticin, and 300 μg/mL of hygromycin B were added if required for the selection of transformants. To select pre-culture transformants using an amino acid auxotrophic marker, Yeast Synthetic Complete (YSC) medium was used. The YSC medium contained 6.7 g/L Yeast Nitrogen Base (YNB), 20 g/L glucose, and appropriate nucleotides and amino acids.

Strains used in this study are listed in Table 9. The plasmids, primers, and guide RNA (gRNA) target sequences used in this study are summarized in Table 7 and 8, respectively. Recombinant DNA techniques were performed according to standard procedures. The lithium acetate/single strand carrier DNA/polyethylene glycol method was used to introduce multicopy expression vectors, Cas9-NAT, gRNA expression vectors, and dDNA fragments into yeasts. Transformants were screened on selection plates and confirmed by colony PCR using confirmation primers.

Example 10. Xylose Fermentation Experiments

To produce 2-FL, engineered yeast strains were pre-cultured overnight in 5 mL of YSC medium (6.7 g/L yeast nitrogen base with appropriate amino acids) or YP medium (10 g/L yeast extract, 20 g/L peptone) containing 20 g/L glucose at 30° C. and 250 rpm. The preculture was transferred to 40 mL YSC medium or YP medium containing 20 g/L glucose, and the second pre-culture was incubated under the same conditions. Cells were collected at the mid-exponential phase and inoculated into 20 mL YP medium containing 30 g/L glucose and 2 g/L lactose (YPD30L2) or 30 g/L xylose and 2 g/L lactose (YPX30L2) in a 250 mL flask with an initial cell density (OD$_{600}$) of ~10. All flasks were incubated at 30° C., 250 rpm. For xylose fed-batch fermentation, the final resulting strain CTLD2F2 was pre-cultured as described above, then inoculated into 20 mL 2xYP medium containing 15 g/L xylose and 2 g/L lactose (2xYPX15L2) in a 250 mL flask with an initial cell density (OD$_{600}$) of ~10. When the added xylose and lactose were depleted, additional 15 g/L xylose and 2 g/L glucose were fed into the flask.

To compare intracellular GDP-L-fucose production by the CTLD strain on glucose and xylose, the strain cultured in 5 mL of YP medium containing 20 g/L glucose (YPD20) as precultures for glucose and xylose main cultures, respectively. Precultured cells were inoculated into main culture medium at an initial cell density (OD$_{600}$) of 0.1. Main cultures were performed with 20 ml of YPD30 or YPX30 in a 250 mL flask at 30° ° C., 250 rpm.

To compare lactose assimilation by the CTL strain on glucose and xylose, the strain cultured in 5 mL of YPD20 as precultures for glucose and xylose main cultures, respectively. Precultured cells were inoculated into 3 mL of YPD10L2 or YPD10L2 in a 14 mL test tube with an initial cell density (OD$_{600}$) of ~10. The mixtures were performed at 30° C., 250 rpm.

Example 11. Analytic methods

The cell density (OD$_{600}$) was monitored using a spectrophotometer (BioMate™ 5, Thermo Fisher Scientific, MA, USA). Dry cell weights of engineered yeasts were determined from plots of OD$_{600}$ and dry cell weight. Extracellular metabolites such as glucose, xylose, lactose, glycerol, ethanol, and 2-FL in culture broths were analyzed by Agilent 1200 HPLC system equipped with a refractive index detector (Agilent Technologies, Wilmington, DE, USA) and Rezex™ ROA-Organic Acid H+(8%) column (Phenomenex, Torrance, CA, USA). The flow rate of the mobile phase 0.005N H2SO4 was 0.6 mL/min, and the column temperature was 50° C.. To measure total (intracellular and extracellular) 2-FL, the fermentation broth containing yeast cells was boiled for 10 min to release all of the intracellular 2-FL and centrifuged at 21,130×g for 10 min, and then the supernatant was analyzed by HPLC.

To measure intracellular GDP-L-fucose in engineered yeast, 1.8 mL of cell culture was harvested by centrifugation at 21,130×g for 10 min, washed twice with distilled water, and resuspended with 500 µL of distilled water. The cells were disrupted by continuous beating with glass beads for 40 min. After centrifugation at 25,000×g for 20 min at 4° C., the supernatant was injected into a HPLC system (Shimadzu, Kyoto, Japan) equipped with a CAPCELL PAK C18 MG column (Shiseido, Tokyo, Japan) at 30° C. The flow rate of a mobile phase composed of 20 mM triethylamineacetate and 2% (v/v) acetonitrile was set at 0.6 mL/min. GDP-L-fucose was detected at 254 nm by HPLC, and the concentration of GDP-L-fucose was calculated from its peak height using the GDP-L-fucose standard.

To measure intracellular lactose in engineered yeast, 200 µL of the cell culture was harvested by centrifugation at 21,130×g for 5 min, washed twice with distilled water, and resuspended with 200 µL of distilled water. The cells were boiled for 10 min to release intracellular lactose. The intracellular lactose was measured by Agilent 1200 HPLC system equipped with a refractive index detector (Agilent Technologies. Wilmington, DE, USA) and Rezex ROA-Organic Acid H+(8%) column (Phenomenex, Torrance, CA, USA) as described above.

Example 12. Comparison of Episomal Plasmids Expressing Genes and Chromosomal Integration of Genes for 2-FL Production The majority of metabolic engineering endeavors in S. cerevisiae employ episomal plasmids. In particular, high copy number plasmids routinely used in S. cerevisiae can be maintained at 10-50 copies per cell, providing a convenient platform for overexpression of heterologous genes. However, there are inherent problems associated with episomal plasmids. These include segregational instability as well as variation in gene expression within the plasmids. Especially, two or more high copy number plasmids can be difficult to maintain simultaneously in a single cell.

Due to these limitations, it may be desired to integrate the 2-FL biosynthesis pathway into the genome of S. cerevisiae because multiple heterologous genes need to be expressed for 2-FL production. To examine the effects of two different approaches for heterologous genes expression to 2-FL production, CTLdf (a strain carrying episomal plasmids expressing gmd-wcaG and wbgL genes) and CTLD1F1 (a strain carrying chromosomal integration of gmd-wcaG and wbgL genes) were fermented under the same conditions (YPD30L2). After both strains consumed all glucose and lactose, total 2-FL were measured after lysis of cells. As a result, the CTLD1F1 strain produced 1.5 g/L total 2-FL, which is 1.9 fold higher than those of the CTLdf (0.8 g/L total 2-FL). Although the CTLD1F1 strain had only one copy of each gene (gmd-wcaG and wbgL), it was presumed that the CTLD1F1 strain stably expressed heterologous genes without loss of the genes in a cell, thus whole cell population were considered to produce 2-FL at the same time. However, for the CTLdf strain, some cells stably maintained multiple plasmids and properly expressed the heterologous genes, but the other cells might lose their plasmids or have different copy numbers of each plasmid due to segregational instability. As a result, only a small fraction of the whole cell population were considered to produce 2-FL. Overall, metabolic balance is more important than copy numbers in the metabolic engineering applications which are several enzymes involved in biosynthesis of target product. Here, the heterologous genes were stably expressed through chromosomal integration, which allowed the minimization of the variation of each heterologous gene expression in a cell so that the CTLD1F1 strain produced 2-FL efficiently.

Example 13. Comparison of Glucose and Xylose as Carbon Source for 2-FL Production Intracellular GDP-L-Fucose Production Whole cell biosynthesis of 2-FL can be carried out employing yeast strains that provide GDP-L-fucose through de novo or salvage biosynthetic pathway and synthesize 2-FL by exogenous α-1,2 fucosyltransferase which transfer the fucose moiety of guanosine 5'-diphosphate (GDP)-L-fucose to lactose. Therefore, the availability of GDP-L-fucose plays a vital role in the overall productivity and yield of 2-FL of this system.

GDP-L-fucose production in engineered S. cerevisiae strains uses glucose as a carbon source. Generally, S. cerevisiae has a rigid metabolic flux toward ethanol by repressing other metabolic pathways under glucose condition.

However, this well-known metabolic regulation, termed the Crabtree effect was not observed in engineered xylose-utilizing *S. cerevisiae* strains under xylose conditions. Xylose utilization leads to dysregulation of glucose-dependent repression, and consequently results in different transcription patterns of genes involved in central carbon metabolism pathway such as glycolysis, pentose phosphate pathway (PPP), and TCA cycle, as compared to glucose utilization. As a result, engineered xylose-utilizing *S. cerevisiae* strains can exhibit different metabolites profiles on xylose from those on glucose. The most drastic changes are observed in the metabolites of non-oxidative PPP and glycolysis pathway. These engineered yeast strains show larger pool sizes of the metabolites in non-oxidative PPP during xylose fermentation because xylulose, an isomerization product of xylose, is metabolized through the non-oxidative PPP. As the carbon flux from xylose through the non-oxidative PPP is merged with glycolysis at fructose-6-phophate and glyceraldehyde-3-phosphate. As a result, fructose-6-phosphate is accumulated at a relatively high amount in concert with the intermediates in non-oxidative PPP in xylose condition, compared to glucose condition. Therefore, engineered xylose-utilizing *S. cerevisiae* strains may accumulate more fructose-6-phosphate, a starting molecule of de novo pathway for GDP-L-fucose biosynthesis, under xylose conditions. A system to produce 2-FL from xylose was developed.

Figure 13:
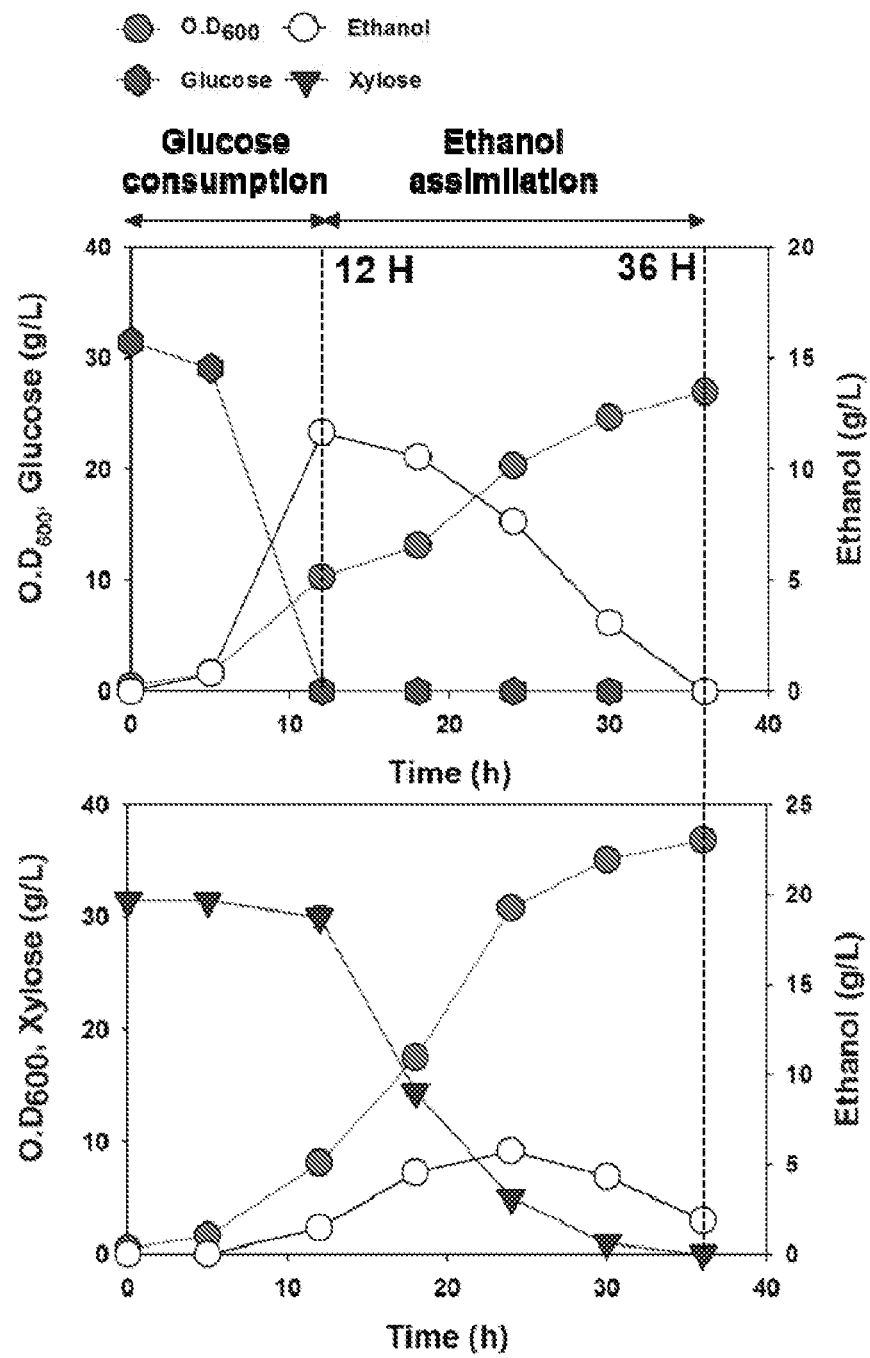
FIG. 13 shows culture profiles of CTLD strain on glucose (YPD30) and xylose (YPX30). 12h and 36h indicate glucose depletion and xylose depletion time point, respectively. The gray section indicates the ethanol assimilation phase. Error bars represent standard deviations and are not visible when smaller than the symbol size.

An engineered CTD strain was cultured on glucose and xylose to observe phenotypic changes with respect to intracellular GDP-L-fucose content. Under aerobic culture conditions, the yeast strain consumed 30 g/L of glucose within 12 h and 30 g/L of xylose within 36 h (FIG. 13). When cultured on glucose, the CTD strain quickly fermented glucose to ethanol and showed low cell mass titers. Following glucose depletion, the yeast cells continued to grow when ethanol was utilized as a carbon source. In contrast, when cultured on xylose, the CTD strain consumed xylose slower, accumulated less ethanol, and showed higher cell mass titers as compared to the glucose culture.

Figure 20:
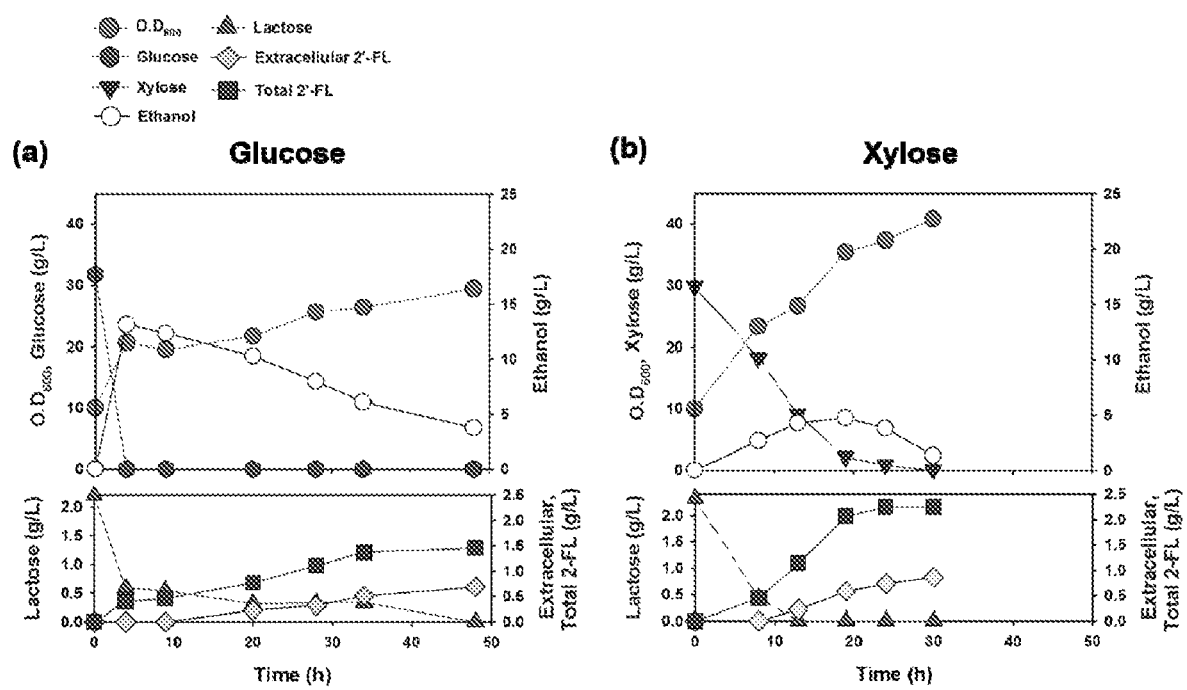
FIG. 20. Batch fermentation profiles of the engineered yeast strain (CTLD1F1) on (a) glucose and (b) xylose conditions. Results are the mean of duplicated experiment; Error bars represent standard deviations and are not visible when smaller than the symbol size.
Figure 21:
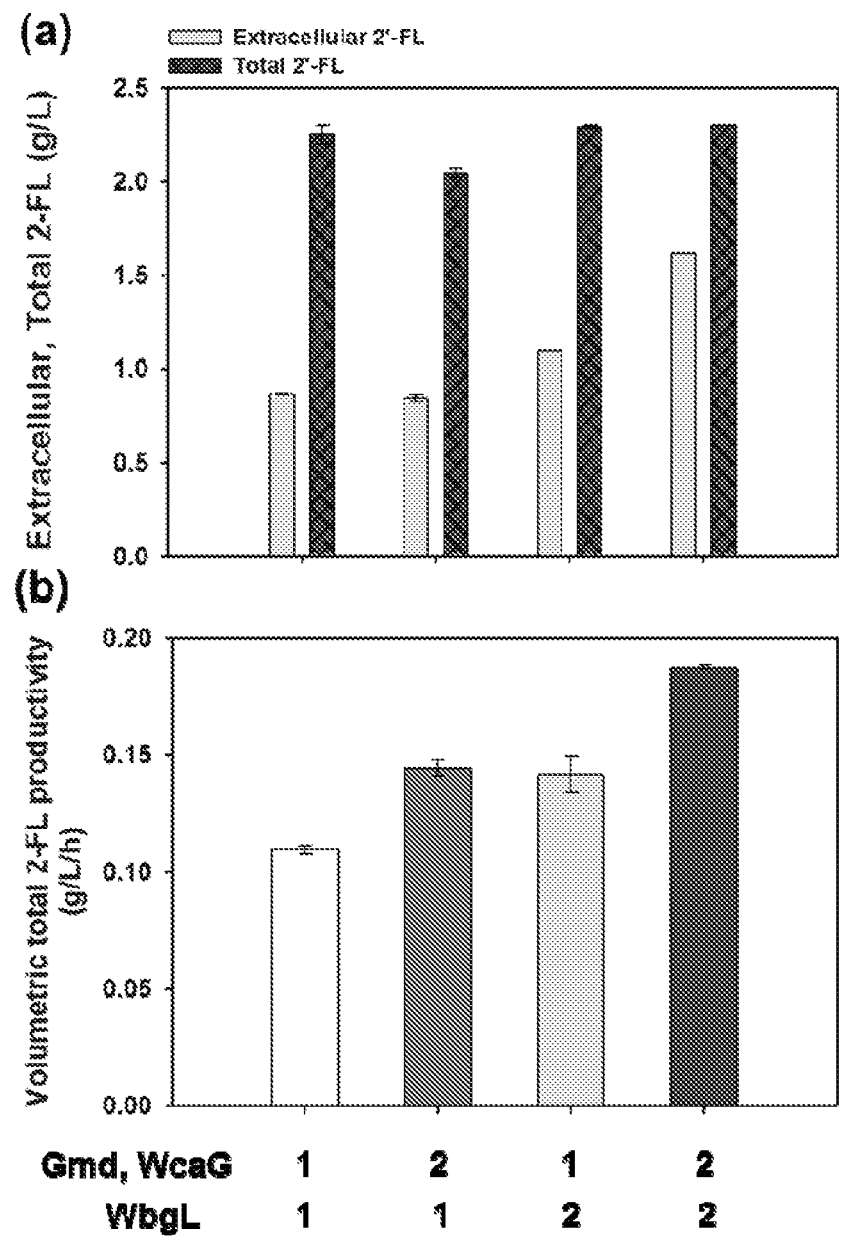
FIG. 21. Comparison of engineered yeast strains (CTLD1F1, CTLD2F1, CTLD1F2, and CTLD2F2) for (a) 2-FL production and (b) 2-FL volumetric productivity (g/L/h) on xylose condition (YPX30L2); Error bars represent standard deviations and are not visible when smaller than the symbol size.
Figure 22:
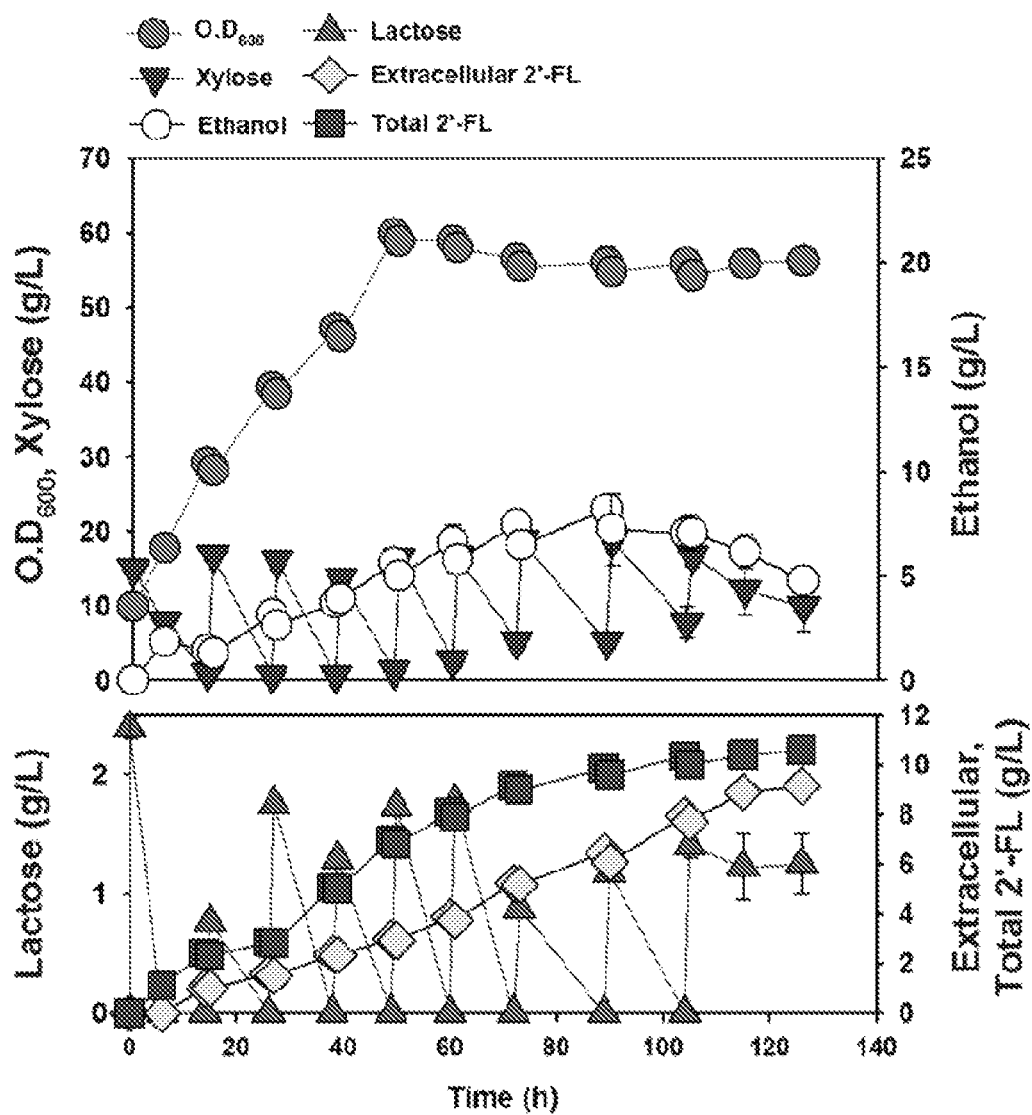
FIG. 22. Fed-batch fermentation of the CTLD2F2. When the added xylose and lactose were depleted, additional xylose and lactose were fed into the flask. Results are the mean of duplicated experiment; Error bars represent standard deviations and are not visible when smaller than the symbol size.

Intracellular GDP-L-fucose contents from the CTD strains cultured on glucose and xylose were measured after depletion of each carbon source. In particular, the glucose culture was divided into glucose consumption phase and ethanol consumption phase because the produced ethanol from glucose consumption was reassimilated and used as a carbon source for GDP-L-fucose production (FIG. 13). As a result, the CTD strain showed 0.74 mg/g and 1.02 mg/g cell of specific GDP-L-fucose content in glucose and xylose culture, respectively. The GDP-L-fucose titer of the CTD strain on xylose was 3.0-fold higher than on glucose (14.6 vs 44.1 mg GDP-L-fucose/L). Above all, it should be noted that the CTD strain showed only 0.13 mg/g cell of specific GDP-L-fucose content in the ethanol consumption phase of the glucose culture (FIG. 20). As shown in FIG. 13, cell density was significantly increased during ethanol consumption phase in the glucose culture, but the grown cells showed only low specific GDP-L-fucose content because ethanol is not a good carbon source for GDP-L-fucose production. Conversion of ethanol to fructose-6-phosphate needs to go through several steps via gluconeogenesis pathway so that the conversion efficiency is quite low. In addition, the synthesizing GDP-L-fucose requires high cellular energy (1 moles of GTP), but ethanol utilization cannot generate enough cellular energy for GDP-L-fucose production. For these reasons, sequential utilization of glucose and ethanol could not reach the level of GDP-L-fucose from xylose culture regarding both specific content and volumetric titer (FIG. 20)

Example 14. Lactose Uptake

As *S. cerevisiae* does not naturally assimilate lactose, which is a precursor for 2-FL synthesis, the introduction of a heterologous lactose transporter is necessary to produce 2-FL in *S. cerevisiae*. Therefore, LAC12 coding for lactose permease from *Kluyveromyces lactis* was integrated into the genome of the CT2 strain under the control of a constitutive promoter. It can be necessary for engineered *S. cerevisiae* to engage multiple sugars including both glucose for replenishing cellular energy and lactose for accepting the fucose moiety of GDP-L-fucose for 2-FL production.

However, among the various sugars, *Saccharomyces cerevisiae* preferentially uses glucose to other sugars because glucose triggers the inactivation of transporters and enzymes needed for catabolism of the other sugars, which process is known as catabolite repression. For example, different kinds of other sugar transporters such as maltose/$H^+$ symporter and the galactose permease (Gal2) can be inactivated in the presence of glucose. Regulation of lactose utilizing genes (Lactose transporter: LAC12, β-galactosidase: LAC4) in *K. lactis* is controlled by the same mechanisms that regulate galactose utilizing genes. Expression of the galactose-lactose (GAL/LAC) regulon in *K. lactis* is induced by lactose or galactose and repressed by glucose. Since *K. lactis* and *S. cerevisiae* share structural genes involved in the utilization of galactose (GAL/LAC regulon in *K. lactis*, or GAL/MEL in *S. cerevisiae*), it may be that the lactose transporter (LAC12) expression in *S. cerevisiae* also might be tightly regulated in the presence of glucose. While it has been reported that the LAC12 expressing engineered *S. cerevisiae* strains accumulated lactose intracellularly in glucose condition, it was speculated herein that the lactose was able to enter the cell only in the ethanol consumption phase after glucose depletion, which would make it unable to produce 2-FL during glucose consumption phase. However, in xylose condition, unlike glucose, typical catabolite repression is not observed in engineered xylose-utilizing *S. cerevisiae*. Therefore, it was hypothesized that the lactose transporter expression would not be readily repressed in the presence of xylose so that lactose can be efficiently move into cells during xylose consumption, which would be advantageous in terms of lactose availability for 2-FL production.

Figure 14:
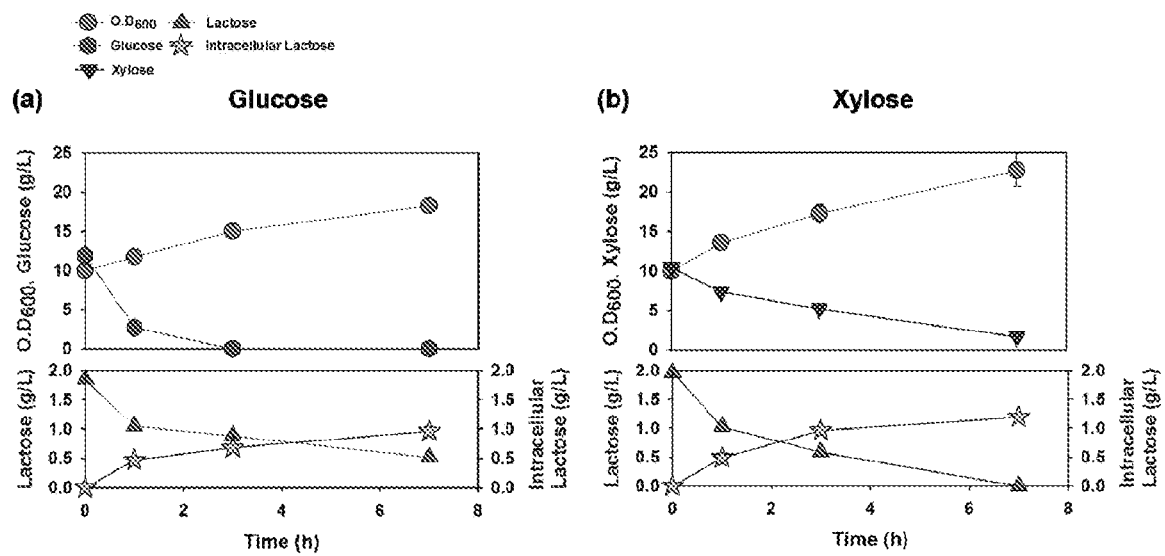
FIG. 14 shows lactose transport of the engineered yeast strain (CTL) on (a) glucose (YPD10L2) and (b) xylose conditions (YPX10L2). Results are the mean of duplicated experiment; Error bars represent standard deviations and are not visible when smaller than the symbol size.

To evaluate the functional expression of LAC12 in *S. cerevisiae* under different carbon sources conditions, the extracellular and intracellular lactose concentration of CTL were measured after incubating cells with 2 g/L lactose under glucose and xylose conditions, respectively (FIG. 14). Unexpectedly, the CTL strain assimilated lactose even under the presence of glucose. This phenomenon can be explained by the fact that *S. cerevisiae* may not have a strict regulation system that completely inhibits lactose metabolism in the presence of glucose, compared to *K. lactis*. There are two key proteins (Snf1, Mig1) for glucose repression of the galactose regulon in both strains. However, the ways in which these proteins are integrated into the regulatory circuits are unique to each regulon so that the degree to which each regulon is controlled by the two proteins is quite different. Although *S. cerevisiae* is closely related to *K. lactis* on an evolutionary time scale, the two organism have experienced different selective pressures, particularly the ways in regulate lactose metabolic genes, since *S. cerevisiae* has not evolved to utilize lactose as a carbon source. Even though glucose repression effect for lactose uptake was not significant in glucose condition, the CTL strain assimilated lactose more efficiently in xylose condition, presumably due to the absence of glucose repression for lactose transporter in the condition (FIG. 14).

Example 15. 2-FL Production

It was confirmed herein that xylose had significant advantages of GDP-L-fucose production and intracellular lactose availability, compared to glucose. To examine the positive effects of using xylose to produce 2-FL, the CTLD1F1 strain was cultured in YPD30L2 or YPX30L2, respectively. As a result, 2-FL production was observed on both conditions. In glucose condition, all glucose was consumed within 4 h, and the yeast cells continued to grow, utilizing ethanol as a carbon source after glucose depletion. All lactose was consumed for 48 hours. As a result, final total 2-FL concentration measured after lysis of cells was 1.5 g/L with a productivity of 0.04 g/L/H. The final yield of total 2-FL from lactose in the glucose condition was 0.53 mol/mol. In contrast, in xylose condition, all xylose was consumed within 30 h, the strain produced less ethanol and showed higher cell titers than the glucose condition. The consumption rate of lactose in xylose condition was much faster than in glucose condition and all lactose was consumed in 12 hours. As a result, final total 2-FL concentration measured after lysis of cells was 2.3 g/L with a productivity of 0.11 g/L/H. The final yield of total 2-FL from lactose in the xylose condition was 0.81 mol/mol.

The improved 2-FL titer and productivity by engineered yeast in xylose condition can be also explained by high energy efficiency of yeast xylose metabolism. Engineered xylose-utilizing *S. cerevisiae* can synthesize more ATP under xylose conditions due to dysregulation of glucose-dependent repression on components of oxidative phosphorylation. To efficiently produce 2-FL, an ample supply of GDP-L-fucose and intracellular lactose availability are required, but both factors require a sufficient supply of cellular energy (GTP or ATP). To synthesize ample amount of GDP-L-fucose continuously throughout the fermentation, the cells need an energy source to replenish cellular energy. However, in the glucose condition, the CTLD1F1 converted glucose to ethanol rapidly with 87% of theoretical yield, then the ethanol reassimilated into cell slowly and used as carbon source for cell growth and GDP-L-fucose production. As discussed herein, ethanol cannot generate enough cellular energy for GDP-L-fucose production so that that strains could not achieve high 2-FL titer and productivity in the ethanol consumption phase of glucose culture. Moreover, the rate of lactose assimilation in the ethanol consumption phase was significantly lower than that of xylose consumption phase because the transport of lactose requires an energy-generating system. Lactose uptake occurs via a proton symport mechanism, in which one proton is cotransported with each lactose molecule. Generally, the proton motive force that drives protons into the cell results from the transmembrane electrochemical gradient of protons (ΔP). In *Saccharomyces cerevisiae*, ΔP is generated largely by the plasma membrane ATPase, which is the major membrane protein and pumps protons out of cell with a stoichiometry of 1 proton/1 ATP. This ATPase accounts for a large proportion of ATP consumption during yeast growth, at least 10 to 15% and over 25% during fermentative growth on actively transported disaccharides such as maltose or lactose, where one proton must be pumped out for every sugar molecule entering the cell. For this reason, the rate of lactose assimilation was significantly reduced because of lack of sufficient cellular energy during ethanol consumption phase, making it also difficult to obtain high 2-FL titer and productivity in glucose condition. Taken together, using xylose as a carbon source has advantages in terms of GDP-L-fucose and intracellular lactose availability for 2-FL production. As a result, the 2-FL yield and productivity were 1.5-fold and 2.8-fold higher than the glucose condition, respectively.

Figure 19:
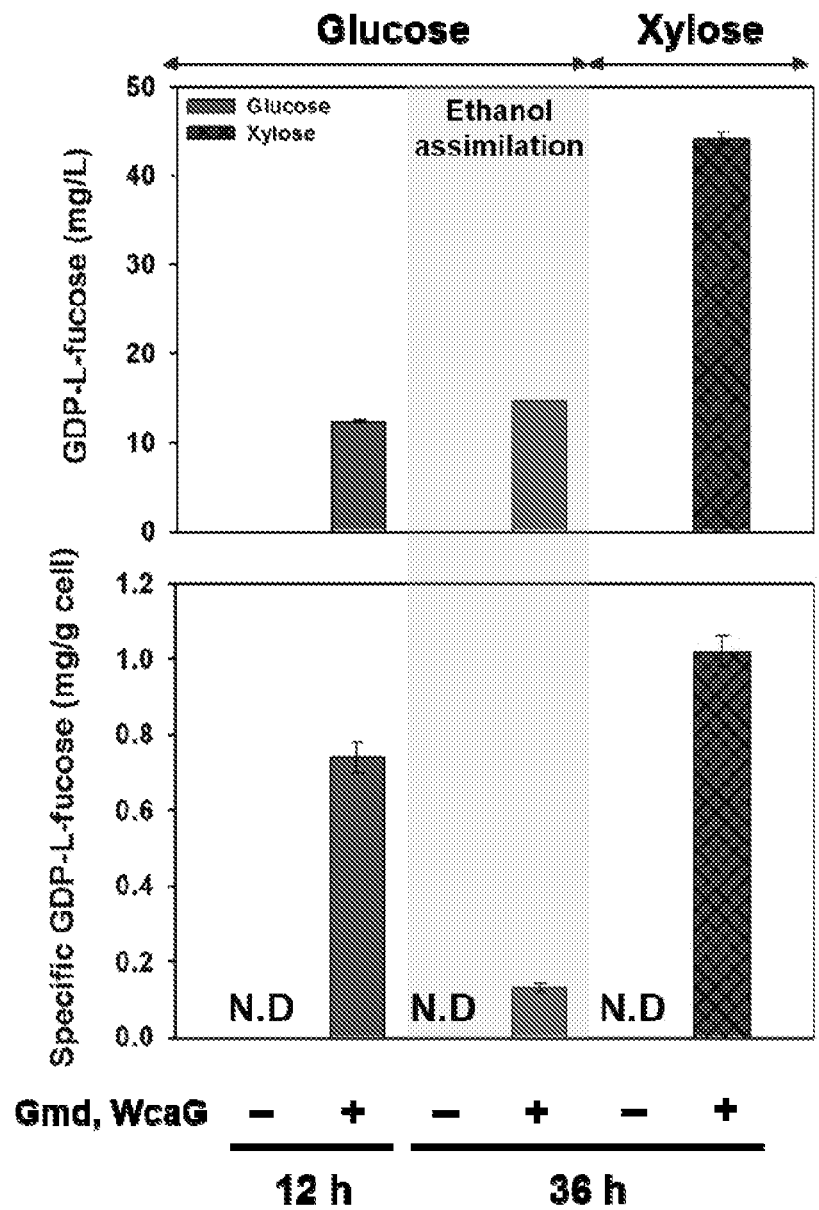
FIG. 19. GDP-L-fucose production through glucose (YPD30) and xylose (YPX30) utilization of the CTLD strain. 12h and 36h indicate glucose depletion and xylose depletion time point, respectively. The gray section indicates the ethanol assimilation phase. Error bars represent standard deviations and are not visible when smaller than the symbol size.

However, the yield of total 2-FL from lactose (0.81 mol/mol) did not reach the theoretical yield (1.0 mol/mol). As the CTLD1F1 strain had only one copy of the gmd-wcaG and wbgL genes, respectively, insufficient enzyme activities of the heterologous genes could be a reason for the result. Another reason could be intracellular 2-FL accumulation during fermentation. Furthermore, a substantial amount of intracellular 2-FL was accumulated in both conditions because *S. cerevisiae* does not have efficient 2-FL exporting system (FIG. 19). The inefficient secretion might increase the intracellular concentration of 2-FL, and the elevated 2-FL levels could potentially cause feedback inhibition on the 2-FL synthesis pathway as most biosynthetic enzymes are inhibited by the final production of the biosynthetic pathway.

Example 16. The Effects of Copy Number on 2-FL Production

To increase enzyme activity for enhancing total 2-FL yield and productivity, more copies of gmd-wcaG and wbgL genes were integrated into the CTLD1F1 chromosome. Above all, when the copy number of the genes increased, it did not lead to metabolic burden so that it had no significant effect on cell growth (data not shown). Although all strains produced similarly 2.2~2.4 g/L total 2-FL regardless of copy numbers of genes, strains harboring more gmd-wcaG and wbgL gene copies showed significantly enhanced extracellular 2-FL production. The strain CTLD2F2 that had 2 copies of gmd-wcaG and wbgL genes produced 1.6 g/L extracellular 2-FL, which was 1.7-fold higher than that of the strain CTLD1F1 (0.9 g/L extracellular 2-FL) which had only one copy of the genes under YPX30L2 condition. Interestingly, the CTLD2F2 strain was also improved 1.7-fold over the CTLD1F1 strain in terms of 2-FL productivity (0.11 vs 0.19 g/L/H). Thus, it was concluded that the 2-FL synthesis rate is positively correlated with the 2-FL secretion.

Figure 15:
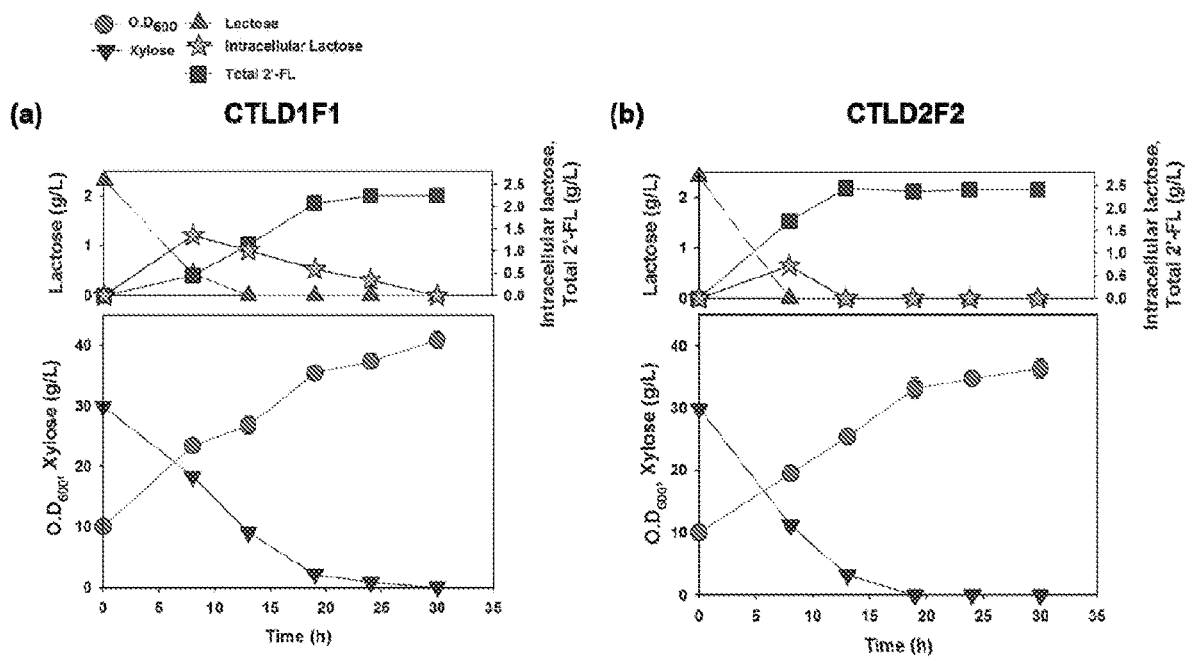
FIG. 15 shows Lactose toxicity effects of (a) CTLD1F1 strain and (b) CTLD2F2 strain on xylose condition (YPX30L2). Results are the mean of duplicated experiment; Error bars represent standard deviations and are not visible when smaller than the symbol size.

In addition, 2-FL productivity improvement has the advantage of alleviating the lactose toxicity effect by efficiently converting the intracellular lactose into 2-FL. Although the availability of intracellular lactose is important for efficient 2-FL production, an excessive accumulation of lactose in the cytosol could be toxic to engineered yeast strains carrying lactose transporter without β-galactosidase, inhibiting the uptake of carbon sources such as glucose and galactose in the engineered yeasts. As shown in FIG. 15, in the CTLD2F2 strain, intracellular lactose was efficiently converted to 2-FL so that the strain undergoes less lactose toxicity and consumed xylose efficiently during fermentation. In contrast, in the CTLD1F1 strain, the lactose toxicity was resolved to some extent through 2-FL production, but the intracellular lactose was slowly converted to 2-FL so that the xylose consumption rate of the CTLD1F1 strain was slower than that of the CTLD2F2 strain. The enhanced 2-FL productivity of the CTLD2F2 in the batch fermentation was expected to have a significant effect on fed-batch fermentation for 2-FL mass-production.

Example 17. 2-FL Production in Fed-Batch Fermentation

As the CTLD2F2 strain showed much higher extracellular 2-FL and total 2-FL productivity than other strains in the batch fermentation, a fed-batch fermentation based on xylose feeding was performed to investigate the feasibility of mass production of 2-FL by the engineered yeast. In order to increase the 2-FL titer and to reduce ethanol production, 15 g/L xylose was used instead of 30 g/L xylose, unlike the batch fermentation condition. In addition, 2× concentrated YP medium was used instead of 1X YP medium to improve the buffering capacity, which prevented dropping pH rapidly during xylose metabolism. The CTLD2F2 strain was inoculated at an initial cell OD ~10 and cultured with 15 g/L xylose and 2 g/L lactose. After the initially added xylose had been consumed, xylose concentration was maintained in the range of 15~20 g/L through intermittent feeding of 15 g/L xylose. As a result, the CTLD2F2 strain did not accumulate ethanol beyond 8.5 g/L throughout the whole fed-batch fermentation. Lactose concentration was also maintained in the range of 0.8~1.8 g/L through intermittent feeding of lactose. Finally, the $OD_{600}$ reached 57.6 (equivalent to 28.8 g/L DCW), total 10.6 g/L of 2-FL was produced with a productivity of 0.13 g/L/H, and the final yield of total 2-FL was 0.60 mol/mol from lactose. Notably, the highest 2-FL titer was obtained through shaking flask fermentation. This result greatly exceeds the titer of 0.56 g/L and productivity of 0.006 g/L/H during the batch fermentation using engineered S. cerevisiae expressing 2-FL biosynthetic pathway via episomal plasmids under glucose condition. The cell specific productivity was 0.36 g 2-FL/g cell). In addition, surprisingly about 90% of 2-FL produced was properly secreted into the medium at the end of the fed-batch fermentation.

Figure 16:
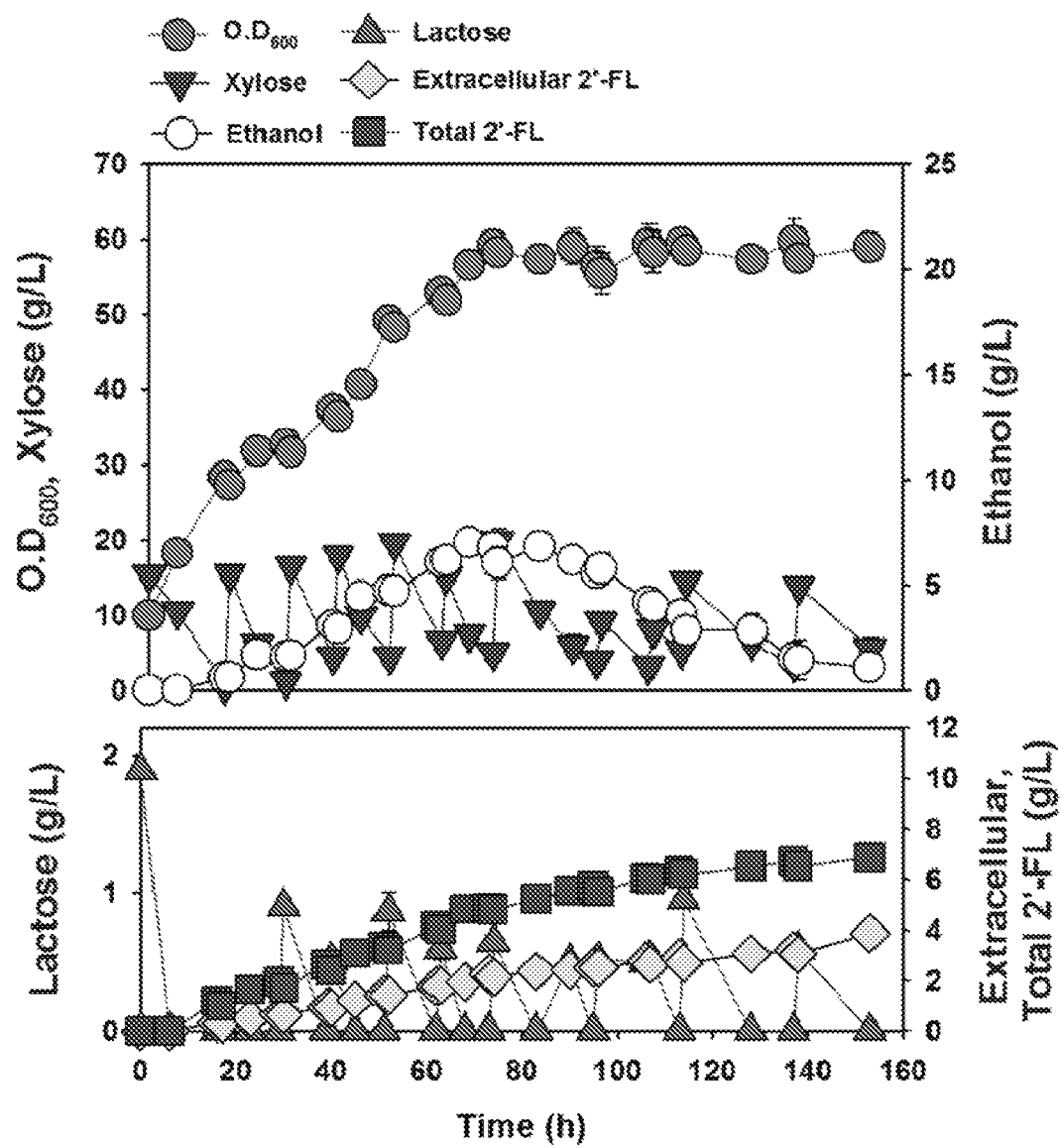
FIG. 16 shows fed-batch fermentation of the CTLD1F1. When the added xylose and lactose were depleted, additional xylose and lactose were fed into the flask. Results are the mean of duplicated experiment; Error bars represent standard deviations and are not visible when smaller than the symbol size.
Figure 17:
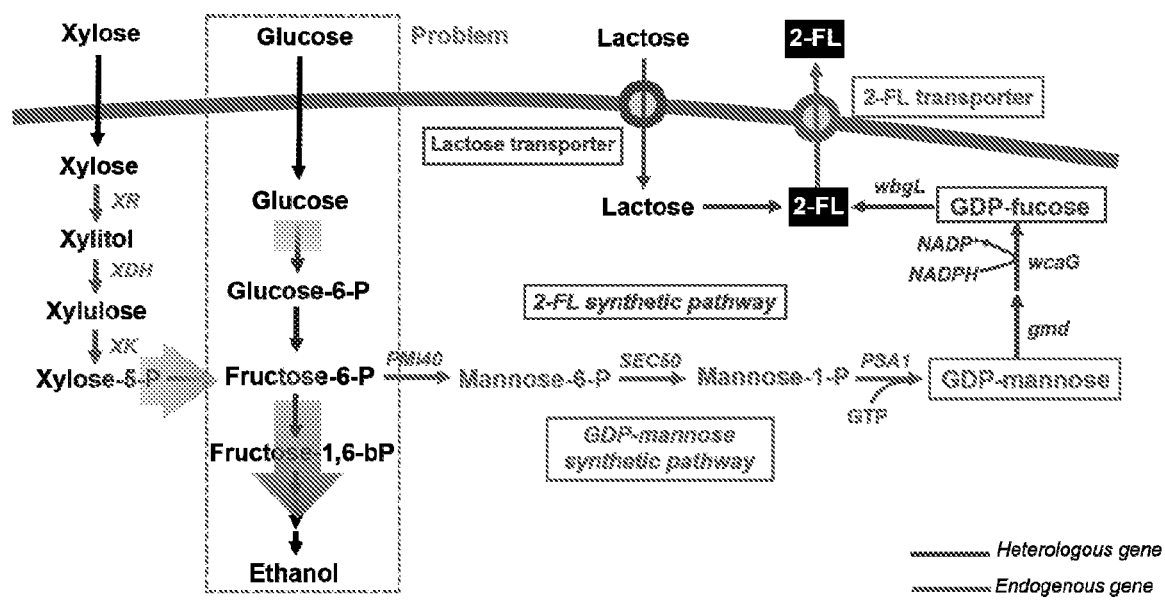
FIG. 17. Schematic diagram for 2'-FL production by engineered *S. cerevisiae*.
Figure 18:
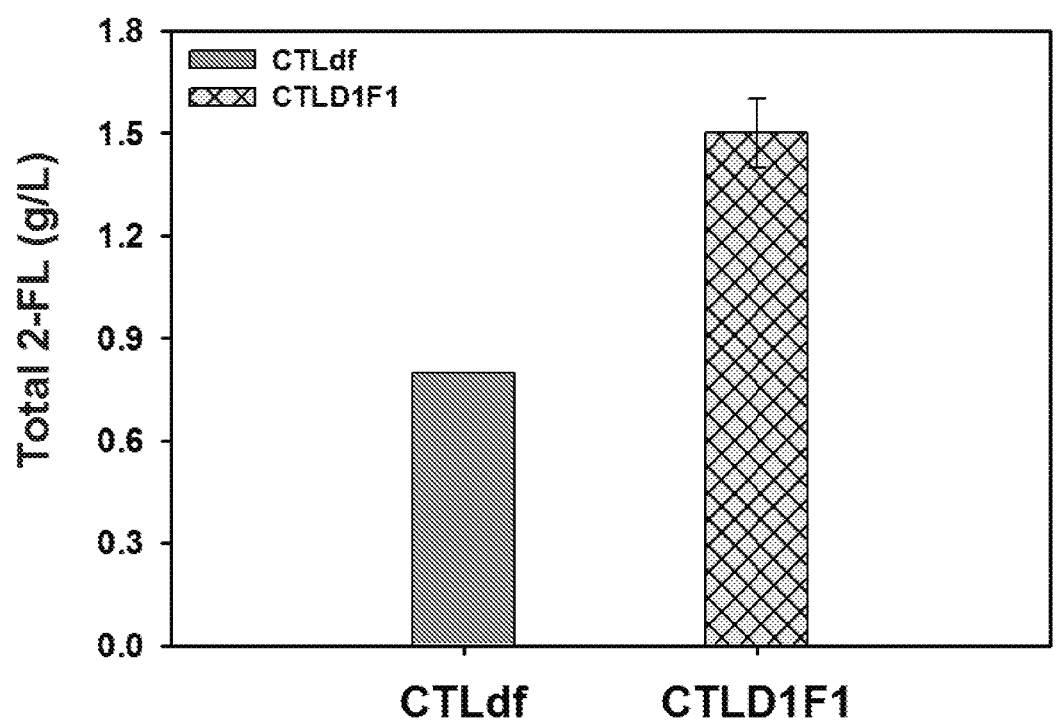
FIG. 18. Comparison of 2-FL production by CTLdf (strain carrying episomal plasmids expressing gmd-wcaG and wbgL genes) and CTLD1F1 (strain carrying chromosomal integration of gmd-wcaG and wbgL genes) in the batch fermentation (YPD30L2). Both strains were harvested after depletion of carbon source, total 2-FL was measured by HPLC. Results are the mean of duplicated experiment; Error bars represent standard deviations and are not visible when smaller than the symbol size.

One of the reasons for this high 2-FL titer in the CTLD2F2 was the enhanced 2-FL secretion due to 2-FL productivity improvement. As a result, it might help to alleviate the feedback inhibition from accumulated intracellular 2-FL on 2-FL synthesis pathway. In addition, as a certain level of 2-FL is properly secreted out of the cell, the space for 2-FL that was newly synthesized inside of cell was generated so that the total 2-FL productivity was not decreased due to the lack of space during the fed-batch fermentation. Another reason for achieving high 2-FL titer in the CTLD2F2 was the alleviation of lactose toxicity. Although the rapid lactose feeding was applied to achieve efficient 2-FL production during fed-batch fermentation, the xylose consumption rate of the CTLD2F2 strain was maintained constant without being affected by lactose toxicity as the intracellular lactose was efficiently converted to 2-FL in the strain. In order to demonstrate the alleviation of lactose toxicity effects on the final 2-FL titer, the CTLD1F1 strain was also employed for the fed-batch fermentation under the same condition as a control (FIG. 16). Finally the CTLD1F1 strain produced only 6.9 g/L total 2-FL and 3.9 g/L extracellular 2-FL, respectively, which were much lower than those of the CTLD2F2 strain. Since the CTLD1F1 strain could not efficiently convert the supplied lactose to 2-FL, some of the lactose kept remained in the cell. To alleviate the lactose toxicity in the CTLD1F1, the interval of additional lactose supply was delayed and the amount of the lactose supply was decreased (from 2 g/L to 0.5 ~1 g/L) during the fed-batch fermentation. Despite such efforts, the lactose toxicity slowed the xylose consumption rate of the CTLD1F1 strain. Once xylose utilization was not achieved well, energy production was disturbed so that the strain could not produce GDP-L-fucose efficiently. When the GDP-L-fucose production was not sufficient, the level of fucose moiety to be transferred to lactose would not be enough, which led to a decrease in overall 2-FL production and an increase intracellular lactose accumulation during the fed-batch fermentation. Taken together, the enhanced 2-FL secretion and the lactose toxicity alleviation from the improved 2-FL productivity of the CTLD2F2 strain under xylose condition significantly contributed to the high 2-FL titer in the fed-batch fermentation.

Example 18

A multitude of additional oligosaccharide transporters were tested to determine if they could transport lactose and support the production of 2-fucosyllactose. To this end, a S. cerevisiae strain expressing FucT2 and FKP was used as a host strain and putative lactose transporters were introduced as multi-copy plasmids. The transporters included CDT1, a mutant of CDT1 (CDT1M), CDT2, a mutant of CDT2, HXT2.4, a mutant of HXT2.4 (HXT2.4D), a mutant of HXT2.4 (HXT2.4L), LAC12, LAC1, LAC2, LAC3, HXT2.1, HXT2.3, HXT2.5, and HXT2.5. An empty control plasmid was transformed to construct a control strain. The putative transporter expressing strains were cultured in a minimal medium with 20 g/L of glucose, 2 g/L of fucose, and 2 g/L of lactose with an initial cell concentration of OD =1. The results are shown in FIG. 23.

Figure 23:
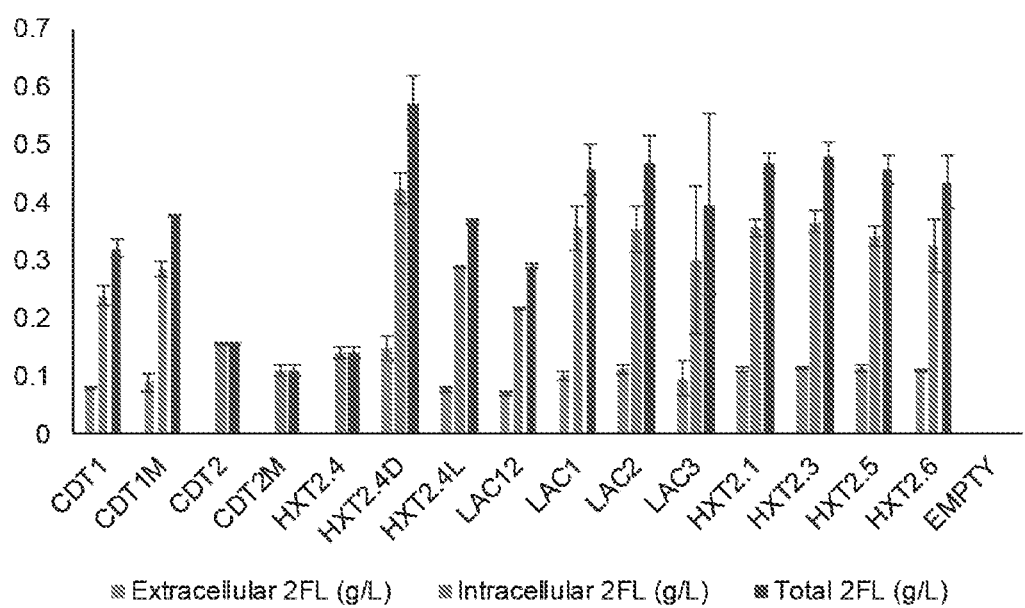
FIG. 23 shows intracellular and extracellular 2-FL produced by transformants having various oligosaccharide transporters.

The produced amounts of both intracellular and extracellular 2FL by the transformants were measured as shown in FIG. 23. As the figure showed, some transporters enhanced the production of 2-FL extracellularly. These result indicate that these transporters are capable of exporting 2-FL from the cytosol to culture media. See Table 10.

TABLE 10

| Transporter | Extracellular 2-FL (%) |
|---|---|
| CDT1 | 25.61 ± 1.65 |
| CDT1M | 23.93 ± 3.58 |
| CDT2 | 0 |
| CDT2M | 0 |
| HXT2.4 | 0 |
| HXT2.4D | 25.91 ± 1.41 |
| HXT2.4L | 21.23 ± 1.04 |
| LAC12 | 24.51 ± 0.91 |
| LAC1 | 22.11 ± 0.34 |
| LAC2 | 24.23 ± 1.25 |
| LAC3 | 24.93 ± 2.51 |
| HXT2.1 | 23.93 ± 0.54 |
| HXT2.3 | 23.77 ± 0.66 |
| HXT2.5 | 25.07 ± 0.12 |
| HXT2.6 | 25.36 ± 2.89 |
| EMPTY | 0 |

The amino acid sequence of the oligosaccharide transporters are as follows:
CDT-1 from Neurospora crassa (SEQ ID NO: 49)
MSSHGSHDGASTEKHLATHDIAPTHDAIKIVPKGHGQTATKPGAQEKEVR

NAALFAAIKESNIKPWSKESIHLYFAIFVAFCCACANGYDGSLMTGIIAM

DKFQNQFHTGDTGPKVSVIFSLYTVGAMVGAPFAAILSDRFGRKKGMFIG

-continued

GIFIIVGSIIVASSSKLAQFVVGRFVLGLGIAIMTVAAPAYSIEIAPPHW

RGRCTGFYNCGWEGGSIPAACITYGCYFIKSNWSWRIPLILQAFTCLIVM

SSVFFLPESPRELFANGRDAEAVAFLVKYHGNGDPNSKLVLLETEEMRDG

IRTDGVDKVWWDYRPLFMTHSGRWRMAQVLMISIFGQFSGNGLGYFNTVI

FKNIGVTSTSQQLAYNILNSVISAIGALTAVSMTDRMPRRAVLIIGTFMC

AAALATNSGLSATLDKQTQRGTQINLNQGMNEQDAKDNAYLHVDSNYAKG

ALAAYFLFNVIFSFTYTPLQGVIPTEALETTIRGKGLALSGFIVNAMGFI

NQFAGPIALHNIGYKYIFVFVGWDLIETVAWYFFGVESQGRTLEQLEWVY

DQPNPVKASLKVEKVVVQADGHVSEAIVA

CDT-1M (mutated CDT-1 from Neurospora crassa)

(SEQ ID NO: 50)
MSSHGSHDGASTEKHLATHDIAPTHDAIKIVPKGHGQTATKPGAQEKEVR

NAALFAAIKESNIKPWSKESIHLYFAIFVAFCCACANGYDGSLMTGIIAM

DKFQNQFHTGDTGPKVSVIFSLYTVGAMVGAPFAAILSDRFGRKKGMFIG

GIFIIVGSIIVASSSKLAQFVVGRFVLGLGIAIMTVAAPAYSIEIAPPHW

RGRCTGFYNCGWLGGSIPAACITYGCYFIKSNWSWRIPLILQAFTCLIVM

SSVFFLPESPRFLFANGRDAEAVAFLVKYHGNGDPNSKLVLLETEEMRDG

IRTDGVDKVWWDYRPLFMTHSGRWRMAQVLMISIFGQFSGNGLGYFNTVI

FKNIGVTSTSQQLAYNILNSVISAIGALTAVSMTDRMPRRAVLIIGTFMC

AAALATNSGLSATLDKQTQRGTQINLNQGMNEQDAKDNAYLHVDSNYAKG

ALAAYFLFNVIFSFTYTPLQGVIPTEALETTIRGKGLALSGFIVNAMGFI

NQFAGPIALHNIGYKYIFVFVGWDLIETVAWYFFGVESQGRTLEQLEWVY

DQPNPVKASLKVEKVVVQADGHVSEAIVA

CDT-2 from Neurospora crassa (SEQ ID NO: 51)
MGIFNKKPVAQAVDLNQIQEEAPQFERVDWKKDPGLRKLYFYAFILCIAS

ATTGYDGMFFNSVQNFETWIKYFGDPRGSELGLLGALYQIGSIGSIPFVP

LLTDNFGRKTPIIIGCVIMIVGAVLQATAKNLDTFMGGRTMLGFGNSLAQ

IASPMLLTELAHPQHRARLTTIYNCLWNVGALVVSWLAFGTNYINNDWSW

RIPALLQAFPSIIQLLGIWWVPESPRFLIAKDKHDEALHILAKYHANGDP

NHPTVQFEFREIKETIRLEMESTKNSSYLDFFKSRGNRYRLAILLSLGFF

SQWSGNAIISNYSSKLYETAGVTDSTAKLGLSAGQTGLALIVSVTMALLV

DKLGRRLAFLASTGGMCGTFVIWTLTAGLYGEHRLKGADKAMIFFIWVFG

IFYSLAWSGLLVGYAIEILPYRLRGKGLMVMNMSVQCALTLNTYANPVAF

DYFGPDHSWKLYLIYTCWIAAEFVFVFFMYVETKGPTLEELAKVIDGDEA

DVAHIDIHQVEKEVEIHEHEGKSVA

CDT-2M (mutated CDT-2 from Neurospora crassa)

(SEQ ID NO: 52)
MGIFNKKPVAQAVDLNQIQEEAPQFERVDWKKDPGLRKLYFYAFILCIAS

ATTGYDGMFFNSVQNFETWIKYFGDPRGSELGLLGALYQIGSIGSIPFVP

LLTDNFGRKTPIIIGCVIMIVGAVLQATAKNLDTFMGGRTMLGFGNSLAQ

IASPMLLTELAHPQHRARLTTIYNCLWNVGALVVSWLAFGTNYINNDWSW

RIPALLQAFPSIIQLLGIWWVPESPRFLIAKDKHDEALHILAKYHANGDP

NHPTVQFEFREIKETIRLEMESTKNSSYLDFFKSRGNRYRLAILLSLGFF

SQWSGIAIISNYSSKLYETAGVTDSTAKLGLSAGQTGLALIVSVTMALLV

DKLGRRLAFLASTGGMCGTFVIWTLTAGLYGEHRLKGADKAMIFFIWVFG

IFYSLAWSGLLVGYAIEILPYRLRGKGLMVMNMSVQCALTLNTYANPVAF

DYFGPDHSWKLYLIYTCWIAAEFVFVFFMYVETKGPTLEELAKVIDGDEA

DVAHIDIHQVEKEVEIHEHEGKSVA

HXT2.4 (wild type) from Scheffersomyces stipitis (SEQ ID NO: 53)
MSDKLHNIKDQTDSLSITDHIDEQQNILNDPNTDINDLLFQTDGWWKYGH

FRKLHFMIALIALASTNNGYDGSMLNGLQAIPDWQTTMGTPEGYKLGSLA

NGTMFGSIIAVSCASYLNDKWGRKFGVLFGSIISFIGGILQGASTNYAFF

LVARIIIGFGVGIALTGAPAWIAELSFPSYRSSCTAVFNTLWYLGAILAA

WITFGTEKLHGPKAWRIPSYLQAILPGIQVLTLWFCPESPRWLIDNGKEE

KARSVLNAYHTGNVDDERAHALVEFEIKEIKSALELEKLYASSSYFDFLK

IRSYRKRLFLVCFTAFIMQMSGNGLVSYYLVKVLRSIGYESPTEQLKING

CLQVFNIVISVGAALLTYRFKRRHQFLVCIAGMLLCYVIWTVLSAINQQR

NFEDKGLGRGILAMIFLFYFSYDIGANGLPFLYATEVLPYSHRAKGLNLM

YFTQLCTLVYNGYVNPIAMDAIEWKYYIVWCCVLAFELVIVFFFYVETFG

YTLEEVAVVFGDDAGTTLHRLSSPVEKSAVEHLEDGNSSNEKIGERV

HXT2.4D from Scheffersomyces stipites (SEQ ID NO: 54)
MSDKLHNIKDQTDSLSITDHIDEQQNILNDPNTDINDLLFQTDGWWKYGH

FRKLHFMIALIALASTNNGYDGSMLNGLQAIPDWQTTMGTPEGYKLGSLA

NGTMFGSIIAVSCASYLNDKWGRKFGVLFGSIISFIGGILQGASTNYAFF

LVARIIIGFGVGIALTGAPAWIAELSFPSYRSSCTAVFNTIWYLGAILAA

WITFGTEKLHGPKAWRIPSYLQAILPGIQVLTLWFCPESPRWLIDNGKEE

KARSVLNAYHTGNVDDERAHALVEFEIKEIKSALELEKLYDSSSYFDFLK

IRSYRKRLFLVCFTAFIMQMSGNGLVSYYLVKVLRSIGYESPTEQLKING

CLQVFNIVISVGAALLTYRFKRRHQFLVCIAGMLLCYVIWTVLSAINQQR

NFEDKGLGRGILAMIFLFYFSYDIGANGLPFLYATEVLPYSHRAKGLNLM

YFTQLCTLVYNGYVNPIAMDAIEWKYYIVWCCVLAFELVIVFFFYVETFG

YTLEEVAVVFGDDAGTTLHRLSSPVEKSAVEHLEDGNSSNEKIGERV

HXT2.4L from Scheffersomyces stipites (SEQ ID NO: 55)
MSDKLHNIKDQTDSLSITDHIDEQQNILNDPNTDINDLLFQTDGWWKYGH
FRKLHFMIALIALASTNNGYDSMLNGLQAIPDWQTTMGTPEGYKLGSLA
NGTMFGSIIAVSCASYLNDKWGRKFGVLFGSIISFIGGILQGASTNYAFF
LVARIIGFGVGIALTGAPAWIAELSFPSYRSSCTAVFNTLWYLGAILAA
WITFGTEKLHGPKAWRIPSYLQAILPGIQVLTLWFCPESPRWLIDNGKEE
KARSVLNAYHTGNVDDERAHALVEFEIKEIKSALELEKLYISSSYFDFLK
IRSYRKRLFLVCFTAFIMQMSGNGLVSYYLVKVLRSIGYESPTEQLKING
CLQVFNIVISVGAALLTYRFKRRHQFLVCIAGMLLCYVIWTVLSAINQQR
NFEDKGLGRGILAMIPLFYFSYDIGANGLPFLYATEVLPYSHRAKGLNLM
YFTQLCTIVYNGYVNPIAMDAIEWKYYIVWCCVLAFELVIVFFFYVETFG
YTLEEVAVVFGDDAGTTLHRLSSPVEKSAVEHLEDGNSSNEKIGERV LAC12 from Kluyveromyces lactis (SEQ ID NO: 56)
MADHSSSSSLQKKPINTIEHKDTLGNDRDHKEALNSDNDNTSGLKINGV
PIEDAREEVLLPGYLSKQYYKLYGLCFITYLCATMQGYDGALMGSIYTED
AYLKYYHLDINSSSGTGLVFSIFNVGQICGAFFVPLMDWKGRKPAILIGC
LGVVIGAIISSLTTTKSALIGGRWFVAFFATIANAAAPTYCAEVAPAHLR
GKVAGLYNTLWSVGSIVAAFSTYGTNKNFPNSSKAFKIPLYLQMMFPGLV
CIFGWLIPESPRWLVGVGREEEAREFIIKYHLNGDRTHPLLDMEMAEIIE
SFHGTDLSNPLEMLDVRSLFRTRSDRYRAMLVILMAWFGQFSGNNVCSYY
LPTMLRNVGMKSVSLNVLMNGVYSIVTWISSICGAFFIDKIGRREGFLGS
ISGAALALTGLSICTARYEKTKKKSASNGALVFIYLEGGIFSFAFTPMQS
MYSTEVSTNLTRSKAQLLNFVVSGVAQFVNQFATPKAMKNIKYWFYVFYV
FFDIFEFIVIYFFFVETKGRSLEELEVVFEAPNPRKASVDQAFLAQVRAT
LVQRNDVRVANAQNLKEQEPLKSDADHVEKLSEAESV HXT2.1 from Scheffersomyces stipitis (SEQ ID NO: 57)
MLHIFVFLCTLSCTTNGYDGSMLNGLQALDSWQDAMGHPEGYKLGSLANG
TIFGSVLSVSVAAWLSDKVGRRVAIIIGSGIAVVGAILQGASTNFAFFLV
SRILLGFGVGIAIASPALIAEISYPTFRPTCTTLYNTLWYLGAVIAAWV
TFGTQHLKGSASWRVPSYIQAFLPAVQFVSLWWCPESPRWMIAKGREDEA
RQILFKYHTGGDQDDRAVRLVEFEIKEIKAALEMEKICSNSKYSDFLTIP
SYRKRLFLLSFTAIIMQLSGNGLVSYYLSKVLTSIGIKSANEQLIINGCL
MIYNMVIASSVAFVVYLFRRRTLFLTSISGMLFSYIIWTALSAVNQQRDF
KDKSLGKGVLAMIFFYYLSYDIGANGLPFLYVTEILPYTHRAKGLNVMYG
VQMTTLVYNGYVNPIAMDALDWKYYIVWCCFLAFELLIVYFFFVETYGYS
LEEVAKVFGDDPNSSLIQSTSSNEKASIEHLEDTSSAEIGRVV HXT2.3 from Scheffersomyces stipites (SEQ ID NO: 58)
WWKHKHFRFLNLCIWLIALTSINNGYDSSMLNGLQSLPKWKLDMGSPVGP
VLGALNNGNTFGVMLSFLLASWIADKWGRKKAIIGGSSLMVIGAILQGVS
TNFGFFLFSRMVLGFGSGIAIVSSPSLISELAYPTHRAVATTLYNVEWYL
GAIIAAWVTFGTRTLHSSYCWRVPSYLQGFLPLVQILFFWLVPESPRYLI
ANGRTEEARAILHKHHTGSSDDERAHALINFEVSEIEAALEQEKLYSNAK
YSDFFTIPSFRMRLFLVVWTSVIMQLSGNGLVSYYLSKVLISIGITGVKE
QLEINGGINIYNLFVAGFIASNANKFKRRTLFITALSGMFITYVIWTVLS
AINQQRDFSDKSLGKGVIAMIFLFYIFYNMGANGLPWLYMTEILPYSHRA
KGVNIHNLVQTWIVIYNGFVNPIAMDAIQWKYYIVYCCIIVVELVVVYFT
YPETSGYTLEEVARAFGDDETTHLRFINETSKDKFGVEHEESVDIASKTV HXT2.5 from Scheffersomyces stipites (SEQ ID NO: 59)
ISDYVYHDQHWWKYNHFRKLHWYIFVLTLTSTNNGYDGSMLNGLQSLSTW
KDAMGNPEGYILGALANGTIFGGVLAVAFASWACDRFGRKLTTCFGSIVT
VIGAILQGASTNYAFFFVSRMVIGFGFGLASVASPTLIAELSFPTYRPTC
TALYNVFWYLGAVIAAWVTYGTRTIVSAYSWRIPSYLQGLLPLVQVCLVW
WVPESPRFLVSKGKIEKAREFLIKFHTGNDTQEQATRLVEFELKEIEAAL
EMEKINSNSKYTDFITIKTFRKRIFLVAFTACMTQLSGNGLVSYYLSKVL
ISIGITGEKEQLQINGCLMIYNLVLSLAVAFTCYLFRRKALFIFSCSFML
LSYVIWTILSAINQQRNFEQKGLGQGVLAMIFIYYLAYNIGLNGLPYLYV
TEILPYTHRAKGINLYSLVINITLIYNGFVNAIAMDAISWKYYIVYCCII
AVELVVVIFTYVETFGYTLEEVARVF HXT2.6 from Scheffersomyces stipites (SEQ ID NO: 60)
MSQSKEKSNVITTVLSEELPVKYSEEISDYVYHDQHWWKYNHFRKLHWYI
FVLTLTSTNNGYDGSMLNGLQSLSTWKDAMGNPEGYILGALANGTIFGGV
LAVAFASWACDRFGRKLTTCFGSIVTVIGAILQGASTNYAFFFVSRMVIG
FGFGLASVASPTLIAELSFPTYRPTCTALYNVFWYIGAVIAAWVTYGTRT
IVSAYSWRIPSYLQGLLPLVQVCLVWWVPESPRFLVSKGKIEKAREFLIK
FHTGNDTQEQATRLVEFELKEIEAALEMEKINSNSKYTDFITIKTFRKRI
FLVAFTACMTQLSGNGLVSYYLSKVLISIGITGEKEQLQINGCLMIYNLV
LSLAVAFTCYLFRRKALFIFSCSFMLLSYVIWTILSAINQQRNFEQKGLG
QGVLAMIFIYYLAYNIGLNGLPYLYVTEILPYTHRAKGINLYSLVINITL
IYNGFVNAIAMDAISWKYYIVYCCIIAVELVVVIFTYVETFGYTLEEVAR
VFEGTDSLAMDINLNGTVSNEKIDIVHSERGSSA LAC1 from Scheffersomyces stipites (SEQ ID NO: 61)
MSSEMLSKSEVKYEQNEMEGSQEKLALKDEDSKDFYKVNEAYNEKGFPLL
SRPMIPLLLTCSVVYFVSTNTGFDGSLMSSIYTQQDYLDKFNLSINSSTS -continued

TGLVFSIYNVAQICAAFFCPLIDFWGRKKLILIGCWGTVLGAIITAFAQN

KETLIAGRFVLSFFTTLANTSASLYVTEIANTYNRSVVAGCYNTLWYIGS

VLAAFTSYGANVNLGGTELAFRLPLGIQAVFPGLVGIFGFFIPESPRWLV

GVGREKEAEEMIAKYHCNGDFSHPLLEHEMVQINESFRGNKLAQSLKILD

LRPIFQNNNAYRSILVILMAFFGQFSGNNVCSYYLPTMIRNIGMTTVSTN

VLMNAFYSLISWFSSIAGSFAHQKVGRRKMFMFSTLAASACLTGLAVATA

RYQATSAFAASTTAIVFIYLFGVMFSFAFTPMQPIYPAEISSNVLRSRSM

IVLNITAGCAQFINQFAAPAAMENIKYWFYVFYVFWDIFECIIIYFFFVE

TKGKSLEEIDAIFEARNPRKVSVGDYSDEDGPKINWLYMRSVGQYVSRRK

SGMN

LAC2 from Scheffersomyces stipites (SEQ ID NO: 62)
MSTNSLNDSYNPSSTKEKDIVVQSEALADVAIETAFETDGYKKIFQEHPV

PRWTKSRLSIYFTCLVIYLVSTTNGYDGSLLSSLITMPEFISHLNIKSAS

GTGIVFAIFQVGQMVATLFVWLGDFIGRRNAIFIGSVIVCLGAIITSIAN

NTSTFIGGRFLLSFGSGISCALSTTYLLEITSPDERSALCAIYNSLYYIG

SIIATWSSYATSISYANSVLSFRIPLWLQILCPALVVIGLLVGVAPESPR

FYYLTGQPDKARAFFCKYHANGDEKHPIVEYEMAQLELSLLEVPKLRVRD

YFDARILFKTKSRIYRSLVCIAHSAFGQLSGNAVVGYYITNIFLELGITN

PTTRLLLNGVNSILGFIFAMSGSILVGRIGRRPILLYSTTGFVISFTIIA

ACIAAYTNNNNQVAAKVGIAFIYIFNNVFFSFGYTPLQPLYPAEILSSEM

RAKGMALFQITQGTASFINTYAAPVAMQNIKYWYYVFFVFWDTFEVIIIY

LYFVETKNLTLEEIELIFESATPVKTSMIISKPGHAANEEKLRLANLKLG

KNYVA

LAC3 from Scheffersomyces stipites (SEQ ID NO: 63)
LYTICAGLYLCSTMNGYDGSLQTAIETLPAYRTYFNLSNSASDTGLVFSI

FPAGAICATIFIWLGDYIGRVLTIIIGLVGTIVGSIVVSSTHNHSAYIGG

RFLLSFFSTIANCTAAILLTESVPYDMRWLVGCFNTFYYIGSIIATWTMY

GTSKNFEGPQTFKIGLWLQILCPGMALVLICSSALLGFGDSPRYYYGKNK

IETARDFIIKYHANGDVSHPIVAAEMEELELSFRTNGFLKPKDYLNYSNF

FRTTSNRKRTALVVAWSWFNQFSGNQVITYYMTTLFLTLGIKNATTRLLL

TGINSILCYIFATCGGLLIDRLPRRWVLLYANAGFVICFAGLAAAVRAFQ

ADANNHTAASAGIAFMYLFMTIFFSFAFTPLQPIYPAEVMSNDMRGRGMA

LYFFISNVASFVNLYSAPVAMQNIKYWYYVFFVFWDAFQFAIIYFFFVET

CALTLEEIEVVFKEKHTVKESIKFNKRKEEIMREEEITREEYTEQKTNS

---

We claim:

1. A recombinant yeast cell comprising heterologous polynucleotides encoding a GDP-mannose 4,6-dehydratase (Gmd) polypeptide, a GDP-4-keto-6-deoxymannose 3,5-epimerase 4-reductase (WcaG) polypeptide, an oligosaccharide transporter polypeptide, a fucosyltransferase polypeptide, a α-L-fucosidase polypeptide, and a L-fucokinase/GDP-L-fucose phosphorylase (FKP) polypeptide, wherein the heterologous polynucleotides are operably linked to at least one expression control polynucleotide.

2. The recombinant yeast cell of claim 1, wherein the heterologous polynucleotides are integrated into a chromosome in the recombinant yeast cell.

3. The recombinant yeast cell of claim 2, wherein two or more copies of heterologous polynucleotides encoding a GDP-mannose 4,6-dehydratase (Gmd polypeptide), GDP-4-keto-6-deoxymannose 3,5-epimerase 4-reductase (WcaG) polypeptide, an oligosaccharide transporter polypeptide, a fucosyltransferase polypeptide, and an α-L-fucosidase polypeptide are present in the recombinant yeast cell.

4. The recombinant yeast cell of claim 2, wherein the GDP-mannose 4,6-dehydratase (Gmd) polypeptide has at least 95% identity to SEQ ID NO:14, the GDP-4-keto-6-deoxymannose 3,5-epimerase 4-reductase (WcaG) polypeptide has at least 95% identity to SEQ ID NO:15, the oligosaccharide transporter polypeptide has at least 95% identity to SEQ ID NO:12, the fucosyltransferase polypeptide has at least 95% identity to SEQ ID NO:13, and the α-L-fucosidase polypeptide has at least 95% identity to SEQ ID NO:16.

5. The recombinant yeast cell of claim 2, wherein the recombinant yeast cell is Saccharomyces cerevisiae, Saccharomyces fermentad, Saccharomyces paradoxus, Saccharomyces uvarum, Saccharomyces bayanus, Schizosaccharomyces pombe, Schizosaccharomyces japonicus, Schizosaccharomyces octosporus, Schizosaccharomyces cryophilus, Torulaspora delbrueckii, Kluyveromyces marxianus, Pichia stipitis, Pichia pastoris, Pichia angusta, Zygosaccharomyces bailii, Brettanomyces intermedius, Brettanomyces bruxellensis, Brettanomyces anomalus, Brettanomyces custersianus, Brettanomyces naardenensis, Brettanomyces nanus, Dekkera bruxellensis, Dekkera anomala, Issatchenkia orientalis, Kloeckera apiculate, or Aureobasidium pullulans.

6. The recombinant yeast cell of claim 2, wherein the recombinant yeast cell is Saccharomyces cerevisiae.

7. The recombinant yeast cell of claim 1, wherein the yeast cell is Saccharomyces cerevisiae, Saccharomyces fermentati, Saccharomyces paradoxus, Saccharomyces uvarum, Saccharomyces bayanus, Schizosaccharomyces pombe, Schizosaccharomyces japonicus, Schizosaccharomyces octosporus, Schizosaccharomyces cryophilus, Torulaspora delbruecki, Kluyveromyces marxianus, Pichia stipitis, Pichia pastoris, Pichia angusta, Zygosaccharomyces bailii, Brettanomyces intermedius, Brettanomyces bruxellensis, Brettanomyces anomalus, Brettanomyces custersianus, Brettanomyces naardenensis, Brettanomyces nanus, Dekkera bruxellensis, Dekkera anomala, Issatchenkia orientalis, Kloeckera apiculate, or Aureobasidium pullulans.

8. The recombinant yeast cell of claim 1, wherein the recombinant yeast cell is Saccharomyces cerevisiae.

9. The recombinant yeast cell of claim 1, wherein the GDP-mannose 4,6-dehydratase (Gmd) polypeptide has at least 95% identity to SEQ ID NO:14, the GDP-4-keto-6-deoxymannose 3,5-epimerase 4-reductase (WcaG) polypeptide has at least 95% identity to SEQ ID NO:15, the oligosaccharide transporter polypeptide has at least 95% identity to SEQ ID NO:12, the fucosyltransferase polypeptide has at least 95% identity to SEQ ID NO:13, and the α-L-fucosidase polypeptide has at least 95% identity to SEQ ID NO:16.

10. A method for production of 2'-fucosyllactose comprising culturing the recombinant yeast cell of claim 1 in a cell culture media in the presence of lactose, wherein the recombinant yeast cell produces 2'-fucosyllactose.

11. A vector or combination of vectors comprising: a polynucleotide encoding a GDP-mannose 4,6-dehydratase (Gmd) polypeptide wherein the Gmd polypeptide has at least 95% identity to SEQ ID NO:14; a polynucleotide encoding GDP-4-keto-6-deoxymannose 3,5-epimerase 4-reductase (WcaG) polypeptide wherein the WcaG polypeptide has at least 95% identity to SEQ ID NO:15; a polynucleotide encoding a Lac12 oligosaccharide transporter; a polynucleotide encoding fucosyltransferase polypeptide wherein the fucosyltransferase polypeptide has at least 95% identity to SEQ ID NO:13, and a polynucleotide encoding an α-L-fucosidase polypeptide wherein the α-L-fucosidase polypeptide has at least 95% identity to SEQ ID NO:16, wherein the polynucleotides are operably linked to at least one expression control polynucleotide.

12. The vector or combination of vectors of claim 11 further comprising: a polynucleotide encoding a L-fucokinase/GDP-L-fucose phosphorylase polypeptide that is operably linked to at least one expression control polynucleotide.

* * * * *

SEQUENCE LISTING

<160> NUMBER OF SEQ ID NOS: 63

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 1
ataggatcca tgcaaaaact actatctttg cctcctaatc                          40

<210> SEQ ID NO 2
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 2
atagtcgact tatgatcgtg atacttggaa tcccttatcc g                       41

<210> SEQ ID NO 3
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 3
ataggatcca tgccggagcc gatctgctgt ttccttc                            37

<210> SEQ ID NO 4
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 4
atagtcgact tagcttctcg atacctgtaa tcc                              33

<210> SEQ ID NO 5
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 5
ataggatcca tgcaaaagtt attatcctta ccac                             34

<210> SEQ ID NO 6
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 6
atagtcgact tagcttcttg aaacctgaag tcccttgtca g                     41

<210> SEQ ID NO 7
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 7
tctagagcgg ccgcactagt gccaccatgg cagatcattc gagcag                46

<210> SEQ ID NO 8
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 8
tctagagcgg ccgcgtcgac ttaaacagat tctgcctctg                       40

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
actagtatgg cctttaaggt cgt                                         23

<210> SEQ ID NO 10
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 10
ccgctcgagt taggcattat acttttgaga cttaact                         37

<210> SEQ ID NO 11
<211> LENGTH: 949
<212> TYPE: PRT
<213> ORGANISM: Bacteroides fragilis

<400> SEQUENCE: 11

```
Met Gln Lys Leu Leu Ser Leu Pro Ser Asn Leu Val Gln Ser Phe His
 1               5                  10                  15

Glu Leu Glu Arg Val Asn Arg Thr Asp Trp Phe Cys Thr Ser Asp Pro
            20                  25                  30

Val Gly Lys Lys Leu Gly Ser Gly Gly Thr Ser Trp Leu Leu Glu
        35                  40                  45

Glu Cys Tyr Asn Glu Tyr Ser Asp Gly Ala Thr Phe Gly Glu Trp Leu
    50                  55                  60

Glu Lys Glu Lys Arg Ile Leu Leu His Ala Gly Gly Gln Ser Arg Arg
65                  70                  75                  80

Leu Pro Gly Tyr Ala Pro Ser Gly Lys Ile Leu Thr Pro Val Pro Val
                85                  90                  95

Phe Arg Trp Glu Arg Gly Gln His Leu Gly Gln Asn Leu Leu Ser Leu
            100                 105                 110

Gln Leu Pro Leu Tyr Glu Lys Ile Met Ser Leu Ala Pro Asp Lys Leu
        115                 120                 125

His Thr Leu Ile Ala Ser Gly Asp Val Tyr Ile Arg Ser Glu Lys Pro
    130                 135                 140

Leu Gln Ser Ile Pro Glu Ala Asp Val Val Cys Tyr Gly Leu Trp Val
145                 150                 155                 160

Asp Pro Ser Leu Ala Thr His His Gly Val Phe Ala Ser Asp Arg Lys
                165                 170                 175

His Pro Glu Gln Leu Asp Phe Met Leu Gln Lys Pro Ser Leu Ala Glu
            180                 185                 190

Leu Glu Ser Leu Ser Lys Thr His Leu Phe Leu Met Asp Ile Gly Ile
        195                 200                 205

Trp Leu Leu Ser Asp Arg Ala Val Glu Ile Leu Met Lys Arg Ser His
    210                 215                 220

Lys Glu Ser Ser Glu Glu Leu Lys Tyr Tyr Asp Leu Tyr Ser Asp Phe
225                 230                 235                 240

Gly Leu Ala Leu Gly Thr His Pro Arg Ile Glu Asp Glu Glu Val Asn
                245                 250                 255

Thr Leu Ser Val Ala Ile Leu Pro Leu Pro Gly Gly Glu Phe Tyr His
            260                 265                 270

Tyr Gly Thr Ser Lys Glu Leu Ile Ser Ser Thr Leu Ser Val Gln Asn
        275                 280                 285

Lys Val Tyr Asp Gln Arg Arg Ile Met His Arg Lys Val Lys Pro Asn
    290                 295                 300

Pro Ala Met Phe Val Gln Asn Ala Val Val Arg Ile Pro Leu Cys Ala
305                 310                 315                 320

Glu Asn Ala Asp Leu Trp Ile Glu Asn Ser His Ile Gly Pro Lys Trp
                325                 330                 335

Lys Ile Ala Ser Arg His Ile Ile Thr Gly Val Pro Glu Asn Asp Trp
            340                 345                 350

Ser Leu Ala Val Pro Ala Gly Val Cys Val Asp Val Val Pro Met Gly
```

-continued

```
                355                 360                 365
Asp Lys Gly Phe Val Ala Arg Pro Tyr Gly Leu Asp Asp Val Phe Lys
            370                 375                 380
Gly Asp Leu Arg Asp Ser Lys Thr Thr Leu Thr Gly Ile Pro Phe Gly
385                 390                 395                 400
Glu Trp Met Ser Lys Arg Gly Leu Ser Tyr Thr Asp Leu Lys Gly Arg
                405                 410                 415
Thr Asp Asp Leu Gln Ala Val Ser Val Phe Pro Met Val Asn Ser Val
            420                 425                 430
Glu Glu Leu Gly Leu Val Leu Arg Trp Met Leu Ser Glu Pro Glu Leu
            435                 440                 445
Glu Glu Gly Lys Asn Ile Trp Leu Arg Ser Glu His Phe Ser Ala Asp
            450                 455                 460
Glu Ile Ser Ala Gly Ala Asn Leu Lys Arg Leu Tyr Ala Gln Arg Glu
465                 470                 475                 480
Glu Phe Arg Lys Gly Asn Trp Lys Ala Leu Ala Val Asn His Glu Lys
                485                 490                 495
Ser Val Phe Tyr Gln Leu Asp Leu Ala Asp Ala Ala Glu Asp Phe Val
            500                 505                 510
Arg Leu Gly Leu Asp Met Pro Glu Leu Leu Pro Glu Asp Ala Leu Gln
            515                 520                 525
Met Ser Arg Ile His Asn Arg Met Leu Arg Ala Arg Ile Leu Lys Leu
            530                 535                 540
Asp Gly Lys Asp Tyr Arg Pro Glu Glu Gln Ala Ala Phe Asp Leu Leu
545                 550                 555                 560
Arg Asp Gly Leu Leu Asp Gly Ile Ser Asn Arg Lys Ser Thr Pro Lys
                565                 570                 575
Leu Asp Val Tyr Ser Asp Gln Ile Val Trp Gly Arg Ser Pro Val Arg
            580                 585                 590
Ile Asp Met Ala Gly Gly Trp Thr Asp Thr Pro Pro Tyr Ser Leu Tyr
            595                 600                 605
Ser Gly Gly Asn Val Val Asn Leu Ala Ile Glu Leu Asn Gly Gln Pro
            610                 615                 620
Pro Leu Gln Val Tyr Val Lys Pro Cys Lys Asp Phe His Ile Val Leu
625                 630                 635                 640
Arg Ser Ile Asp Met Gly Ala Met Glu Ile Val Ser Thr Phe Asp Glu
                645                 650                 655
Leu Gln Asp Tyr Lys Lys Ile Gly Ser Pro Phe Ser Ile Pro Lys Ala
            660                 665                 670
Ala Leu Ser Leu Ala Gly Phe Ala Pro Ala Phe Ser Ala Val Ser Tyr
            675                 680                 685
Ala Ser Leu Glu Glu Gln Leu Lys Asp Phe Gly Ala Gly Ile Glu Val
            690                 695                 700
Thr Leu Leu Ala Ala Ile Pro Ala Gly Ser Gly Leu Gly Thr Ser Ser
705                 710                 715                 720
Ile Leu Ala Ser Thr Val Leu Gly Ala Ile Asn Asp Phe Cys Gly Leu
                725                 730                 735
Ala Trp Asp Lys Asn Glu Ile Cys Gln Arg Thr Leu Val Leu Glu Gln
            740                 745                 750
Leu Leu Thr Thr Gly Gly Gly Trp Gln Asp Gln Tyr Gly Gly Val Leu
            755                 760                 765
Gln Gly Val Lys Leu Leu Gln Thr Glu Ala Gly Phe Ala Gln Ser Pro
            770                 775                 780
```

```
Leu Val Arg Trp Leu Pro Asp His Leu Phe Thr His Pro Glu Tyr Lys
785                 790                 795                 800

Asp Cys His Leu Leu Tyr Tyr Thr Gly Ile Thr Arg Thr Ala Lys Gly
                805                 810                 815

Ile Leu Ala Glu Ile Val Ser Ser Met Phe Leu Asn Ser Ser Leu His
            820                 825                 830

Leu Asn Leu Leu Ser Glu Met Lys Ala His Ala Leu Asp Met Asn Glu
        835                 840                 845

Ala Ile Gln Arg Gly Ser Phe Val Glu Phe Gly Arg Leu Val Gly Lys
    850                 855                 860

Thr Trp Glu Gln Asn Lys Ala Leu Asp Ser Gly Thr Asn Pro Pro Ala
865                 870                 875                 880

Val Glu Ala Ile Ile Asp Leu Ile Lys Asp Tyr Thr Leu Gly Tyr Lys
                885                 890                 895

Leu Pro Gly Ala Gly Gly Gly Tyr Leu Tyr Met Val Ala Lys Asp
            900                 905                 910

Pro Gln Ala Ala Val Arg Ile Arg Lys Ile Leu Thr Glu Asn Ala Pro
    915                 920                 925

Asn Pro Arg Ala Arg Phe Val Glu Met Thr Leu Ser Asp Lys Gly Phe
930                 935                 940

Gln Val Ser Arg Ser
945

<210> SEQ ID NO 12
<211> LENGTH: 587
<212> TYPE: PRT
<213> ORGANISM: Kluyveromyces lactis

<400> SEQUENCE: 12

Met Ala Asp His Ser Ser Ser Ser Ser Leu Gln Lys Lys Pro Ile
1               5                   10                  15

Asn Thr Ile Glu His Lys Asp Thr Leu Gly Asn Asp Arg Asp His Lys
                20                  25                  30

Glu Ala Leu Asn Ser Asp Asn Asp Asn Thr Ser Gly Leu Lys Ile Asn
            35                  40                  45

Gly Val Pro Ile Glu Asp Ala Arg Glu Glu Val Leu Leu Pro Gly Tyr
        50                  55                  60

Leu Ser Lys Gln Tyr Tyr Lys Leu Tyr Gly Leu Cys Phe Ile Thr Tyr
65                  70                  75                  80

Leu Cys Ala Thr Met Gln Gly Tyr Asp Gly Ala Leu Met Gly Ser Ile
                85                  90                  95

Tyr Thr Glu Asp Ala Tyr Leu Lys Tyr Tyr His Leu Asp Ile Asn Ser
                100                 105                 110

Ser Ser Gly Thr Gly Leu Val Phe Ser Ile Phe Asn Val Gly Gln Ile
            115                 120                 125

Cys Gly Ala Phe Phe Val Pro Leu Met Asp Trp Lys Gly Arg Lys Pro
        130                 135                 140

Ala Ile Leu Ile Gly Cys Leu Gly Val Val Ile Gly Ala Ile Ile Ser
145                 150                 155                 160

Ser Leu Thr Thr Thr Lys Ser Ala Leu Ile Gly Gly Arg Trp Phe Val
                165                 170                 175

Ala Phe Phe Ala Thr Ile Ala Asn Ala Ala Pro Thr Tyr Cys Ala
            180                 185                 190

Glu Val Ala Pro Ala His Leu Arg Gly Lys Val Ala Gly Leu Tyr Asn
```

```
                195                 200                 205
Thr Leu Trp Ser Val Gly Ser Ile Val Ala Ala Phe Ser Thr Tyr Gly
210                 215                 220

Thr Asn Lys Asn Phe Pro Asn Ser Ser Lys Ala Phe Lys Ile Pro Leu
225                 230                 235                 240

Tyr Leu Gln Met Met Phe Pro Gly Leu Val Cys Ile Phe Gly Trp Leu
                245                 250                 255

Ile Pro Glu Ser Pro Arg Trp Leu Val Gly Val Gly Arg Glu Glu
        260                 265                 270

Ala Arg Glu Phe Ile Ile Lys Tyr His Leu Asn Gly Asp Arg Thr His
            275                 280                 285

Pro Leu Leu Asp Met Glu Met Ala Glu Ile Ile Glu Ser Phe His Gly
290                 295                 300

Thr Asp Leu Ser Asn Pro Leu Glu Met Leu Asp Val Arg Ser Leu Phe
305                 310                 315                 320

Arg Thr Arg Ser Asp Arg Tyr Arg Ala Met Leu Val Ile Leu Met Ala
                325                 330                 335

Trp Phe Gly Gln Phe Ser Gly Asn Asn Val Cys Ser Tyr Tyr Leu Pro
                340                 345                 350

Thr Met Leu Arg Asn Val Gly Met Lys Ser Val Ser Leu Asn Val Leu
                355                 360                 365

Met Asn Gly Val Tyr Ser Ile Val Thr Trp Ile Ser Ile Cys Gly
370                 375                 380

Ala Phe Phe Ile Asp Lys Ile Gly Arg Arg Glu Gly Phe Leu Gly Ser
385                 390                 395                 400

Ile Ser Gly Ala Ala Leu Ala Leu Thr Gly Leu Ser Ile Cys Thr Ala
                405                 410                 415

Arg Tyr Glu Lys Thr Lys Lys Ser Ala Ser Asn Gly Ala Leu Val
                420                 425                 430

Phe Ile Tyr Leu Phe Gly Gly Ile Phe Ser Phe Ala Phe Thr Pro Met
                435                 440                 445

Gln Ser Met Tyr Ser Thr Glu Val Ser Thr Asn Leu Thr Arg Ser Lys
450                 455                 460

Ala Gln Leu Leu Asn Phe Val Val Ser Gly Val Ala Gln Phe Val Asn
465                 470                 475                 480

Gln Phe Ala Thr Pro Lys Ala Met Lys Asn Ile Lys Tyr Trp Phe Tyr
                485                 490                 495

Val Phe Tyr Val Phe Phe Asp Ile Phe Glu Phe Ile Val Ile Tyr Phe
                500                 505                 510

Phe Phe Val Glu Thr Lys Gly Arg Ser Leu Glu Glu Leu Glu Val Val
                515                 520                 525

Phe Glu Ala Pro Asn Pro Arg Lys Ala Ser Val Asp Gln Ala Phe Leu
530                 535                 540

Ala Gln Val Arg Ala Thr Leu Val Gln Arg Asn Asp Val Arg Val Ala
545                 550                 555                 560

Asn Ala Gln Asn Leu Lys Glu Gln Glu Pro Leu Lys Ser Asp Ala Asp
                565                 570                 575

His Val Glu Lys Leu Ser Glu Ala Glu Ser Val
                580                 585

<210> SEQ ID NO 13
<211> LENGTH: 300
<212> TYPE: PRT
<213> ORGANISM: Helicobacter pylori
```

<400> SEQUENCE: 13

```
Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Leu Asn Thr Pro
            20                  25                  30

Val Leu Leu Asp Thr Thr Ser Phe Asp Trp Ser Asn Arg Lys Met Gln
        35                  40                  45

Leu Glu Leu Phe Pro Ile Asp Leu Pro Tyr Ala Asn Ala Lys Glu Ile
    50                  55                  60

Ala Ile Ala Lys Met Gln His Leu Pro Lys Leu Val Arg Asp Ala Leu
65                  70                  75                  80

Lys Tyr Ile Gly Phe Asp Arg Val Ser Gln Glu Ile Val Phe Glu Tyr
                85                  90                  95

Glu Pro Lys Leu Leu Lys Pro Ser Arg Leu Thr Tyr Phe Phe Gly Tyr
            100                 105                 110

Phe Gln Asp Pro Arg Tyr Phe Asp Ala Ile Ser Ser Leu Ile Lys Gln
        115                 120                 125

Thr Phe Thr Leu Pro Pro Pro Glu Asn Asn Lys Asn Asn Asn Lys
    130                 135                 140

Lys Glu Glu Glu Tyr Gln Arg Lys Leu Ser Leu Ile Leu Ala Ala Lys
145                 150                 155                 160

Asn Ser Val Phe Val His Ile Arg Arg Gly Asp Tyr Val Gly Ile Gly
                165                 170                 175

Cys Gln Leu Gly Ile Asp Tyr Gln Lys Lys Ala Leu Glu Tyr Met Ala
            180                 185                 190

Lys Arg Val Pro Asn Met Glu Leu Phe Val Phe Cys Glu Asp Leu Lys
        195                 200                 205

Phe Thr Gln Asn Leu Asp Leu Gly Tyr Pro Phe Thr Asp Met Thr Thr
    210                 215                 220

Arg Asp Lys Glu Glu Ala Tyr Trp Asp Met Leu Leu Met Gln Ser
225                 230                 235                 240

Cys Lys His Gly Ile Ile Ala Asn Ser Thr Tyr Ser Trp Trp Ala Ala
                245                 250                 255

Tyr Leu Met Glu Asn Pro Glu Lys Ile Ile Gly Pro Lys His Trp
            260                 265                 270

Leu Phe Gly His Glu Asn Ile Leu Cys Lys Glu Trp Val Lys Ile Glu
        275                 280                 285

Ser His Phe Glu Val Lys Ser Gln Lys Tyr Asn Ala
    290                 295                 300
```

<210> SEQ ID NO 14
<211> LENGTH: 373
<212> TYPE: PRT
<213> ORGANISM: Escherichia coli

<400> SEQUENCE: 14

```
Met Ser Lys Val Ala Leu Ile Thr Gly Val Thr Gly Gln Asp Gly Ser
1               5                   10                  15

Tyr Leu Ala Glu Phe Leu Leu Glu Lys Gly Tyr Glu Val His Gly Ile
            20                  25                  30

Lys Arg Arg Ala Ser Ser Phe Asn Thr Glu Arg Val Asp His Ile Tyr
        35                  40                  45

Gln Asp Pro His Thr Cys Asn Pro Lys Phe His Leu His Tyr Gly Asp
    50                  55                  60
```

Leu Ser Asp Thr Ser Asn Leu Thr Arg Ile Leu Arg Glu Val Gln Pro
65                  70                  75                  80

Asp Glu Val Tyr Asn Leu Gly Ala Met Ser His Val Ala Val Ser Phe
                85                  90                  95

Glu Ser Pro Glu Tyr Thr Ala Asp Val Asp Ala Met Gly Thr Leu Arg
            100                 105                 110

Leu Leu Glu Ala Ile Arg Phe Leu Gly Leu Glu Lys Lys Thr Arg Phe
            115                 120                 125

Tyr Gln Ala Ser Thr Ser Glu Leu Tyr Gly Leu Val Gln Glu Ile Pro
        130                 135                 140

Gln Lys Glu Thr Thr Pro Phe Tyr Pro Arg Ser Pro Tyr Ala Val Ala
145                 150                 155                 160

Lys Leu Tyr Ala Tyr Trp Ile Thr Val Asn Tyr Arg Glu Ser Tyr Gly
                165                 170                 175

Met Tyr Ala Cys Asn Gly Ile Leu Phe Asn His Glu Ser Pro Arg Arg
            180                 185                 190

Gly Glu Thr Phe Val Thr Arg Lys Ile Thr Arg Ala Ile Ala Asn Ile
            195                 200                 205

Ala Gln Gly Leu Glu Ser Cys Leu Tyr Leu Gly Asn Met Asp Ser Leu
        210                 215                 220

Arg Asp Trp Gly His Ala Lys Asp Tyr Val Lys Met Gln Trp Met Met
225                 230                 235                 240

Leu Gln Gln Glu Gln Pro Glu Asp Phe Val Ile Ala Thr Gly Val Gln
                245                 250                 255

Tyr Ser Val Arg Gln Phe Val Glu Met Ala Ala Ala Gln Leu Gly Ile
            260                 265                 270

Lys Leu Arg Phe Glu Gly Thr Gly Val Glu Glu Lys Gly Ile Val Val
        275                 280                 285

Ser Val Thr Gly His Asp Ala Pro Gly Val Lys Pro Gly Asp Val Ile
290                 295                 300

Ile Ala Val Asp Pro Arg Tyr Phe Arg Pro Ala Glu Val Glu Thr Leu
305                 310                 315                 320

Leu Gly Asp Pro Thr Lys Ala His Glu Lys Leu Gly Trp Lys Pro Glu
            325                 330                 335

Ile Thr Leu Arg Glu Met Val Ser Glu Met Val Ala Asn Asp Leu Glu
            340                 345                 350

Ala Ala Lys Lys His Ser Leu Leu Lys Ser His Gly Tyr Asp Val Ala
        355                 360                 365

Ile Ala Leu Glu Ser
        370

<210> SEQ ID NO 15
<211> LENGTH: 321
<212> TYPE: PRT
<213> ORGANISM: Escherichia coli

<400> SEQUENCE: 15

Met Ser Lys Gln Arg Ile Phe Ile Ala Gly His Arg Gly Met Val Gly
1               5                   10                  15

Ser Ala Ile Arg Arg Gln Leu Glu Gln Arg Gly Asp Val Glu Leu Val
            20                  25                  30

Leu Arg Thr Arg Asp Glu Leu Asn Leu Leu Asp Ser Arg Ala Val His
        35                  40                  45

Asp Phe Phe Ala Ser Glu Arg Ile Asp Gln Val Tyr Leu Ala Ala Ala

```
            50                  55                  60
Lys Val Gly Gly Ile Val Ala Asn Asn Thr Tyr Pro Ala Asp Phe Ile
 65                  70                  75                  80

Tyr Gln Asn Met Met Ile Glu Ser Asn Ile Ile His Ala Ala His Gln
                     85                  90                  95

Asn Asp Val Asn Lys Leu Leu Phe Leu Gly Ser Ser Cys Ile Tyr Pro
                100                 105                 110

Lys Leu Ala Lys Gln Pro Met Ala Glu Ser Glu Leu Leu Gln Gly Thr
                115                 120                 125

Leu Glu Pro Thr Asn Glu Pro Tyr Ala Ile Ala Lys Ile Ala Gly Ile
                130                 135                 140

Lys Leu Cys Glu Ser Tyr Asn Arg Gln Tyr Gly Arg Asp Tyr Arg Ser
145                 150                 155                 160

Val Met Pro Thr Asn Leu Tyr Gly Pro His Asp Asn Phe His Pro Ser
                165                 170                 175

Asn Ser His Val Ile Pro Ala Leu Leu Arg Arg Phe His Glu Ala Thr
                180                 185                 190

Ala Gln Asn Ala Pro Asp Val Val Trp Gly Ser Gly Thr Pro Met
                195                 200                 205

Arg Glu Phe Leu His Val Asp Asp Met Val Ala Ala Ser Ile His Val
210                 215                 220

Met Glu Leu Ala His Glu Val Trp Leu Glu Asn Thr Gln Pro Met Leu
225                 230                 235                 240

Ser His Ile Asn Val Gly Thr Gly Val Asp Cys Thr Ile Arg Glu Leu
                245                 250                 255

Ala Gln Thr Ile Ala Lys Val Val Gly Tyr Lys Gly Arg Val Val Phe
                260                 265                 270

Asp Ala Ser Lys Pro Asp Gly Thr Pro Arg Lys Leu Leu Asp Val Thr
                275                 280                 285

Arg Leu His Gln Leu Gly Trp Tyr His Glu Ile Ser Leu Glu Ala Gly
                290                 295                 300

Leu Ala Ser Thr Tyr Gln Trp Phe Leu Glu Asn Gln Asp Arg Phe Arg
305                 310                 315                 320

Gly

<210> SEQ ID NO 16
<211> LENGTH: 561
<212> TYPE: PRT
<213> ORGANISM: Xanthomonas axonopodis

<400> SEQUENCE: 16

Met Thr Thr Asp Ser Arg Gln Tyr Ala Ala Pro Ser Arg Arg His Ala
 1               5                  10                  15

Gly Ala Ala Pro Arg Ser Arg Met Leu Ala Phe Ala Leu Leu Leu Ala
                20                  25                  30

Leu Pro Ala Leu His Val Thr Ala Ala Gln Ser Pro Thr Ala Pro Thr
                35                  40                  45

Ala Thr Thr Leu Ser Pro Glu Ala Ile Asp Gln Gln Trp Leu Asp Ala
 50                  55                  60

Thr Ala Lys Tyr Ala Pro Glu Arg Glu Arg Leu Val Arg Glu Ala Glu
 65                  70                  75                  80

Ala Gly Ala Arg Lys Gly Pro Phe Arg Pro Asp Trp Ala Ala Leu Lys
                85                  90                  95

Ala Tyr Gln Ser Pro Ala Trp Tyr Asp Asn Ala Lys Phe Gly Ile Phe
```

```
                100             105              110
Ile His Trp Gly Val Phe Ser Val Pro Ala Phe Gly Ser Glu Trp Tyr
            115                 120             125
Ser Arg Asn Met Tyr Leu Gln Gly Ser Lys Glu Phe Ala His His Val
    130                 135             140
Ala Thr Tyr Gly Pro Gln Ala Ser Ser Gly Tyr Lys Asp Leu Ile Pro
145                 150              155                 160
Lys Phe Thr Ala Pro Arg Phe Asp Pro Asn Gly Trp Ala Lys Leu Phe
                165                 170              175
Arg Glu Ser Gly Ala Arg Tyr Val Val Pro Val Ala Glu His His Asp
            180                 185             190
Gly Phe Ala Leu Tyr Asp Ser Lys Leu Ser Asp Trp Thr Ala Met Lys
        195                 200             205
Met Gly Pro Lys Arg Asp Leu Leu Gly Glu Leu Ser Lys Ala Ile Arg
    210                 215             220
Ala Gln Gly Leu His Phe Gly Leu Ser Ser His Arg Ala Glu His Asn
225                 230             235                 240
Trp Phe Phe Asp Gly Gly Arg Thr Phe Asp Ser Asp Val Asn Asp Pro
                245                 250             255
Arg Tyr Ala Ala Leu Tyr Gly Pro Ala Gln Val Arg Leu Pro Gly Lys
            260                 265             270
Asp Asp Ala Asp Val Ala Asn Asp Trp Thr Pro Val Ser Gln Ala Trp
        275                 280             285
Leu Asp Asp Trp Leu Ala Arg Thr Thr Glu Leu Ile Asp Thr Tyr Gln
    290                 295             300
Pro Asp Leu Ile Tyr Phe Asp Trp Trp Ile Ala His Pro Thr Phe Arg
305                 310             315                 320
Arg Ser Leu Pro Thr Met Leu Ala Tyr Tyr Asn Gln Gly Ala Ala
                325                 330             335
Arg Thr Glu Ala Asp Arg Gly Val Val Val Asn Tyr Lys Leu Gly Ala
            340                 345             350
Phe Pro Glu Gly Ala Gly Thr Leu Asp Ile Glu Arg Gly Gln Leu Thr
        355                 360             365
Gly Ile His Ser Thr His Trp Gln Thr Asp Thr Ser Val Ser Asn Ala
    370                 375             380
Ser Trp Gly Tyr Ile Glu Asn Asp Thr Tyr Lys Ser Pro Thr Phe Ile
385                 390             395                 400
Ile His Met Leu Ala Asp Val Val Ala Lys Asn Gly Asn Leu Met Leu
                405                 410             415
Asn Ile Gly Pro Arg Ala Asp Gly Ser Ile Pro Gly Thr Glu Arg Gly
            420                 425             430
Ile Leu Leu Ala Ile Gly Lys Trp Leu Lys Thr Asn Gly Cys Ala Ile
        435                 440             445
Tyr Asp Ser Lys Pro Trp Arg Val Tyr Gly Gly Pro Thr Glu Val
    450                 455             460
Val Gly Gly Thr Phe Gln Asp Ile Lys Thr Lys Pro Tyr Thr Ala Glu
465                 470             475                 480
Asp Phe Arg Phe Thr Thr Arg Asp Gly Ala Leu Tyr Ala Ile Glu Leu
                485                 490             495
Gly Trp Pro Ser Asn Gly Glu Ala Val Ile Arg Ser Leu Lys Ala Ala
            500                 505             510
Asp Gly Val Arg Ala Val Thr Leu Leu Ala Thr Gly Lys Lys Ile Pro
        515                 520             525
```

Phe Glu Gln Arg Ala Asp Gly Leu His Leu Arg Leu Pro Val Lys Pro
    530                 535                 540

Val Gly Ala Ser Ala Tyr Val Phe Arg Ile Asp Leu Ser Ser Pro Thr
545                 550                 555                 560

Pro

<210> SEQ ID NO 17
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 17
tctagagcgg ccgcactagt gccaccatgg cagatcattc gagcag                46

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 18
tctagagcgg ccgcgtcgac ttaaacagat tctgcctctg                        40

<210> SEQ ID NO 19
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 19
tctagagcgg ccgcactagt gccaccatgt caaaagtcgc tctcatcac              49

<210> SEQ ID NO 20
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 20
tctagagcgg ccgcatcgat ttatgactcc agcgcgatcg                        40

<210> SEQ ID NO 21
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 21
tctagagcgg ccgcggatcc gccaccatga gtaaacaacg agtttttatt gc          52

<210> SEQ ID NO 22
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 22

```
tctagagcgg ccgcaagctt ttaccccga aagcggtctt                    40

<210> SEQ ID NO 23
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 23
tctacagcgg ccgcggatcc gccaccatgg cctttaaggt cgtcc             45

<210> SEQ ID NO 24
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 24
tatagagcgg ccgcatcgat ggcattatac ttttgagac                    39

<210> SEQ ID NO 25
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 25
caaaattacc tacggtaatt agtgaaaggc caaaatctaa tgttacaata aattaaccct  60
cactaaaggg a                                                     71

<210> SEQ ID NO 26
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 26
gaccgttccc ttgtgttgta ccagtggtag ggttcttctc ggtagcttct gtaatacgac  60
tcactatagg gc                                                    72

<210> SEQ ID NO 27
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 27
ctcgagtcat gtaattagtt atgtcacgct tacattcacg ccctcccccc acatccgctc  60
taaccgaaaa ggaaggagtt                                            80

<210> SEQ ID NO 28
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 28
gaattcctgc agcccggggg atccactagt tctagaatcc gtcgaaacta agttctggtg  60
```

```
ttttaaaact aaaaaaaaga                                                    80

<210> SEQ ID NO 29
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 29
caccagaact tagtttcgac ggattctaga actagtggat cccccgggct gcaggaattc        60
atgaaagctg acggacctta                                                    80

<210> SEQ ID NO 30
<211> LENGTH: 80
<212> TYPE: DNA
<213> ORGANISM: Artificial Sequence
<220> FEATURE:
<223> OTHER INFORMATION: Synthetic oligonucleotide

<400> SEQUENCE: 30
gagcggatgt gggggagggg cgtgaatgta agcgtgacat aactaattac atgactcgag        60
ttagatttta gataccacaa                                                    80

<210> SEQ ID NO 31
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 31
ttcttttctt attactcttg gcctcctcta                                         30

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
ctacataaga acacctttgg tg                                                 22

<210> SEQ ID NO 33
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 33
aattgatgac aatacagacg atgataacaa                                         30

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ttagttttgc tggccgcatc                                                    20
```

<210> SEQ ID NO 35
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 35
taactattac ttgtttctat gttttagagc tagaaatagc aag        43

<210> SEQ ID NO 36
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 36
atagaaacaa gtaatagtta gatcatttat ctttcactgc gga        43

<210> SEQ ID NO 37
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 37
aacctcgagg agaagttttt ttacccctct ccacagatcc aggaaacagc tatgaccatg        60

<210> SEQ ID NO 38
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 38
taattaggta gaccgggtag attttttccgt aaccttggtg tctgtaaaac gacggccagt        60

<210> SEQ ID NO 39
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 39
caaaattacc tacggtaatt agtgaaaggc caaaatctaa tgttacaata aattaaccct        60
cactaaaggg a        71

<210> SEQ ID NO 40
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 40
gaccgttccc ttgtgttgta ccagtggtag ggttcttctc ggtagcttct gtaatacgac        60
tcactatagg gc        72

<210> SEQ ID NO 41
<211> LENGTH: 71

<212> TYPE: DNA
<213> ORGANISM: Artificial Sequence
<220> FEATURE:
<223> OTHER INFORMATION: Synthetic oligonucleotide

<400> SEQUENCE: 41
aggattcatt agtggaaaag ttcagtgaca aaatctagaa aataatatga aattaaccct    60
cactaaaggg a    71

<210> SEQ ID NO 42
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 42
gaatatagcg tatttttatt taatcacggt acaatggaga tatttgcatg gtaatacgac    60
tcactatagg gc    72

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43
gtctgccgaa attctgtg    18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44
cggtcagaaa gggaaatg    18

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 45
agtggaacat agaagggg    18

<210> SEQ ID NO 46
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 46
taagcagccc agtgaac    17

<210> SEQ ID NO 47
<211> LENGTH: 18
<212> TYPE: DNA
<213> ORGANISM: Artificial Sequence
<220> FEATURE:

<223> OTHER INFORMATION: Synthetic oligonucleotide

<400> SEQUENCE: 47
tggtaatgag gaatgcgt 18

<210> SEQ ID NO 48
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 48
cgggcattat gcgtagat 18

<210> SEQ ID NO 49
<211> LENGTH: 579
<212> TYPE: PRT
<213> ORGANISM: Neurospora crassa

<400> SEQUENCE: 49

Met Ser Ser His Gly Ser His Asp Gly Ala Ser Thr Glu Lys His Leu
1               5                   10                  15

Ala Thr His Asp Ile Ala Pro Thr His Asp Ala Ile Lys Ile Val Pro
            20                  25                  30

Lys Gly His Gly Gln Thr Ala Thr Lys Pro Gly Ala Gln Glu Lys Glu
        35                  40                  45

Val Arg Asn Ala Ala Leu Phe Ala Ala Ile Lys Glu Ser Asn Ile Lys
    50                  55                  60

Pro Trp Ser Lys Glu Ser Ile His Leu Tyr Phe Ala Ile Phe Val Ala
65                  70                  75                  80

Phe Cys Cys Ala Cys Ala Asn Gly Tyr Asp Gly Ser Leu Met Thr Gly
                85                  90                  95

Ile Ile Ala Met Asp Lys Phe Gln Asn Gln Phe His Thr Gly Asp Thr
            100                 105                 110

Gly Pro Lys Val Ser Val Ile Phe Ser Leu Tyr Thr Val Gly Ala Met
        115                 120                 125

Val Gly Ala Pro Phe Ala Ala Ile Leu Ser Asp Arg Phe Gly Arg Lys
    130                 135                 140

Lys Gly Met Phe Ile Gly Gly Ile Phe Ile Ile Val Gly Ser Ile Ile
145                 150                 155                 160

Val Ala Ser Ser Ser Lys Leu Ala Gln Phe Val Val Gly Arg Phe Val
                165                 170                 175

Leu Gly Leu Gly Ile Ala Ile Met Thr Val Ala Ala Pro Ala Tyr Ser
            180                 185                 190

Ile Glu Ile Ala Pro Pro His Trp Arg Gly Arg Cys Thr Gly Phe Tyr
        195                 200                 205

Asn Cys Gly Trp Phe Gly Gly Ser Ile Pro Ala Ala Cys Ile Thr Tyr
    210                 215                 220

Gly Cys Tyr Phe Ile Lys Ser Asn Trp Ser Trp Arg Ile Pro Leu Ile
225                 230                 235                 240

Leu Gln Ala Phe Thr Cys Leu Ile Val Met Ser Ser Val Phe Phe Leu
                245                 250                 255

Pro Glu Ser Pro Arg Phe Leu Phe Ala Asn Gly Arg Asp Ala Glu Ala
            260                 265                 270

Val Ala Phe Leu Val Lys Tyr His Gly Asn Gly Asp Pro Asn Ser Lys
        275                 280                 285

-continued

Leu Val Leu Leu Glu Thr Glu Met Arg Asp Gly Ile Arg Thr Asp
            290                 295                 300

Gly Val Asp Lys Val Trp Trp Asp Tyr Arg Pro Leu Phe Met Thr His
305                 310                 315                 320

Ser Gly Arg Trp Arg Met Ala Gln Val Leu Met Ile Ser Ile Phe Gly
                325                 330                 335

Gln Phe Ser Gly Asn Gly Leu Gly Tyr Phe Asn Thr Val Ile Phe Lys
            340                 345                 350

Asn Ile Gly Val Thr Ser Thr Ser Gln Gln Leu Ala Tyr Asn Ile Leu
            355                 360                 365

Asn Ser Val Ile Ser Ala Ile Gly Ala Leu Thr Ala Val Ser Met Thr
        370                 375                 380

Asp Arg Met Pro Arg Arg Ala Val Leu Ile Ile Gly Thr Phe Met Cys
385                 390                 395                 400

Ala Ala Ala Leu Ala Thr Asn Ser Gly Leu Ser Ala Thr Leu Asp Lys
                405                 410                 415

Gln Thr Gln Arg Gly Thr Gln Ile Asn Leu Asn Gln Gly Met Asn Glu
            420                 425                 430

Gln Asp Ala Lys Asp Asn Ala Tyr Leu His Val Asp Ser Asn Tyr Ala
        435                 440                 445

Lys Gly Ala Leu Ala Ala Tyr Phe Leu Phe Asn Val Ile Phe Ser Phe
450                 455                 460

Thr Tyr Thr Pro Leu Gln Gly Val Ile Pro Thr Glu Ala Leu Glu Thr
465                 470                 475                 480

Thr Ile Arg Gly Lys Gly Leu Ala Leu Ser Gly Phe Ile Val Asn Ala
                485                 490                 495

Met Gly Phe Ile Asn Gln Phe Ala Gly Pro Ile Ala Leu His Asn Ile
            500                 505                 510

Gly Tyr Lys Tyr Ile Phe Val Phe Val Gly Trp Asp Leu Ile Glu Thr
        515                 520                 525

Val Ala Trp Tyr Phe Phe Gly Val Glu Ser Gln Gly Arg Thr Leu Glu
530                 535                 540

Gln Leu Glu Trp Val Tyr Asp Gln Pro Asn Pro Val Lys Ala Ser Leu
545                 550                 555                 560

Lys Val Glu Lys Val Val Val Gln Ala Asp Gly His Val Ser Glu Ala
                565                 570                 575

Ile Val Ala

<210> SEQ ID NO 50
<211> LENGTH: 579
<212> TYPE: PRT
<213> ORGANISM: Neurospora crassa

<400> SEQUENCE: 50

Met Ser Ser His Gly Ser His Asp Gly Ala Ser Thr Glu Lys His Leu
1               5                   10                  15

Ala Thr His Asp Ile Ala Pro Thr His Asp Ala Ile Lys Ile Val Pro
            20                  25                  30

Lys Gly His Gly Gln Thr Ala Thr Lys Pro Gly Ala Gln Glu Lys Glu
        35                  40                  45

Val Arg Asn Ala Ala Leu Phe Ala Ala Ile Lys Glu Ser Asn Ile Lys
    50                  55                  60

Pro Trp Ser Lys Glu Ser Ile His Leu Tyr Phe Ala Ile Phe Val Ala
65                  70                  75                  80

```
Phe Cys Cys Ala Cys Ala Asn Gly Tyr Asp Gly Ser Leu Met Thr Gly
                85                  90                  95
Ile Ile Ala Met Asp Lys Phe Gln Asn Gln Phe His Thr Gly Asp Thr
            100                 105                 110
Gly Pro Lys Val Ser Val Ile Phe Ser Leu Tyr Thr Val Gly Ala Met
        115                 120                 125
Val Gly Ala Pro Phe Ala Ala Ile Leu Ser Asp Arg Phe Gly Arg Lys
    130                 135                 140
Lys Gly Met Phe Ile Gly Gly Ile Phe Ile Ile Val Gly Ser Ile Ile
145                 150                 155                 160
Val Ala Ser Ser Ser Lys Leu Ala Gln Phe Val Val Gly Arg Phe Val
                165                 170                 175
Leu Gly Leu Gly Ile Ala Ile Met Thr Val Ala Ala Pro Ala Tyr Ser
            180                 185                 190
Ile Glu Ile Ala Pro Pro His Trp Arg Gly Arg Cys Thr Gly Phe Tyr
        195                 200                 205
Asn Cys Gly Trp Leu Gly Gly Ser Ile Pro Ala Ala Cys Ile Thr Tyr
    210                 215                 220
Gly Cys Tyr Phe Ile Lys Ser Asn Trp Ser Trp Arg Ile Pro Leu Ile
225                 230                 235                 240
Leu Gln Ala Phe Thr Cys Leu Ile Val Met Ser Ser Val Phe Phe Leu
                245                 250                 255
Pro Glu Ser Pro Arg Phe Leu Phe Ala Asn Gly Arg Asp Ala Glu Ala
            260                 265                 270
Val Ala Phe Leu Val Lys Tyr His Gly Asn Gly Asp Pro Asn Ser Lys
        275                 280                 285
Leu Val Leu Leu Glu Thr Glu Glu Met Arg Asp Gly Ile Arg Thr Asp
    290                 295                 300
Gly Val Asp Lys Val Trp Trp Asp Tyr Arg Pro Leu Phe Met Thr His
305                 310                 315                 320
Ser Gly Arg Trp Arg Met Ala Gln Val Leu Met Ile Ser Ile Phe Gly
                325                 330                 335
Gln Phe Ser Gly Asn Gly Leu Gly Tyr Phe Asn Thr Val Ile Phe Lys
            340                 345                 350
Asn Ile Gly Val Thr Ser Thr Ser Gln Gln Leu Ala Tyr Asn Ile Leu
        355                 360                 365
Asn Ser Val Ile Ser Ala Ile Gly Ala Leu Thr Ala Val Ser Met Thr
    370                 375                 380
Asp Arg Met Pro Arg Arg Ala Val Leu Ile Ile Gly Thr Phe Met Cys
385                 390                 395                 400
Ala Ala Ala Leu Ala Thr Asn Ser Gly Leu Ser Ala Thr Leu Asp Lys
                405                 410                 415
Gln Thr Gln Arg Gly Thr Gln Ile Asn Leu Asn Gln Gly Met Asn Glu
            420                 425                 430
Gln Asp Ala Lys Asp Asn Ala Tyr Leu His Val Asp Ser Asn Tyr Ala
        435                 440                 445
Lys Gly Ala Leu Ala Ala Tyr Phe Leu Phe Asn Val Ile Phe Ser Phe
    450                 455                 460
Thr Tyr Thr Pro Leu Gln Gly Val Ile Pro Thr Glu Ala Leu Glu Thr
465                 470                 475                 480
Thr Ile Arg Gly Lys Gly Leu Ala Leu Ser Gly Phe Ile Val Asn Ala
                485                 490                 495
```

```
Met Gly Phe Ile Asn Gln Phe Ala Gly Pro Ile Ala Leu His Asn Ile
            500                 505                 510

Gly Tyr Lys Tyr Ile Phe Val Phe Val Gly Trp Asp Leu Ile Glu Thr
            515                 520                 525

Val Ala Trp Tyr Phe Phe Gly Val Glu Ser Gln Gly Arg Thr Leu Glu
            530                 535                 540

Gln Leu Glu Trp Val Tyr Asp Gln Pro Asn Pro Val Lys Ala Ser Leu
545                 550                 555                 560

Lys Val Glu Lys Val Val Gln Ala Asp Gly His Val Ser Glu Ala
            565                 570                 575

Ile Val Ala

<210> SEQ ID NO 51
<211> LENGTH: 525
<212> TYPE: PRT
<213> ORGANISM: Neurospora crassa

<400> SEQUENCE: 51

Met Gly Ile Phe Asn Lys Lys Pro Val Ala Gln Ala Val Asp Leu Asn
1               5                   10                  15

Gln Ile Gln Glu Glu Ala Pro Gln Phe Glu Arg Val Asp Trp Lys Lys
            20                  25                  30

Asp Pro Gly Leu Arg Lys Leu Tyr Phe Tyr Ala Phe Ile Leu Cys Ile
        35                  40                  45

Ala Ser Ala Thr Thr Gly Tyr Asp Gly Met Phe Phe Asn Ser Val Gln
    50                  55                  60

Asn Phe Glu Thr Trp Ile Lys Tyr Phe Gly Asp Pro Arg Gly Ser Glu
65                  70                  75                  80

Leu Gly Leu Leu Gly Ala Leu Tyr Gln Ile Gly Ser Ile Gly Ser Ile
                85                  90                  95

Pro Phe Val Pro Leu Leu Thr Asp Asn Phe Gly Arg Lys Thr Pro Ile
            100                 105                 110

Ile Ile Gly Cys Val Ile Met Ile Val Gly Ala Val Leu Gln Ala Thr
        115                 120                 125

Ala Lys Asn Leu Asp Thr Phe Met Gly Gly Arg Thr Met Leu Gly Phe
    130                 135                 140

Gly Asn Ser Leu Ala Gln Ile Ala Ser Pro Met Leu Leu Thr Glu Leu
145                 150                 155                 160

Ala His Pro Gln His Arg Ala Arg Leu Thr Thr Ile Tyr Asn Cys Leu
                165                 170                 175

Trp Asn Val Gly Ala Leu Val Val Ser Trp Leu Ala Phe Gly Thr Asn
            180                 185                 190

Tyr Ile Asn Asn Asp Trp Ser Trp Arg Ile Pro Ala Leu Leu Gln Ala
        195                 200                 205

Phe Pro Ser Ile Ile Gln Leu Leu Gly Ile Trp Trp Val Pro Glu Ser
    210                 215                 220

Pro Arg Phe Leu Ile Ala Lys Asp Lys His Asp Glu Ala Leu His Ile
225                 230                 235                 240

Leu Ala Lys Tyr His Ala Asn Gly Asp Pro Asn His Pro Thr Val Gln
                245                 250                 255

Phe Glu Phe Arg Glu Ile Lys Glu Thr Ile Arg Leu Glu Met Glu Ser
            260                 265                 270

Thr Lys Asn Ser Ser Tyr Leu Asp Phe Phe Lys Ser Arg Gly Asn Arg
        275                 280                 285
```

-continued

Tyr Arg Leu Ala Ile Leu Leu Ser Leu Gly Phe Phe Ser Gln Trp Ser
            290                 295                 300
Gly Asn Ala Ile Ile Ser Asn Tyr Ser Ser Lys Leu Tyr Glu Thr Ala
305                 310                 315                 320
Gly Val Thr Asp Ser Thr Ala Lys Leu Gly Leu Ser Ala Gly Gln Thr
                325                 330                 335
Gly Leu Ala Leu Ile Val Ser Val Thr Met Ala Leu Leu Val Asp Lys
            340                 345                 350
Leu Gly Arg Arg Leu Ala Phe Leu Ala Ser Thr Gly Gly Met Cys Gly
        355                 360                 365
Thr Phe Val Ile Trp Thr Leu Thr Ala Gly Leu Tyr Gly Glu His Arg
370                 375                 380
Leu Lys Gly Ala Asp Lys Ala Met Ile Phe Phe Ile Trp Val Phe Gly
385                 390                 395                 400
Ile Phe Tyr Ser Leu Ala Trp Ser Gly Leu Leu Val Gly Tyr Ala Ile
                405                 410                 415
Glu Ile Leu Pro Tyr Arg Leu Arg Gly Lys Gly Leu Met Val Met Asn
            420                 425                 430
Met Ser Val Gln Cys Ala Leu Thr Leu Asn Thr Tyr Ala Asn Pro Val
        435                 440                 445
Ala Phe Asp Tyr Phe Gly Pro Asp His Ser Trp Lys Leu Tyr Leu Ile
450                 455                 460
Tyr Thr Cys Trp Ile Ala Ala Glu Phe Val Phe Val Phe Phe Met Tyr
465                 470                 475                 480
Val Glu Thr Lys Gly Pro Thr Leu Glu Glu Leu Ala Lys Val Ile Asp
                485                 490                 495
Gly Asp Glu Ala Asp Val Ala His Ile Asp Ile His Gln Val Glu Lys
            500                 505                 510
Glu Val Glu Ile His Glu His Glu Gly Lys Ser Val Ala
        515                 520                 525

<210> SEQ ID NO 52
<211> LENGTH: 525
<212> TYPE: PRT
<213> ORGANISM: Neurospora crassa

<400> SEQUENCE: 52

Met Gly Ile Phe Asn Lys Lys Pro Val Ala Gln Ala Val Asp Leu Asn
1               5                   10                  15
Gln Ile Gln Glu Glu Ala Pro Gln Phe Glu Arg Val Asp Trp Lys Lys
            20                  25                  30
Asp Pro Gly Leu Arg Lys Leu Tyr Phe Tyr Ala Phe Ile Leu Cys Ile
        35                  40                  45
Ala Ser Ala Thr Thr Gly Tyr Asp Gly Met Phe Phe Asn Ser Val Gln
    50                  55                  60
Asn Phe Glu Thr Trp Ile Lys Tyr Phe Gly Asp Pro Arg Gly Ser Glu
65                  70                  75                  80
Leu Gly Leu Leu Gly Ala Leu Tyr Gln Ile Gly Ser Ile Gly Ser Ile
                85                  90                  95
Pro Phe Val Pro Leu Leu Thr Asp Asn Phe Gly Arg Lys Thr Pro Ile
            100                 105                 110
Ile Ile Gly Cys Val Ile Met Ile Val Gly Ala Val Leu Gln Ala Thr
        115                 120                 125
Ala Lys Asn Leu Asp Thr Phe Met Gly Gly Arg Thr Met Leu Gly Phe
    130                 135                 140

Gly Asn Ser Leu Ala Gln Ile Ala Ser Pro Met Leu Leu Thr Glu Leu
145                 150                 155                 160

Ala His Pro Gln His Arg Ala Arg Leu Thr Thr Ile Tyr Asn Cys Leu
            165                 170                 175

Trp Asn Val Gly Ala Leu Val Val Ser Trp Leu Ala Phe Gly Thr Asn
        180                 185                 190

Tyr Ile Asn Asn Asp Trp Ser Trp Arg Ile Pro Ala Leu Leu Gln Ala
    195                 200                 205

Phe Pro Ser Ile Ile Gln Leu Leu Gly Ile Trp Trp Val Pro Glu Ser
210                 215                 220

Pro Arg Phe Leu Ile Ala Lys Asp Lys His Asp Glu Ala Leu His Ile
225                 230                 235                 240

Leu Ala Lys Tyr His Ala Asn Gly Asp Pro Asn His Pro Thr Val Gln
            245                 250                 255

Phe Glu Phe Arg Glu Ile Lys Glu Thr Ile Arg Leu Glu Met Glu Ser
        260                 265                 270

Thr Lys Asn Ser Ser Tyr Leu Asp Phe Phe Lys Ser Arg Gly Asn Arg
    275                 280                 285

Tyr Arg Leu Ala Ile Leu Leu Ser Leu Gly Phe Phe Ser Gln Trp Ser
290                 295                 300

Gly Ile Ala Ile Ile Ser Asn Tyr Ser Ser Lys Leu Tyr Glu Thr Ala
305                 310                 315                 320

Gly Val Thr Asp Ser Thr Ala Lys Leu Gly Leu Ser Ala Gly Gln Thr
            325                 330                 335

Gly Leu Ala Leu Ile Val Ser Val Thr Met Ala Leu Leu Val Asp Lys
        340                 345                 350

Leu Gly Arg Arg Leu Ala Phe Leu Ala Ser Thr Gly Gly Met Cys Gly
    355                 360                 365

Thr Phe Val Ile Trp Thr Leu Thr Ala Gly Leu Tyr Gly Glu His Arg
370                 375                 380

Leu Lys Gly Ala Asp Lys Ala Met Ile Phe Phe Ile Trp Val Phe Gly
385                 390                 395                 400

Ile Phe Tyr Ser Leu Ala Trp Ser Gly Leu Leu Val Gly Tyr Ala Ile
            405                 410                 415

Glu Ile Leu Pro Tyr Arg Leu Arg Gly Lys Gly Leu Met Val Met Asn
        420                 425                 430

Met Ser Val Gln Cys Ala Leu Thr Leu Asn Thr Tyr Ala Asn Pro Val
    435                 440                 445

Ala Phe Asp Tyr Phe Gly Pro Asp His Ser Trp Lys Leu Tyr Leu Ile
450                 455                 460

Tyr Thr Cys Trp Ile Ala Ala Glu Phe Val Phe Val Phe Phe Met Tyr
465                 470                 475                 480

Val Glu Thr Lys Gly Pro Thr Leu Glu Glu Leu Ala Lys Val Ile Asp
            485                 490                 495

Gly Asp Glu Ala Asp Val Ala His Ile Asp Ile His Gln Val Glu Lys
        500                 505                 510

Glu Val Glu Ile His Glu His Glu Gly Lys Ser Val Ala
    515                 520                 525

<210> SEQ ID NO 53
<211> LENGTH: 547
<212> TYPE: PRT
<213> ORGANISM: Scheffersomyces stipitis -continued

```
<400> SEQUENCE: 53

Met Ser Asp Lys Leu His Asn Ile Lys Asp Gln Thr Asp Ser Leu Ser
1               5                   10                  15

Ile Thr Asp His Ile Asp Glu Gln Gln Asn Ile Leu Asn Asp Pro Asn
            20                  25                  30

Thr Asp Ile Asn Asp Leu Leu Phe Gln Thr Asp Gly Trp Trp Lys Tyr
        35                  40                  45

Gly His Phe Arg Lys Leu His Phe Met Ile Ala Leu Ile Ala Leu Ala
    50                  55                  60

Ser Thr Asn Asn Gly Tyr Asp Gly Ser Met Leu Asn Gly Leu Gln Ala
65                  70                  75                  80

Ile Pro Asp Trp Gln Thr Thr Met Gly Thr Pro Glu Gly Tyr Lys Leu
                85                  90                  95

Gly Ser Leu Ala Asn Gly Thr Met Phe Gly Ser Ile Ile Ala Val Ser
            100                 105                 110

Cys Ala Ser Tyr Leu Asn Asp Lys Trp Gly Arg Lys Phe Gly Val Leu
        115                 120                 125

Phe Gly Ser Ile Ile Ser Phe Ile Gly Gly Ile Leu Gln Gly Ala Ser
    130                 135                 140

Thr Asn Tyr Ala Phe Phe Leu Val Ala Arg Ile Ile Gly Phe Gly
145                 150                 155                 160

Val Gly Ile Ala Leu Thr Gly Ala Pro Ala Trp Ile Ala Glu Leu Ser
                165                 170                 175

Phe Pro Ser Tyr Arg Ser Ser Cys Thr Ala Val Phe Asn Thr Leu Trp
            180                 185                 190

Tyr Leu Gly Ala Ile Leu Ala Ala Trp Ile Thr Phe Gly Thr Glu Lys
        195                 200                 205

Leu His Gly Pro Lys Ala Trp Arg Ile Pro Ser Tyr Leu Gln Ala Ile
    210                 215                 220

Leu Pro Gly Ile Gln Val Leu Thr Leu Trp Phe Cys Pro Glu Ser Pro
225                 230                 235                 240

Arg Trp Leu Ile Asp Asn Gly Lys Glu Glu Lys Ala Arg Ser Val Leu
                245                 250                 255

Asn Ala Tyr His Thr Gly Asn Val Asp Asp Glu Arg Ala His Ala Leu
            260                 265                 270

Val Glu Phe Glu Ile Lys Glu Ile Lys Ser Ala Leu Glu Leu Glu Lys
        275                 280                 285

Leu Tyr Ala Ser Ser Ser Tyr Phe Asp Phe Leu Lys Ile Arg Ser Tyr
    290                 295                 300

Arg Lys Arg Leu Phe Leu Val Cys Phe Thr Ala Phe Ile Met Gln Met
305                 310                 315                 320

Ser Gly Asn Gly Leu Val Ser Tyr Tyr Leu Val Lys Val Leu Arg Ser
                325                 330                 335

Ile Gly Tyr Glu Ser Pro Thr Glu Gln Leu Lys Ile Asn Gly Cys Leu
            340                 345                 350

Gln Val Phe Asn Ile Val Ile Ser Val Gly Ala Ala Leu Leu Thr Tyr
        355                 360                 365

Arg Phe Lys Arg Arg His Gln Phe Leu Val Cys Ile Ala Gly Met Leu
    370                 375                 380

Leu Cys Tyr Val Ile Trp Thr Val Leu Ser Ala Ile Asn Gln Gln Arg
385                 390                 395                 400

Asn Phe Glu Asp Lys Gly Leu Gly Arg Gly Ile Leu Ala Met Ile Phe
                405                 410                 415
```

```
Leu Phe Tyr Phe Ser Tyr Asp Ile Gly Ala Asn Gly Leu Pro Phe Leu
            420                 425                 430

Tyr Ala Thr Glu Val Leu Pro Tyr Ser His Arg Ala Lys Gly Leu Asn
            435                 440                 445

Leu Met Tyr Phe Thr Gln Leu Cys Thr Leu Val Tyr Asn Gly Tyr Val
450                 455                 460

Asn Pro Ile Ala Met Asp Ala Ile Glu Trp Lys Tyr Tyr Ile Val Trp
465                 470                 475                 480

Cys Cys Val Leu Ala Phe Glu Leu Val Ile Val Phe Phe Phe Tyr Val
            485                 490                 495

Glu Thr Phe Gly Tyr Thr Leu Glu Glu Val Ala Val Val Phe Gly Asp
            500                 505                 510

Asp Ala Gly Thr Thr Leu His Arg Leu Ser Ser Pro Val Glu Lys Ser
            515                 520                 525

Ala Val Glu His Leu Glu Asp Gly Asn Ser Ser Asn Glu Lys Ile Gly
            530                 535                 540

Glu Arg Val
545

<210> SEQ ID NO 54
<211> LENGTH: 547
<212> TYPE: PRT
<213> ORGANISM: Scheffersomyces stipitis

<400> SEQUENCE: 54

Met Ser Asp Lys Leu His Asn Ile Lys Asp Gln Thr Asp Ser Leu Ser
1               5                   10                  15

Ile Thr Asp His Ile Asp Glu Gln Gln Asn Ile Leu Asn Asp Pro Asn
            20                  25                  30

Thr Asp Ile Asn Asp Leu Leu Phe Gln Thr Asp Gly Trp Trp Lys Tyr
        35                  40                  45

Gly His Phe Arg Lys Leu His Phe Met Ile Ala Leu Ile Ala Leu Ala
    50                  55                  60

Ser Thr Asn Asn Gly Tyr Asp Gly Ser Met Leu Asn Gly Leu Gln Ala
65                  70                  75                  80

Ile Pro Asp Trp Gln Thr Thr Met Gly Thr Pro Glu Gly Tyr Lys Leu
                85                  90                  95

Gly Ser Leu Ala Asn Gly Thr Met Phe Gly Ser Ile Ile Ala Val Ser
            100                 105                 110

Cys Ala Ser Tyr Leu Asn Asp Lys Trp Gly Arg Lys Phe Gly Val Leu
        115                 120                 125

Phe Gly Ser Ile Ile Ser Phe Ile Gly Gly Ile Leu Gln Gly Ala Ser
    130                 135                 140

Thr Asn Tyr Ala Phe Phe Leu Val Ala Arg Ile Ile Ile Gly Phe Gly
145                 150                 155                 160

Val Gly Ile Ala Leu Thr Gly Ala Pro Ala Trp Ile Ala Glu Leu Ser
                165                 170                 175

Phe Pro Ser Tyr Arg Ser Ser Cys Thr Ala Val Phe Asn Thr Leu Trp
            180                 185                 190

Tyr Leu Gly Ala Ile Leu Ala Ala Trp Ile Thr Phe Gly Thr Glu Lys
        195                 200                 205

Leu His Gly Pro Lys Ala Trp Arg Ile Pro Ser Tyr Leu Gln Ala Ile
    210                 215                 220

Leu Pro Gly Ile Gln Val Leu Thr Leu Trp Phe Cys Pro Glu Ser Pro
```

```
            225                 230                 235                 240
        Arg Trp Leu Ile Asp Asn Gly Lys Glu Glu Lys Ala Arg Ser Val Leu
                            245                 250                 255

Asn Ala Tyr His Thr Gly Asn Val Asp Asp Glu Arg Ala His Ala Leu
                    260                 265                 270

Val Glu Phe Glu Ile Lys Glu Ile Lys Ser Ala Leu Glu Leu Glu Lys
                    275                 280                 285

Leu Tyr Asp Ser Ser Ser Tyr Phe Asp Phe Leu Lys Ile Arg Ser Tyr
                    290                 295                 300

Arg Lys Arg Leu Phe Leu Val Cys Phe Thr Ala Phe Ile Met Gln Met
        305                 310                 315                 320

Ser Gly Asn Gly Leu Val Ser Tyr Tyr Leu Val Lys Val Leu Arg Ser
                            325                 330                 335

Ile Gly Tyr Glu Ser Pro Thr Glu Gln Leu Lys Ile Asn Gly Cys Leu
                    340                 345                 350

Gln Val Phe Asn Ile Val Ile Ser Val Gly Ala Ala Leu Leu Thr Tyr
                    355                 360                 365

Arg Phe Lys Arg Arg His Gln Phe Leu Val Cys Ile Ala Gly Met Leu
        370                 375                 380

Leu Cys Tyr Val Ile Trp Thr Val Leu Ser Ala Ile Asn Gln Gln Arg
        385                 390                 395                 400

Asn Phe Glu Asp Lys Gly Leu Gly Arg Gly Ile Leu Ala Met Ile Phe
                            405                 410                 415

Leu Phe Tyr Phe Ser Tyr Asp Ile Gly Ala Asn Gly Leu Pro Phe Leu
                    420                 425                 430

Tyr Ala Thr Glu Val Leu Pro Tyr Ser His Arg Ala Lys Gly Leu Asn
                    435                 440                 445

Leu Met Tyr Phe Thr Gln Leu Cys Thr Leu Val Tyr Asn Gly Tyr Val
                    450                 455                 460

Asn Pro Ile Ala Met Asp Ala Ile Glu Trp Lys Tyr Tyr Ile Val Trp
        465                 470                 475                 480

Cys Cys Val Leu Ala Phe Glu Leu Val Ile Val Phe Phe Tyr Val
                            485                 490                 495

Glu Thr Phe Gly Tyr Thr Leu Glu Glu Val Ala Val Phe Gly Asp
                    500                 505                 510

Asp Ala Gly Thr Thr Leu His Arg Leu Ser Ser Pro Val Glu Lys Ser
                    515                 520                 525

Ala Val Glu His Leu Glu Asp Gly Asn Ser Ser Asn Glu Lys Ile Gly
        530                 535                 540

Glu Arg Val
        545

<210> SEQ ID NO 55
<211> LENGTH: 547
<212> TYPE: PRT
<213> ORGANISM: Scheffersomyces stipitis

<400> SEQUENCE: 55

Met Ser Asp Lys Leu His Asn Ile Lys Asp Gln Thr Asp Ser Leu Ser
        1               5                   10                  15

Ile Thr Asp His Ile Asp Glu Gln Gln Asn Ile Leu Asn Asp Pro Asn
                    20                  25                  30

Thr Asp Ile Asn Asp Leu Leu Phe Gln Thr Asp Gly Trp Trp Lys Tyr
                35                  40                  45
```

-continued

```
Gly His Phe Arg Lys Leu His Phe Met Ile Ala Leu Ile Ala Leu Ala
 50              55                  60

Ser Thr Asn Asn Gly Tyr Asp Gly Ser Met Leu Asn Gly Leu Gln Ala
 65              70                  75                  80

Ile Pro Asp Trp Gln Thr Thr Met Gly Thr Pro Glu Gly Tyr Lys Leu
                 85                  90                  95

Gly Ser Leu Ala Asn Gly Thr Met Phe Gly Ser Ile Ile Ala Val Ser
                100                 105                 110

Cys Ala Ser Tyr Leu Asn Asp Lys Trp Gly Arg Lys Phe Gly Val Leu
                115                 120                 125

Phe Gly Ser Ile Ile Ser Phe Ile Gly Gly Ile Leu Gln Gly Ala Ser
130                 135                 140

Thr Asn Tyr Ala Phe Phe Leu Val Ala Arg Ile Ile Gly Phe Gly
145                 150                 155                 160

Val Gly Ile Ala Leu Thr Gly Ala Pro Ala Trp Ile Ala Glu Leu Ser
                165                 170                 175

Phe Pro Ser Tyr Arg Ser Ser Cys Thr Ala Val Phe Asn Thr Leu Trp
                180                 185                 190

Tyr Leu Gly Ala Ile Leu Ala Ala Trp Ile Thr Phe Gly Thr Glu Lys
                195                 200                 205

Leu His Gly Pro Lys Ala Trp Arg Ile Pro Ser Tyr Leu Gln Ala Ile
        210                 215                 220

Leu Pro Gly Ile Gln Val Leu Thr Leu Trp Phe Cys Pro Glu Ser Pro
225                 230                 235                 240

Arg Trp Leu Ile Asp Asn Gly Lys Glu Glu Lys Ala Arg Ser Val Leu
                245                 250                 255

Asn Ala Tyr His Thr Gly Asn Val Asp Asp Glu Arg Ala His Ala Leu
                260                 265                 270

Val Glu Phe Glu Ile Lys Glu Ile Lys Ser Ala Leu Glu Leu Glu Lys
            275                 280                 285

Leu Tyr Leu Ser Ser Ser Tyr Phe Asp Phe Leu Lys Ile Arg Ser Tyr
        290                 295                 300

Arg Lys Arg Leu Phe Leu Val Cys Phe Thr Ala Phe Ile Met Gln Met
305                 310                 315                 320

Ser Gly Asn Gly Leu Val Ser Tyr Tyr Leu Val Lys Val Leu Arg Ser
                325                 330                 335

Ile Gly Tyr Glu Ser Pro Thr Glu Gln Leu Lys Ile Asn Gly Cys Leu
                340                 345                 350

Gln Val Phe Asn Ile Val Ile Ser Val Gly Ala Ala Leu Leu Thr Tyr
                355                 360                 365

Arg Phe Lys Arg Arg His Gln Phe Leu Val Cys Ile Ala Gly Met Leu
        370                 375                 380

Leu Cys Tyr Val Ile Trp Thr Val Leu Ser Ala Ile Asn Gln Gln Arg
385                 390                 395                 400

Asn Phe Glu Asp Lys Gly Leu Gly Arg Gly Ile Leu Ala Met Ile Phe
                405                 410                 415

Leu Phe Tyr Phe Ser Tyr Asp Ile Gly Ala Asn Gly Leu Pro Phe Leu
                420                 425                 430

Tyr Ala Thr Glu Val Leu Pro Tyr Ser His Arg Ala Lys Gly Leu Asn
            435                 440                 445

Leu Met Tyr Phe Thr Gln Leu Cys Thr Leu Val Tyr Asn Gly Tyr Val
450                 455                 460

Asn Pro Ile Ala Met Asp Ala Ile Glu Trp Lys Tyr Tyr Ile Val Trp
```

```
             465                 470                 475                 480
Cys Cys Val Leu Ala Phe Glu Leu Val Ile Val Phe Phe Tyr Val
                485                 490                 495

Glu Thr Phe Gly Tyr Thr Leu Glu Glu Val Ala Val Val Phe Gly Asp
                500                 505                 510

Asp Ala Gly Thr Thr Leu His Arg Leu Ser Ser Pro Val Glu Lys Ser
                515                 520                 525

Ala Val Glu His Leu Glu Asp Gly Asn Ser Ser Asn Glu Lys Ile Gly
530                 535                 540

Glu Arg Val
545

<210> SEQ ID NO 56
<211> LENGTH: 587
<212> TYPE: PRT
<213> ORGANISM: Kluyveromyces lactis

<400> SEQUENCE: 56

Met Ala Asp His Ser Ser Ser Ser Ser Leu Gln Lys Lys Pro Ile
1               5                   10                  15

Asn Thr Ile Glu His Lys Asp Thr Leu Gly Asn Asp Arg Asp His Lys
                20                  25                  30

Glu Ala Leu Asn Ser Asp Asn Asp Thr Ser Gly Leu Lys Ile Asn
            35                  40                  45

Gly Val Pro Ile Glu Asp Ala Arg Glu Val Leu Leu Pro Gly Tyr
        50                  55                  60

Leu Ser Lys Gln Tyr Tyr Lys Leu Tyr Gly Leu Cys Phe Ile Thr Tyr
65                  70                  75                  80

Leu Cys Ala Thr Met Gln Gly Tyr Asp Gly Ala Leu Met Gly Ser Ile
                85                  90                  95

Tyr Thr Glu Asp Ala Tyr Leu Lys Tyr His Leu Asp Ile Asn Ser
                100                 105                 110

Ser Ser Gly Thr Gly Leu Val Phe Ser Ile Phe Asn Val Gly Gln Ile
            115                 120                 125

Cys Gly Ala Phe Phe Val Pro Leu Met Asp Trp Lys Gly Arg Lys Pro
130                 135                 140

Ala Ile Leu Ile Gly Cys Leu Gly Val Val Ile Gly Ala Ile Ile Ser
145                 150                 155                 160

Ser Leu Thr Thr Thr Lys Ser Ala Leu Ile Gly Gly Arg Trp Phe Val
                165                 170                 175

Ala Phe Phe Ala Thr Ile Ala Asn Ala Ala Pro Thr Tyr Cys Ala
            180                 185                 190

Glu Val Ala Pro Ala His Leu Arg Gly Lys Val Ala Gly Leu Tyr Asn
            195                 200                 205

Thr Leu Trp Ser Val Gly Ser Ile Val Ala Ala Phe Ser Thr Tyr Gly
        210                 215                 220

Thr Asn Lys Asn Phe Pro Asn Ser Ser Lys Ala Phe Lys Ile Pro Leu
225                 230                 235                 240

Tyr Leu Gln Met Met Phe Pro Gly Leu Val Cys Ile Phe Gly Trp Leu
                245                 250                 255

Ile Pro Glu Ser Pro Arg Trp Leu Val Gly Val Gly Arg Glu Glu
                260                 265                 270

Ala Arg Glu Phe Ile Ile Lys Tyr His Leu Asn Gly Asp Arg Thr His
            275                 280                 285
```

Pro Leu Leu Asp Met Glu Met Ala Glu Ile Ile Glu Ser Phe His Gly
    290                 295                 300

Thr Asp Leu Ser Asn Pro Leu Glu Met Leu Asp Val Arg Ser Leu Phe
305                 310                 315                 320

Arg Thr Arg Ser Asp Arg Tyr Arg Ala Met Leu Val Ile Leu Met Ala
                325                 330                 335

Trp Phe Gly Gln Phe Ser Gly Asn Asn Val Cys Ser Tyr Tyr Leu Pro
            340                 345                 350

Thr Met Leu Arg Asn Val Gly Met Lys Ser Val Ser Leu Asn Val Leu
            355                 360                 365

Met Asn Gly Val Tyr Ser Ile Val Thr Trp Ile Ser Ser Ile Cys Gly
370                 375                 380

Ala Phe Phe Ile Asp Lys Ile Gly Arg Arg Glu Gly Phe Leu Gly Ser
385                 390                 395                 400

Ile Ser Gly Ala Ala Leu Ala Leu Thr Gly Leu Ser Ile Cys Thr Ala
                405                 410                 415

Arg Tyr Glu Lys Thr Lys Lys Ser Ala Ser Asn Gly Ala Leu Val
                420                 425                 430

Phe Ile Tyr Leu Phe Gly Gly Ile Phe Ser Phe Ala Phe Thr Pro Met
            435                 440                 445

Gln Ser Met Tyr Ser Thr Glu Val Ser Thr Asn Leu Thr Arg Ser Lys
450                 455                 460

Ala Gln Leu Leu Asn Phe Val Val Ser Gly Val Ala Gln Phe Val Asn
465                 470                 475                 480

Gln Phe Ala Thr Pro Lys Ala Met Lys Asn Ile Lys Tyr Trp Phe Tyr
                485                 490                 495

Val Phe Tyr Val Phe Phe Asp Ile Phe Glu Phe Ile Val Ile Tyr Phe
            500                 505                 510

Phe Phe Val Glu Thr Lys Gly Arg Ser Leu Glu Glu Leu Glu Val Val
            515                 520                 525

Phe Glu Ala Pro Asn Pro Arg Lys Ala Ser Val Asp Gln Ala Phe Leu
            530                 535                 540

Ala Gln Val Arg Ala Thr Leu Val Gln Arg Asn Asp Val Arg Val Ala
545                 550                 555                 560

Asn Ala Gln Asn Leu Lys Glu Gln Pro Leu Lys Ser Asp Ala Asp
                565                 570                 575

His Val Glu Lys Leu Ser Glu Ala Glu Ser Val
            580                 585

<210> SEQ ID NO 57
<211> LENGTH: 493
<212> TYPE: PRT
<213> ORGANISM: Scheffersomyces stipitis

<400> SEQUENCE: 57

Met Leu His Ile Phe Val Phe Leu Cys Thr Leu Ser Cys Thr Thr Asn
1               5                   10                  15

Gly Tyr Asp Gly Ser Met Leu Asn Gly Leu Gln Ala Leu Asp Ser Trp
            20                  25                  30

Gln Asp Ala Met Gly His Pro Glu Gly Tyr Lys Leu Gly Ser Leu Ala
        35                  40                  45

Asn Gly Thr Ile Phe Gly Ser Val Leu Ser Val Ser Val Ala Ala Trp
    50                  55                  60

Leu Ser Asp Lys Val Gly Arg Arg Val Ala Ile Ile Ile Gly Ser Gly
65                  70                  75                  80

```
Ile Ala Val Val Gly Ala Ile Leu Gln Gly Ala Ser Thr Asn Phe Ala
                85                  90                  95

Phe Phe Leu Val Ser Arg Ile Leu Leu Gly Phe Gly Val Gly Ile Gly
               100                 105                 110

Ala Ile Ala Ser Pro Ala Leu Ile Ala Glu Ile Ser Tyr Pro Thr Phe
               115                 120                 125

Arg Pro Thr Cys Thr Thr Leu Tyr Asn Thr Leu Trp Tyr Leu Gly Ala
            130                 135                 140

Val Ile Ala Ala Trp Val Thr Phe Gly Thr Gln His Leu Lys Gly Ser
145                 150                 155                 160

Ala Ser Trp Arg Val Pro Ser Tyr Ile Gln Ala Phe Leu Pro Ala Val
                165                 170                 175

Gln Phe Val Ser Leu Trp Trp Cys Pro Glu Ser Pro Arg Trp Met Ile
                180                 185                 190

Ala Lys Gly Arg Glu Asp Glu Ala Arg Gln Ile Leu Phe Lys Tyr His
                195                 200                 205

Thr Gly Gly Asp Gln Asp Asp Arg Ala Val Arg Leu Val Glu Phe Glu
            210                 215                 220

Ile Lys Glu Ile Lys Ala Ala Leu Glu Met Glu Lys Ile Cys Ser Asn
225                 230                 235                 240

Ser Lys Tyr Ser Asp Phe Leu Thr Ile Pro Ser Tyr Arg Lys Arg Leu
                245                 250                 255

Phe Leu Leu Ser Phe Thr Ala Ile Ile Met Gln Leu Ser Gly Asn Gly
                260                 265                 270

Leu Val Ser Tyr Tyr Leu Ser Lys Val Leu Thr Ser Ile Gly Ile Lys
                275                 280                 285

Ser Ala Asn Glu Gln Leu Ile Ile Asn Gly Cys Leu Met Ile Tyr Asn
            290                 295                 300

Met Val Ile Ala Ser Ser Val Ala Phe Val Val Tyr Leu Phe Arg Arg
305                 310                 315                 320

Arg Thr Leu Phe Leu Thr Ser Ile Ser Gly Met Leu Phe Ser Tyr Ile
                325                 330                 335

Ile Trp Thr Ala Leu Ser Ala Val Asn Gln Gln Arg Asp Phe Lys Asp
                340                 345                 350

Lys Ser Leu Gly Lys Gly Val Leu Ala Met Ile Phe Phe Tyr Tyr Leu
            355                 360                 365

Ser Tyr Asp Ile Gly Ala Asn Gly Leu Pro Phe Leu Tyr Val Thr Glu
            370                 375                 380

Ile Leu Pro Tyr Thr His Arg Ala Lys Gly Leu Asn Val Met Tyr Gly
385                 390                 395                 400

Val Gln Met Thr Thr Leu Val Tyr Asn Gly Tyr Val Asn Pro Ile Ala
                405                 410                 415

Met Asp Ala Leu Asp Trp Lys Tyr Tyr Ile Val Trp Cys Cys Phe Leu
                420                 425                 430

Ala Phe Glu Leu Leu Ile Val Tyr Phe Phe Val Glu Thr Tyr Gly
            435                 440                 445

Tyr Ser Leu Glu Glu Val Ala Lys Val Phe Gly Asp Asp Pro Asn Ser
            450                 455                 460

Ser Leu Ile Gln Ser Thr Ser Ser Asn Glu Lys Ala Ser Ile Glu His
465                 470                 475                 480

Leu Glu Asp Thr Ser Ser Ala Glu Ile Gly Arg Val Val
                485                 490
```

<210> SEQ ID NO 58
<211> LENGTH: 500
<212> TYPE: PRT
<213> ORGANISM: Scheffersomyces stipitis

<400> SEQUENCE: 58

```
Trp Trp Lys His Lys His Phe Arg Phe Leu Asn Leu Cys Ile Trp Leu
1               5                   10                  15

Ile Ala Leu Thr Ser Thr Asn Asn Gly Tyr Asp Ser Ser Met Leu Asn
            20                  25                  30

Gly Leu Gln Ser Leu Pro Lys Trp Lys Leu Asp Met Gly Ser Pro Val
        35                  40                  45

Gly Pro Val Leu Gly Ala Leu Asn Asn Gly Asn Thr Phe Gly Val Met
    50                  55                  60

Leu Ser Phe Leu Leu Ala Ser Trp Ile Ala Asp Lys Trp Gly Arg Lys
65                  70                  75                  80

Lys Ala Ile Ile Gly Gly Ser Ser Leu Met Val Ile Gly Ala Ile Leu
                85                  90                  95

Gln Gly Val Ser Thr Asn Phe Gly Phe Phe Leu Phe Ser Arg Met Val
            100                 105                 110

Leu Gly Phe Gly Ser Gly Ile Ala Ile Val Ser Ser Pro Ser Leu Ile
        115                 120                 125

Ser Glu Leu Ala Tyr Pro Thr His Arg Ala Val Ala Thr Thr Leu Tyr
    130                 135                 140

Asn Val Phe Trp Tyr Leu Gly Ala Ile Ile Ala Ala Trp Val Thr Phe
145                 150                 155                 160

Gly Thr Arg Thr Leu His Ser Ser Tyr Cys Trp Arg Val Pro Ser Tyr
                165                 170                 175

Leu Gln Gly Phe Leu Pro Leu Val Gln Ile Leu Phe Phe Trp Leu Val
            180                 185                 190

Pro Glu Ser Pro Arg Tyr Leu Ile Ala Asn Gly Arg Thr Glu Glu Ala
        195                 200                 205

Arg Ala Ile Leu His Lys His His Thr Gly Ser Ser Asp Asp Glu Arg
    210                 215                 220

Ala His Ala Leu Ile Asn Phe Glu Val Ser Glu Ile Glu Ala Ala Leu
225                 230                 235                 240

Glu Gln Glu Lys Leu Tyr Ser Asn Ala Lys Tyr Ser Asp Phe Phe Thr
                245                 250                 255

Ile Pro Ser Phe Arg Met Arg Leu Phe Leu Val Val Trp Thr Ser Val
            260                 265                 270

Ile Met Gln Leu Ser Gly Asn Gly Leu Val Ser Tyr Tyr Leu Ser Lys
        275                 280                 285

Val Leu Ile Ser Ile Gly Ile Thr Gly Val Lys Glu Gln Leu Glu Ile
    290                 295                 300

Asn Gly Gly Leu Asn Ile Tyr Asn Leu Phe Val Ala Gly Phe Ile Ala
305                 310                 315                 320

Ser Asn Ala Asn Lys Phe Lys Arg Arg Thr Leu Phe Ile Thr Ala Leu
                325                 330                 335

Ser Gly Met Phe Ile Thr Tyr Val Ile Trp Thr Val Leu Ser Ala Ile
            340                 345                 350

Asn Gln Gln Arg Asp Phe Ser Asp Lys Ser Leu Gly Lys Gly Val Ile
        355                 360                 365

Ala Met Ile Phe Leu Phe Tyr Ile Phe Tyr Asn Met Gly Ala Asn Gly
    370                 375                 380
```

```
Leu Pro Trp Leu Tyr Met Thr Glu Ile Leu Pro Tyr Ser His Arg Ala
385                 390                 395                 400

Lys Gly Val Asn Ile His Asn Leu Val Gln Thr Trp Ile Val Ile Tyr
                405                 410                 415

Asn Gly Phe Val Asn Pro Ile Ala Met Asp Ala Ile Gln Trp Lys Tyr
            420                 425                 430

Tyr Ile Val Tyr Cys Cys Ile Ile Val Glu Leu Val Val Tyr
        435                 440                 445

Phe Thr Tyr Pro Glu Thr Ser Gly Tyr Thr Leu Glu Val Ala Arg
    450                 455                 460

Ala Phe Gly Asp Asp Glu Thr Thr His Leu Arg Phe Ile Asn Glu Thr
465                 470                 475                 480

Ser Lys Asp Lys Phe Gly Val Glu His Glu Ser Val Asp Ile Ala
                485                 490                 495

Ser Lys Thr Val
            500

<210> SEQ ID NO 59
<211> LENGTH: 476
<212> TYPE: PRT
<213> ORGANISM: Scheffersomyces stipitis

<400> SEQUENCE: 59

Ile Ser Asp Tyr Val Tyr His Asp Gln His Trp Trp Lys Tyr Asn His
1               5                   10                  15

Phe Arg Lys Leu His Trp Tyr Ile Phe Val Leu Thr Leu Thr Ser Thr
            20                  25                  30

Asn Asn Gly Tyr Asp Gly Ser Met Leu Asn Gly Leu Gln Ser Leu Ser
            35                  40                  45

Thr Trp Lys Asp Ala Met Gly Asn Pro Glu Gly Tyr Ile Leu Gly Ala
    50                  55                  60

Leu Ala Asn Gly Thr Ile Phe Gly Gly Val Leu Ala Val Ala Phe Ala
65                  70                  75                  80

Ser Trp Ala Cys Asp Arg Phe Gly Arg Lys Leu Thr Thr Cys Phe Gly
                85                  90                  95

Ser Ile Val Thr Val Ile Gly Ala Ile Leu Gln Gly Ala Ser Thr Asn
                100                 105                 110

Tyr Ala Phe Phe Phe Val Ser Arg Met Val Ile Gly Phe Gly Phe Gly
            115                 120                 125

Leu Ala Ser Val Ala Ser Pro Thr Leu Ile Ala Glu Leu Ser Phe Pro
    130                 135                 140

Thr Tyr Arg Pro Thr Cys Thr Ala Leu Tyr Asn Val Phe Trp Tyr Leu
145                 150                 155                 160

Gly Ala Val Ile Ala Ala Trp Val Thr Tyr Gly Thr Arg Thr Ile Val
                165                 170                 175

Ser Ala Tyr Ser Trp Arg Ile Pro Ser Tyr Leu Gln Gly Leu Leu Pro
            180                 185                 190

Leu Val Gln Val Cys Leu Val Trp Trp Val Pro Glu Ser Pro Arg Phe
        195                 200                 205

Leu Val Ser Lys Gly Lys Ile Glu Lys Ala Arg Glu Phe Leu Ile Lys
    210                 215                 220

Phe His Thr Gly Asn Asp Thr Gln Glu Gln Ala Thr Arg Leu Val Glu
225                 230                 235                 240

Phe Glu Leu Lys Glu Ile Glu Ala Ala Leu Glu Met Glu Lys Ile Asn
```

```
                    245                 250                 255
Ser Asn Ser Lys Tyr Thr Asp Phe Ile Thr Ile Lys Thr Phe Arg Lys
            260                 265                 270

Arg Ile Phe Leu Val Ala Phe Thr Ala Cys Met Thr Gln Leu Ser Gly
            275                 280                 285

Asn Gly Leu Val Ser Tyr Tyr Leu Ser Lys Val Leu Ile Ser Ile Gly
            290                 295                 300

Ile Thr Gly Glu Lys Glu Gln Leu Gln Ile Asn Gly Cys Leu Met Ile
305                 310                 315                 320

Tyr Asn Leu Val Leu Ser Leu Ala Val Ala Phe Thr Cys Tyr Leu Phe
                    325                 330                 335

Arg Arg Lys Ala Leu Phe Ile Phe Ser Cys Ser Phe Met Leu Leu Ser
                    340                 345                 350

Tyr Val Ile Trp Thr Ile Leu Ser Ala Ile Asn Gln Gln Arg Asn Phe
                    355                 360                 365

Glu Gln Lys Gly Leu Gly Gln Gly Val Leu Ala Met Ile Phe Ile Tyr
            370                 375                 380

Tyr Leu Ala Tyr Asn Ile Gly Leu Asn Gly Leu Pro Tyr Leu Tyr Val
385                 390                 395                 400

Thr Glu Ile Leu Pro Tyr Thr His Arg Ala Lys Gly Ile Asn Leu Tyr
                    405                 410                 415

Ser Leu Val Ile Asn Ile Thr Leu Ile Tyr Asn Gly Phe Val Asn Ala
                    420                 425                 430

Ile Ala Met Asp Ala Ile Ser Trp Lys Tyr Tyr Ile Val Tyr Cys Cys
            435                 440                 445

Ile Ile Ala Val Glu Leu Val Val Ile Phe Thr Tyr Val Glu Thr
            450                 455                 460

Phe Gly Tyr Thr Leu Glu Glu Val Ala Arg Val Phe
465                 470                 475

<210> SEQ ID NO 60
<211> LENGTH: 534
<212> TYPE: PRT
<213> ORGANISM: Scheffersomyces stipitis

<400> SEQUENCE: 60

Met Ser Gln Ser Lys Glu Lys Ser Asn Val Ile Thr Thr Val Leu Ser
1               5                   10                  15

Glu Glu Leu Pro Val Lys Tyr Ser Glu Glu Ile Ser Asp Tyr Val Tyr
            20                  25                  30

His Asp Gln His Trp Trp Lys Tyr Asn His Phe Arg Lys Leu His Trp
        35                  40                  45

Tyr Ile Phe Val Leu Thr Leu Thr Ser Thr Asn Gly Tyr Asp Gly
50                  55                  60

Ser Met Leu Asn Gly Leu Gln Ser Leu Ser Thr Trp Lys Asp Ala Met
65                  70                  75                  80

Gly Asn Pro Glu Gly Tyr Ile Leu Gly Ala Leu Ala Asn Gly Thr Ile
            85                  90                  95

Phe Gly Gly Val Leu Ala Val Ala Phe Ala Ser Trp Ala Cys Asp Arg
        100                 105                 110

Phe Gly Arg Lys Leu Thr Thr Cys Phe Gly Ser Ile Val Thr Val Ile
    115                 120                 125

Gly Ala Ile Leu Gln Gly Ala Ser Thr Asn Tyr Ala Phe Phe Phe Val
130                 135                 140
```

Ser Arg Met Val Ile Gly Phe Gly Phe Gly Leu Ala Ser Val Ala Ser
145                 150                 155                 160

Pro Thr Leu Ile Ala Glu Leu Ser Phe Pro Thr Tyr Arg Pro Thr Cys
            165                 170                 175

Thr Ala Leu Tyr Asn Val Phe Trp Tyr Leu Gly Ala Val Ile Ala Ala
            180                 185                 190

Trp Val Thr Tyr Gly Thr Arg Thr Ile Val Ser Ala Tyr Ser Trp Arg
        195                 200                 205

Ile Pro Ser Tyr Leu Gln Gly Leu Leu Pro Leu Val Gln Val Cys Leu
    210                 215                 220

Val Trp Val Pro Glu Ser Pro Arg Phe Leu Val Ser Lys Gly Lys
225                 230                 235                 240

Ile Glu Lys Ala Arg Glu Phe Leu Ile Lys Phe His Thr Gly Asn Asp
                245                 250                 255

Thr Gln Glu Gln Ala Thr Arg Leu Val Glu Phe Glu Leu Lys Glu Ile
            260                 265                 270

Glu Ala Ala Leu Glu Met Glu Lys Ile Asn Ser Asn Ser Lys Tyr Thr
        275                 280                 285

Asp Phe Ile Thr Ile Lys Thr Phe Arg Lys Arg Ile Phe Leu Val Ala
    290                 295                 300

Phe Thr Ala Cys Met Thr Gln Leu Ser Gly Asn Gly Leu Val Ser Tyr
305                 310                 315                 320

Tyr Leu Ser Lys Val Leu Ile Ser Ile Gly Ile Thr Gly Glu Lys Glu
                325                 330                 335

Gln Leu Gln Ile Asn Gly Cys Leu Met Ile Tyr Asn Leu Val Leu Ser
            340                 345                 350

Leu Ala Val Ala Phe Thr Cys Tyr Leu Phe Arg Arg Lys Ala Leu Phe
        355                 360                 365

Ile Phe Ser Cys Ser Phe Met Leu Leu Ser Tyr Val Ile Trp Thr Ile
    370                 375                 380

Leu Ser Ala Ile Asn Gln Gln Arg Asn Phe Glu Gln Lys Gly Leu Gly
385                 390                 395                 400

Gln Gly Val Leu Ala Met Ile Phe Ile Tyr Tyr Leu Ala Tyr Asn Ile
                405                 410                 415

Gly Leu Asn Gly Leu Pro Tyr Leu Tyr Val Thr Glu Ile Leu Pro Tyr
            420                 425                 430

Thr His Arg Ala Lys Gly Ile Asn Leu Tyr Ser Leu Val Ile Asn Ile
        435                 440                 445

Thr Leu Ile Tyr Asn Gly Phe Val Asn Ala Ile Ala Met Asp Ala Ile
    450                 455                 460

Ser Trp Lys Tyr Ile Val Tyr Cys Cys Ile Ile Ala Val Glu Leu
465                 470                 475                 480

Val Val Val Ile Phe Thr Tyr Val Glu Thr Phe Gly Tyr Thr Leu Glu
                485                 490                 495

Glu Val Ala Arg Val Phe Glu Gly Thr Asp Ser Leu Ala Met Asp Ile
            500                 505                 510

Asn Leu Asn Gly Thr Val Ser Asn Glu Lys Ile Asp Ile Val His Ser
        515                 520                 525

Glu Arg Gly Ser Ser Ala
    530

<210> SEQ ID NO 61
<211> LENGTH: 554
<212> TYPE: PRT

<213> ORGANISM: Scheffersomyces stipitis

<400> SEQUENCE: 61

```
Met Ser Ser Glu Met Leu Ser Lys Ser Glu Val Lys Tyr Glu Gln Asn
1               5                   10                  15
Glu Met Glu Gly Ser Gln Glu Lys Leu Ala Leu Lys Asp Glu Asp Ser
            20                  25                  30
Lys Asp Phe Tyr Lys Val Asn Glu Ala Tyr Asn Glu Lys Gly Phe Pro
        35                  40                  45
Leu Leu Ser Arg Pro Met Ile Pro Leu Leu Leu Thr Cys Ser Val Val
    50                  55                  60
Tyr Phe Val Ser Thr Asn Thr Gly Phe Asp Gly Ser Leu Met Ser Ser
65                  70                  75                  80
Ile Tyr Thr Gln Gln Asp Tyr Leu Asp Lys Phe Asn Leu Ser Ile Asn
                85                  90                  95
Ser Ser Thr Ser Thr Gly Leu Val Phe Ser Ile Tyr Asn Val Ala Gln
            100                 105                 110
Ile Cys Ala Ala Phe Phe Cys Pro Leu Ile Asp Phe Trp Gly Arg Lys
        115                 120                 125
Lys Leu Ile Leu Ile Gly Cys Trp Gly Thr Val Leu Gly Ala Ile Ile
    130                 135                 140
Thr Ala Phe Ala Gln Asn Lys Glu Thr Leu Ile Ala Gly Arg Phe Val
145                 150                 155                 160
Leu Ser Phe Phe Thr Thr Leu Ala Asn Thr Ser Ala Ser Leu Tyr Val
                165                 170                 175
Thr Glu Ile Ala Asn Thr Tyr Asn Arg Ser Val Val Ala Gly Cys Tyr
            180                 185                 190
Asn Thr Leu Trp Tyr Ile Gly Ser Val Leu Ala Ala Phe Thr Ser Tyr
        195                 200                 205
Gly Ala Asn Val Asn Leu Gly Gly Thr Glu Leu Ala Phe Arg Leu Pro
    210                 215                 220
Leu Gly Ile Gln Ala Val Phe Pro Gly Leu Val Gly Ile Phe Gly Phe
225                 230                 235                 240
Phe Ile Pro Glu Ser Pro Arg Trp Leu Val Gly Val Gly Arg Glu Lys
                245                 250                 255
Glu Ala Glu Glu Met Ile Ala Lys Tyr His Cys Asn Gly Asp Phe Ser
            260                 265                 270
His Pro Leu Leu Glu His Glu Met Val Gln Ile Asn Glu Ser Phe Arg
        275                 280                 285
Gly Asn Lys Leu Ala Gln Ser Leu Lys Ile Leu Asp Leu Arg Pro Ile
    290                 295                 300
Phe Gln Asn Asn Asn Ala Tyr Arg Ser Ile Leu Val Ile Leu Met Ala
305                 310                 315                 320
Phe Phe Gly Gln Phe Ser Gly Asn Asn Val Cys Ser Tyr Tyr Leu Pro
                325                 330                 335
Thr Met Leu Arg Asn Ile Gly Met Thr Thr Val Ser Thr Asn Val Leu
            340                 345                 350
Met Asn Ala Phe Tyr Ser Leu Ile Ser Trp Phe Ser Ser Ile Ala Gly
        355                 360                 365
Ser Phe Ala His Gln Lys Val Gly Arg Arg Lys Met Phe Met Phe Ser
    370                 375                 380
Thr Leu Ala Ala Ser Ala Cys Leu Thr Gly Leu Ala Val Ala Thr Ala
385                 390                 395                 400
```

```
Arg Tyr Gln Ala Thr Ser Ala Phe Ala Ala Ser Thr Thr Ala Ile Val
                405                 410                 415

Phe Ile Tyr Leu Phe Gly Val Met Phe Ser Phe Ala Phe Thr Pro Met
            420                 425                 430

Gln Pro Ile Tyr Pro Ala Glu Ile Ser Ser Asn Val Leu Arg Ser Arg
            435                 440                 445

Ser Met Ile Val Leu Asn Ile Thr Ala Gly Cys Ala Gln Phe Ile Asn
450                 455                 460

Gln Phe Ala Ala Pro Ala Met Glu Asn Ile Lys Tyr Trp Phe Tyr
465                 470                 475                 480

Val Phe Tyr Val Phe Trp Asp Ile Phe Glu Cys Ile Ile Ile Tyr Phe
                485                 490                 495

Phe Phe Val Glu Thr Lys Gly Lys Ser Leu Glu Glu Ile Asp Ala Ile
                500                 505                 510

Phe Glu Ala Arg Asn Pro Arg Lys Val Ser Val Gly Asp Tyr Ser Asp
                515                 520                 525

Glu Asp Gly Pro Lys Ile Asn Trp Leu Tyr Met Arg Ser Val Gly Gln
530                 535                 540

Tyr Val Ser Arg Arg Lys Ser Gly Met Asn
545                 550

<210> SEQ ID NO 62
<211> LENGTH: 555
<212> TYPE: PRT
<213> ORGANISM: Scheffersomyces stipitis

<400> SEQUENCE: 62

Met Ser Thr Asn Ser Leu Asn Asp Ser Tyr Asn Pro Ser Ser Thr Lys
1               5                   10                  15

Glu Lys Asp Ile Val Val Gln Ser Glu Ala Leu Ala Asp Val Ala Ile
                20                  25                  30

Glu Thr Ala Phe Glu Thr Asp Gly Tyr Lys Lys Ile Phe Gln Glu His
            35                  40                  45

Pro Val Pro Arg Trp Thr Lys Ser Arg Leu Ser Ile Tyr Phe Thr Cys
50                  55                  60

Leu Val Ile Tyr Leu Val Ser Thr Thr Asn Gly Tyr Asp Gly Ser Leu
65                  70                  75                  80

Leu Ser Ser Leu Ile Thr Met Pro Glu Phe Ile Ser His Leu Asn Ile
                85                  90                  95

Lys Ser Ala Ser Gly Thr Gly Ile Val Phe Ala Ile Phe Gln Val Gly
            100                 105                 110

Gln Met Val Ala Thr Leu Phe Val Trp Leu Gly Asp Phe Ile Gly Arg
            115                 120                 125

Arg Asn Ala Ile Phe Ile Gly Ser Val Ile Val Cys Leu Gly Ala Ile
130                 135                 140

Ile Thr Ser Ile Ala Asn Asn Thr Ser Thr Phe Ile Gly Gly Arg Phe
145                 150                 155                 160

Leu Leu Ser Phe Gly Ser Gly Ile Ser Cys Ala Leu Ser Thr Thr Tyr
                165                 170                 175

Leu Leu Glu Ile Thr Ser Pro Asp Glu Arg Ser Ala Leu Cys Ala Ile
            180                 185                 190

Tyr Asn Ser Leu Tyr Tyr Ile Gly Ser Ile Ile Ala Thr Trp Ser Ser
            195                 200                 205

Tyr Ala Thr Ser Ile Ser Tyr Ala Asn Ser Val Leu Ser Phe Arg Ile
210                 215                 220
```

Pro Leu Trp Leu Gln Ile Leu Cys Pro Ala Leu Val Ile Gly Leu
225                 230                 235                 240

Leu Val Gly Val Ala Pro Glu Ser Pro Arg Phe Tyr Leu Thr Gly
            245                 250                 255

Gln Pro Asp Lys Ala Arg Ala Phe Phe Cys Lys Tyr His Ala Asn Gly
        260                 265                 270

Asp Glu Lys His Pro Ile Val Glu Tyr Glu Met Ala Gln Leu Glu Leu
        275                 280                 285

Ser Leu Leu Glu Val Pro Lys Leu Arg Val Arg Asp Tyr Phe Asp Ala
290                 295                 300

Arg Ile Leu Phe Lys Thr Lys Ser Arg Ile Tyr Arg Ser Leu Val Cys
305                 310                 315                 320

Ile Ala His Ser Ala Phe Gly Gln Leu Ser Gly Asn Ala Val Val Gly
            325                 330                 335

Tyr Tyr Ile Thr Asn Ile Phe Leu Glu Leu Gly Ile Thr Asn Pro Thr
            340                 345                 350

Thr Arg Leu Leu Leu Asn Gly Val Asn Ser Ile Leu Gly Phe Ile Phe
        355                 360                 365

Ala Met Ser Gly Ser Ile Leu Val Gly Arg Ile Gly Arg Arg Pro Ile
370                 375                 380

Leu Leu Tyr Ser Thr Thr Gly Phe Val Ile Ser Phe Thr Ile Ile Ala
385                 390                 395                 400

Ala Cys Ile Ala Ala Tyr Thr Asn Asn Asn Asn Gln Val Ala Ala Lys
            405                 410                 415

Val Gly Ile Ala Phe Ile Tyr Ile Phe Asn Asn Val Phe Ser Phe
            420                 425                 430

Gly Tyr Thr Pro Leu Gln Pro Leu Tyr Pro Ala Glu Ile Leu Ser Ser
            435                 440                 445

Glu Met Arg Ala Lys Gly Met Ala Leu Phe Gln Ile Thr Gln Gly Thr
450                 455                 460

Ala Ser Phe Ile Asn Thr Tyr Ala Ala Pro Val Ala Met Gln Asn Ile
465                 470                 475                 480

Lys Tyr Trp Tyr Tyr Val Phe Phe Val Phe Trp Asp Thr Phe Glu Val
            485                 490                 495

Ile Ile Ile Tyr Leu Tyr Phe Val Glu Thr Lys Asn Leu Thr Leu Glu
            500                 505                 510

Glu Ile Glu Leu Ile Phe Glu Ser Ala Thr Pro Val Lys Thr Ser Met
        515                 520                 525

Ile Ile Ser Lys Pro Gly His Ala Ala Asn Glu Glu Lys Leu Arg Leu
        530                 535                 540

Ala Asn Leu Lys Leu Gly Lys Asn Tyr Val Ala
545                 550                 555

<210> SEQ ID NO 63
<211> LENGTH: 499
<212> TYPE: PRT
<213> ORGANISM: Scheffersomyces stipitis

<400> SEQUENCE: 63

Leu Tyr Thr Ile Cys Ala Gly Leu Tyr Leu Cys Ser Thr Met Asn Gly
1               5                   10                  15

Tyr Asp Gly Ser Leu Gln Thr Ala Ile Glu Thr Leu Pro Ala Tyr Arg
            20                  25                  30

Thr Tyr Phe Asn Leu Ser Asn Ser Ala Ser Asp Thr Gly Leu Val Phe

-continued

```
                35                  40                  45
Ser Ile Phe Pro Ala Gly Ala Ile Cys Ala Thr Ile Phe Ile Trp Leu
 50                  55                  60
Gly Asp Tyr Ile Gly Arg Val Leu Thr Ile Ile Gly Leu Val Gly
 65                  70                  75                  80
Thr Ile Val Gly Ser Ile Val Ser Ser Thr His Asn His Ser Ala
                     85                  90                  95
Tyr Ile Gly Gly Arg Phe Leu Leu Ser Phe Ser Thr Ile Ala Asn
                    100                 105                 110
Cys Thr Ala Ala Ile Leu Leu Thr Glu Ser Val Pro Tyr Asp Met Arg
                    115                 120                 125
Trp Leu Val Gly Cys Phe Asn Thr Phe Tyr Tyr Ile Gly Ser Ile Ile
                    130                 135                 140
Ala Thr Trp Thr Met Tyr Gly Thr Ser Lys Asn Phe Glu Gly Pro Gln
145                 150                 155                 160
Thr Phe Lys Ile Gly Leu Trp Leu Gln Ile Leu Cys Pro Gly Met Ala
                    165                 170                 175
Leu Val Leu Ile Cys Ser Ser Ala Leu Leu Gly Phe Gly Asp Ser Pro
                    180                 185                 190
Arg Tyr Tyr Gly Lys Asn Lys Ile Glu Thr Ala Arg Asp Phe Ile
                    195                 200                 205
Ile Lys Tyr His Ala Asn Gly Asp Val Ser His Pro Ile Val Ala Ala
                    210                 215                 220
Glu Met Glu Glu Leu Glu Leu Ser Phe Arg Thr Asn Gly Phe Leu Lys
225                 230                 235                 240
Pro Lys Asp Tyr Leu Asn Tyr Ser Asn Phe Phe Arg Thr Thr Ser Asn
                    245                 250                 255
Arg Lys Arg Thr Ala Leu Val Val Ala Trp Ser Trp Phe Asn Gln Phe
                    260                 265                 270
Ser Gly Asn Gln Val Ile Thr Tyr Tyr Met Thr Thr Leu Phe Leu Thr
                    275                 280                 285
Leu Gly Ile Lys Asn Ala Thr Thr Arg Leu Leu Leu Thr Gly Ile Asn
                    290                 295                 300
Ser Ile Leu Cys Tyr Ile Phe Ala Thr Cys Gly Gly Leu Leu Ile Asp
305                 310                 315                 320
Arg Leu Pro Arg Arg Trp Val Leu Leu Tyr Ala Asn Ala Gly Phe Val
                    325                 330                 335
Ile Cys Phe Ala Gly Leu Ala Ala Ala Val Arg Ala Phe Gln Ala Asp
                    340                 345                 350
Ala Asn Asn His Thr Ala Ala Ser Ala Gly Ile Ala Phe Met Tyr Leu
                    355                 360                 365
Phe Met Thr Ile Phe Phe Ser Phe Ala Phe Thr Pro Leu Gln Pro Ile
                    370                 375                 380
Tyr Pro Ala Glu Val Met Ser Asn Asp Met Arg Gly Arg Gly Met Ala
385                 390                 395                 400
Leu Tyr Phe Phe Ile Ser Asn Val Ala Ser Phe Val Asn Leu Tyr Ser
                    405                 410                 415
Ala Pro Val Ala Met Gln Asn Ile Lys Tyr Trp Tyr Tyr Val Phe Phe
                    420                 425                 430
Val Phe Trp Asp Ala Phe Gln Phe Ala Ile Ile Tyr Phe Phe Val
                    435                 440                 445
Glu Thr Cys Ala Leu Thr Leu Glu Glu Ile Glu Val Val Phe Lys Glu
450                 455                 460
```

```
Lys His Thr Val Lys Glu Ser Ile Lys Phe Asn Lys Arg Lys Glu Glu
465                 470                 475                 480

Ile Met Arg Glu Glu Glu Ile Thr Arg Glu Glu Tyr Thr Glu Gln Lys
                485                 490                 495

Thr Asn Ser
```